(12) United States Patent
Glossop et al.

(10) Patent No.: US 11,014,966 B2
(45) Date of Patent: May 25, 2021

(54) COMPOUNDS AND THERAPEUTICS USES THEREOF

(71) Applicant: Centauri Therapeutics Limited (GB/GB), London (GB)

(72) Inventors: Melanie Glossop, Sandwich (GB); Christine Watson, Sandwich (GB); Michael Westby, Sandwich (GB)

(73) Assignee: CENTUARI THERAPEUTICS LIMITED, London (GB)

(*) Notice: Subject to any disclaimer, the term of this patent is extended or adjusted under 35 U.S.C. 154(b) by 83 days.

(21) Appl. No.: 16/333,219

(22) PCT Filed: Sep. 13, 2017

(86) PCT No.: PCT/GB2017/052699
§ 371 (c)(1),
(2) Date: Mar. 13, 2019

(87) PCT Pub. No.: WO2018/051085
PCT Pub. Date: Mar. 22, 2018

(65) Prior Publication Data
US 2019/0248838 A1     Aug. 15, 2019

(30) Foreign Application Priority Data

Sep. 13, 2016 (GB) .................................. 1615560
May 4, 2017 (GB) .................................. 1707076

(51) Int. Cl.
| | |
|---|---|
| C07K 7/62 | (2006.01) |
| A61K 47/61 | (2017.01) |
| A61K 47/64 | (2017.01) |
| A61P 31/00 | (2006.01) |

(52) U.S. Cl.
CPC ............. *C07K 7/62* (2013.01); *A61K 47/61* (2017.08); *A61K 47/646* (2017.08); *A61P 31/00* (2018.01)

(58) Field of Classification Search
CPC ......... A61P 31/00; A61K 47/61; A61K 47/66; A61K 47/646; C07K 7/62

USPC .................. 424/9.1; 435/455, 458; 514/44 A
See application file for complete search history.

(56) References Cited

U.S. PATENT DOCUMENTS

2004/0185054 A1     9/2004    Mullis

FOREIGN PATENT DOCUMENTS

| WO | 2017/060728 A1 | 4/2017 |
| WO | 2017/060729 A1 | 4/2017 |

OTHER PUBLICATIONS

U.S. Appl. No. 15/766,193 (Year: 2015).*
Tsubery et al, Antimicrobial Agents and Chemotherapy, vol. 2, pp. 660-664. (Year: 2004).*
Ferguson E et al, Dextrin-Colistin Conjugates as a Model Bioresponsive Treatment for Multidrug Resistant Bacterial Infections, Mol Pharmaceutics, 2014, 11, 4437-4447.
Kristian S et al, Retargeting pre-existing human antibodies to a bacterial pathogen with an alpha-Gal conjugated aptamer, JMOL Med, 2015, 93, 619-631.
Li Jun et al, Bacteria Targeted by Human Natural Antibodies Using a-Gal Conjugated Receptor-specific Glycopolymers, Bioorg. Med., Chem. 7, 1999, 1549-1558.
Niaicker K P et al, Design and synthesis of aGal-conjugated peptide T20 as novel antiviral agent for HIV-immunotargeting, Org. Biomol. Chem., 2004, 2, 660-664.
Tsubery H et al, Neopeptide Antibiotics That Function as Opsonins and Membrane-Permeabilizing Agents for Grain-Negative Bacteria, Antimicrobial Agents and Chemotherapy, 2005, 3122-3128, 49.
International Search Report and Written Opinion of PCT/GB2017/052699 dated Dec. 5, 2017.

* cited by examiner

*Primary Examiner* — Jane J Zara
(74) *Attorney, Agent, or Firm* — Aura IP Law, PC

(57) ABSTRACT

The invention relates to novel compounds with the ability to link an immune response to a pathogen, to the use of said compounds in a disease or disorder mediated and/or caused by an infective agent, to compositions containing said compounds, processes for their preparation and to novel intermediates used in said process.

25 Claims, 5 Drawing Sheets

A

B

C
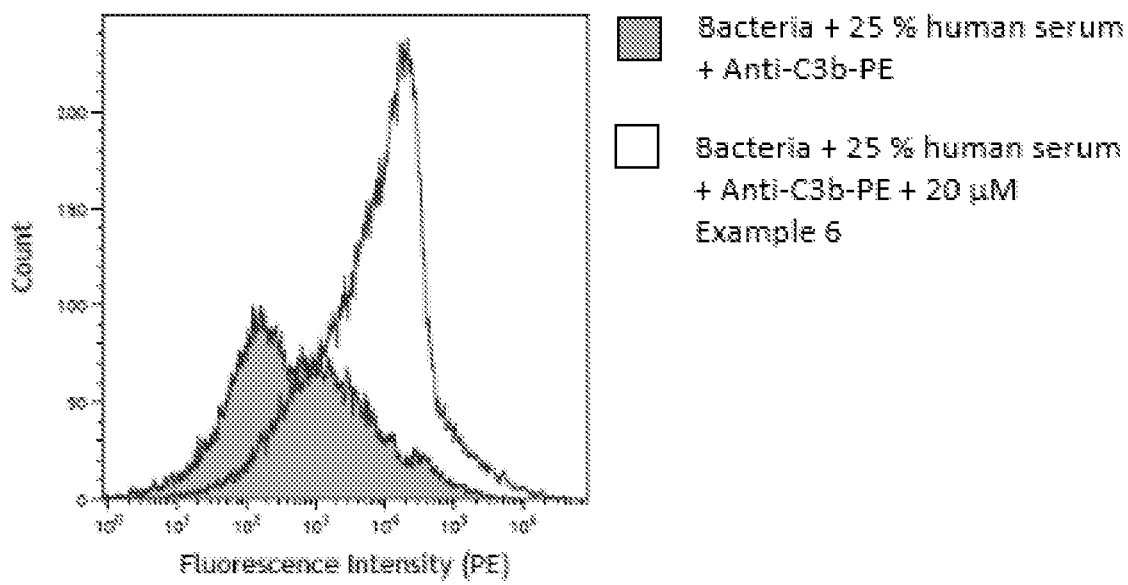
D
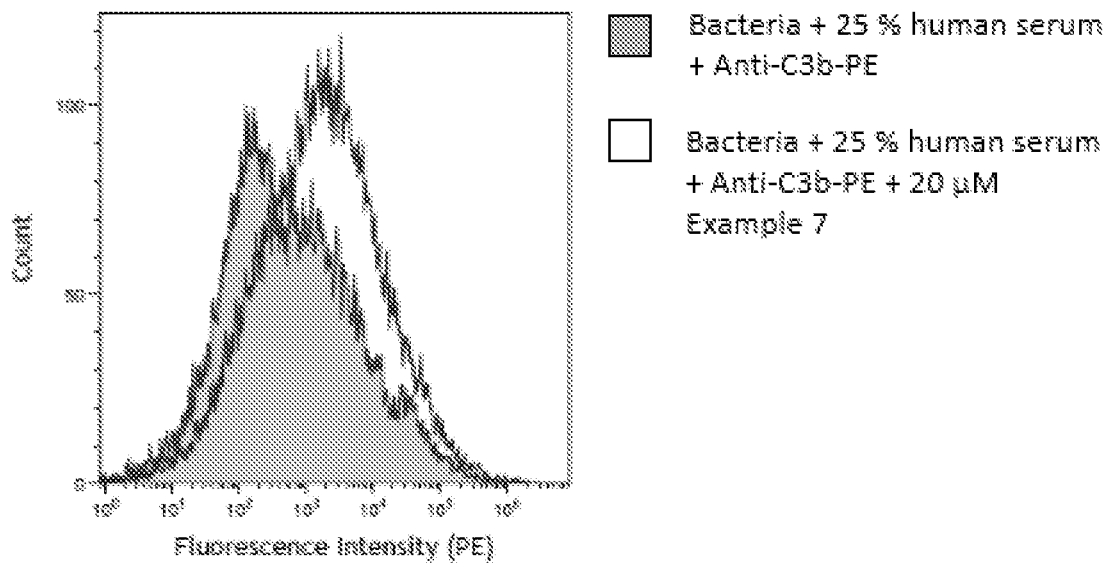
FIGURE 3 (ctd)

E
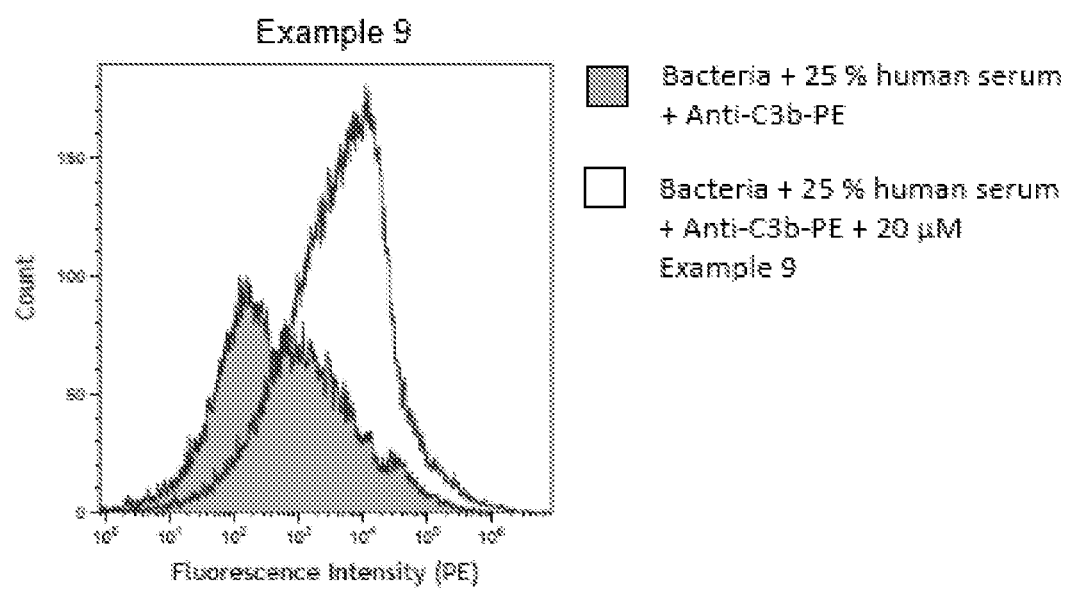
FIGURE 3 (ctd)

COMPOUNDS AND THERAPEUTICS USES THEREOF

CROSS-REFERENCE TO RELATED APPLICATIONS

The present application is a U.S. National Stage entry under 35 U.S.C. § 371 of International Application No. PCT/GB2017/052699 filed on Sep. 13, 2017, designating the United States of America and published in English on Mar. 22, 2018, which is hereby incorporated by reference in its entirety. International Application No. PCT/GB2017/052699 claims priority to Great Britain Application Nos. 1615560.8, filed Sep. 13, 2016 and 1707076.4 filed May 4, 2017, each of which is hereby incorporated by reference in its entirety.

FIELD OF THE INVENTION

The invention relates to novel compounds with the ability to link an immune response to a pathogen, to the use of said compounds in a disease or disorder mediated and/or caused by an infective agent, to compositions containing said compounds, processes for their preparation and to novel intermediates used in said process.

BACKGROUND OF THE INVENTION

There is a need to find novel ways to recruit an individual's immune system to fight disease.

The human immune system continually surveys the body seeking foreign signals to identify potentially harmful pathogens or mutated human cells (that could become a cause of cancerous growth) and target them for elimination. Natural antibodies exist that can be recruited to said pathogens or mutated human cells to drive the immune system to eliminate the threat. The invention details the use of a novel set of linker molecules that are designed to attract these natural antibodies in such a way as to be able to maximise the efficacy of immune recruitment while minimising potential side effects.

There is an urgent need to identify novel ways of treating bacterial, viral and fungal infections. Drug resistance is becoming a major global health threat. For example, more than 2 million people in the US were infected with bacteria resistant to at least one class of antibiotics (Centers for Disease Control and Prevention, 2013). Overall, the identification of new antibiotics targeting resistant strains of gram-negative organisms has been particularly difficult, in part due to the complex and evolving strategy these bacteria use to prevent antibiotic action (e.g., production of antibiotic inactivating enzymes, ability to transfer of resistance between strains, efflux pumps to prevent intracellular action) coupled with their naturally impermeable cell membranes that make it hard to identify drugs that penetrate into the cell and inhibit key targets. Further, many strains utilize multiple resistance mechanisms making it difficult for a single antibiotic to overcome.

An innovative approach to the treatment of infectious disease was disclosed in WO 01/45734 which describes a set of novel immunity linkers. Examples of said linker moieties include compounds or agents which are recognised by the immune system of said individual as foreign and which would therefore trigger an immune response. One such example is a carbohydrate molecule capable of binding to a human anti-alpha-galactosyl antibody (i.e. galactosyl-alpha-1,3-galactosyl-beta-1,4-N-acetylglucosamine) which results in redirection of the natural human serum antibody anti-alpha-galactosyl. The resultant effect of said immunity linker molecule is that the immune response of the individual is diverted from the pre-existing immune response of said individual towards the target, i.e. the pathogen.

There is therefore a need for alternative immunity linker molecules for the treatment of a disease or disorder mediated and/or caused by an infective agent.

SUMMARY OF THE INVENTION

According to a first aspect of the invention, there is provided a compound of formula (I) or a pharmaceutically acceptable salt thereof:

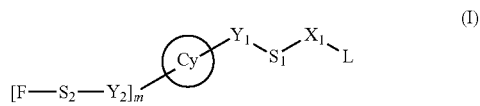

(I)

wherein:

L represents a binding moiety selected from a cationic anti-microbial peptide linked to $X_1$ by an amine;

$S_1$ represents a bond or a spacer selected from a —$(CH_2)_a$— or —$(CH_2)_b$—$(CH_2$—$CH_2$—$O)_c$—$(CH_2)_d$— group, wherein one to five of said —$CH_2$— groups may optionally be substituted by a —C(O)NH— or —NHC(O)— group;

a represents an integer selected from 1 to 40;
b represents an integer selected from 0 to 25;
c represents an integer selected from 1 to 20;
d represents an integer selected from 1 to 15;

$S_2$ represents a spacer selected from a —$(CH_2)_e$— or —$(CH_2)_f$—$(CH_2$—$CH_2$—$O)_g$—$(CH_2)_h$— group, wherein one to three of said —$CH_2$— groups may optionally be substituted by a —C(O)NH— or —NHC(O)— group;

e represents an integer selected from 1 to 20;
f represents an integer selected from 1 to 10;
g represents an integer selected from 1 to 15;
h represents an integer selected from 1 to 5;

$X_1$ represents a bond or —C(O)—;

$Y_1$ and $Y_2$ independently represent a bond, —O—, —S—, —NH—, —C(O)—, —NHC(O)— or —C(O)NH— group;

F represents a carbohydrate molecule capable of binding to a human anti-alpha-galactosyl antibody;

m represents an integer selected from 1 to 5; and

Cy represents phenyl, biphenyl or triphenyl, such that when Cy represents biphenyl or triphenyl, said —$Y_1$—$S_1$—$X_1$-L group may be present on any of said phenyl rings and said [F—$S_2$—$Y_2$]$_m$— group or groups may be present on any of said phenyl rings.

Figure 3:
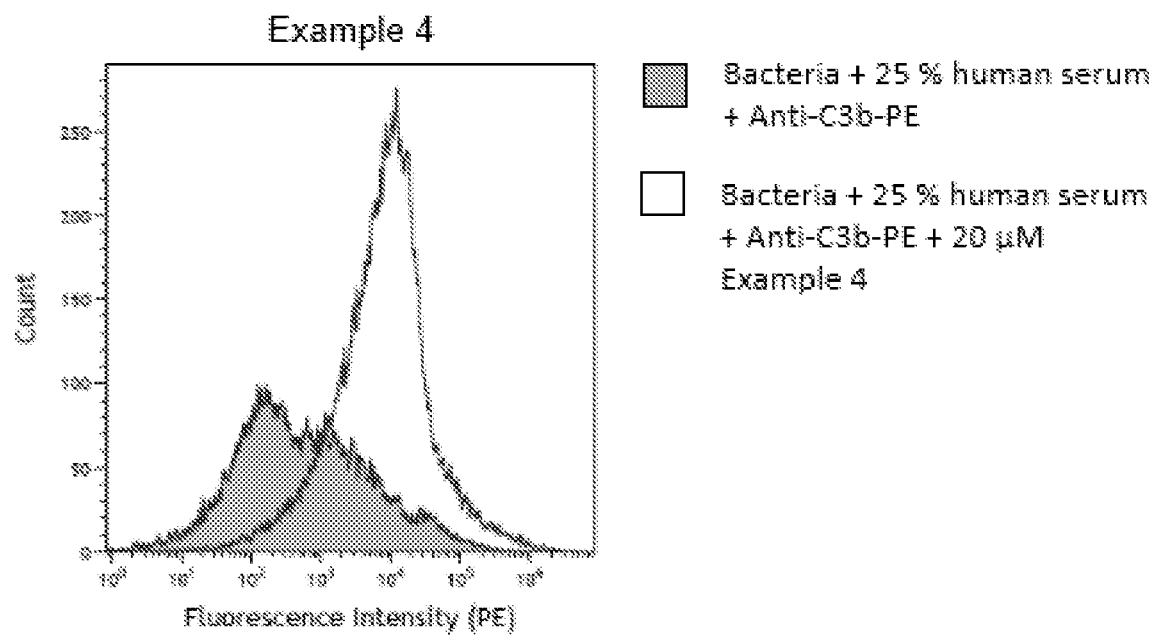
Figure 3:
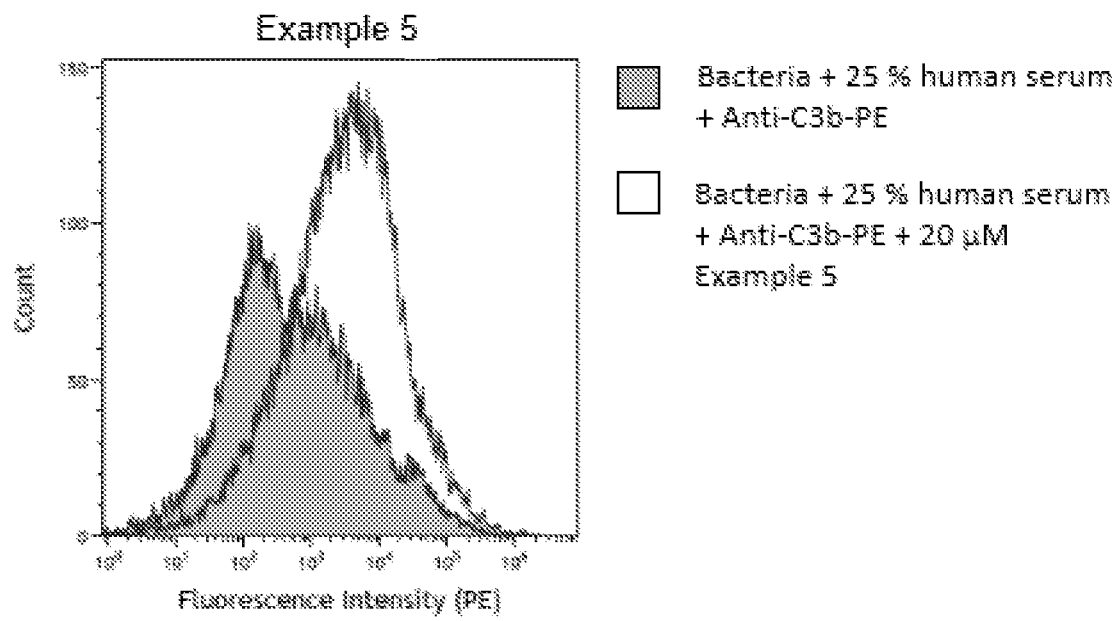

FIG. 3: Flow cytometry results for the recruitment of C3b from human serum to the surface of E. coli for Examples 4, 5, 6, 7 and 9.

DETAILED DESCRIPTION OF THE INVENTION

According to one particular aspect of the invention which may be mentioned, there is provided a compound of formula (I) or a pharmaceutically acceptable salt thereof:

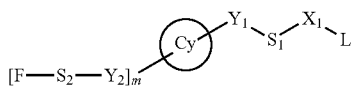

wherein:

L represents a binding moiety selected from a cationic anti-microbial peptide linked to $X_1$ by an amine;

$S_1$ represents a bond or a spacer selected from a —$(CH_2)_a$— or —$(CH_2)_b$—$(CH_2—CH_2—O)_c$—$(CH_2)_d$— group, wherein one or two of said —$CH_2$— groups may optionally be substituted by a —C(O)NH— or —NHC(O)— group;

a represents an integer selected from 1 to 15;
b represents an integer selected from 0 to 5;
c represents an integer selected from 1 to 20;
d represents an integer selected from 1 to 5;

$S_2$ represents a spacer selected from a —$(CH_2)_e$— or —$(CH_2)_f$—$(CH_2—CH_2—O)_g$—$(CH_2)_h$— group, wherein one or two of said —$CH_2$— groups may optionally be substituted by a —C(O)NH— or —NHC(O)— group;

e represents an integer selected from 1 to 15;
f represents an integer selected from 1 to 10;
g represents an integer selected from 1 to 15;
h represents an integer selected from 1 to 5;
$X_1$ represents a bond or —C(O)—;
$Y_1$ and $Y_2$ independently represent a bond, —O—, —S—, —NH—, —C(O)—, —NHC(O)— or —C(O)NH— group;
F represents a carbohydrate molecule capable of binding to a human anti-alpha-galactosyl antibody;
m represents an integer selected from 1 to 5; and
Cy represents phenyl, biphenyl or triphenyl, such that when Cy represents biphenyl or triphenyl, said —$Y_1$—$S_1$—$X_1$-L group may be present on any of said phenyl rings and said [F—$S_2$—$Y_2$]$_m$ group or groups may be present on any of said phenyl rings.

The invention comprises a conjugate of a cationic peptide (that specifically binds to bacteria) and the one or more units of the carbohydrate molecule capable of binding to a human anti-alpha-galactosyl antibody (i.e. alpha-Gal trisaccharide) connected via a linker. An example of a cationic peptide is polymyxin B (or polymyxin nonapeptide, colistin or a derivative thereof). This family of cationic peptides bind to lipid A on the bacterial cell surface and, when conjugated to alpha-gal linkers, will present alpha-Gal, resulting in anti-Gal antibody recruitment and cell killing. Resistance rates are likely to be low as lipid A is important in the survival of gram-negative bacteria. In fact, even polymyxin-resistant strains retain binding sites for cationic peptides and as such the peptide-alpha-Gal conjugate. Thus, the invention may retain efficacy even against these strains.

Clearly, new innovative therapies that work through novel mechanisms, and are not impacted by antibiotic resistance mechanisms, are particularly attractive. The solution provided by the invention, i.e. the combination of the broad spectrum bacterial binding capability of a cationic peptide with the unique ability to specifically recruit naturally occurring anti-Gal antibodies to the bacterial surface, and re-direct these antibodies to promote complement activation, phagocytosis and killing is very attractive. The invention has the potential to provide a novel therapy for bacterial infections with broad-spectrum activity. Efficacy that is independent of antibiotic resistance mechanisms has the potential to be effective against multi-drug resistant strains. The invention may work as a single agent as well as with standard-of-care treatment to reduce the dose and duration of therapy.

In one embodiment, $S_1$ represents: a bond or a spacer selected from:
—$(CH_2)_a$—, wherein one to five of said —$CH_2$— groups are optionally substituted by a —C(O)NH— or —NHC(O)— group (such as —$(CH_2)_5$—CONH—$(CH_2)_5$—, —$(CH_2)_5$—CONH—$(CH_2)_5$—CONH—$(CH_2)_5$—CONH—$(CH_2)_5$—CONH—$(CH_2)_5$—CONH —$(CH_2)_5$—, —$(CH_2)_2$—, —$CH_2$—CONH —$(CH_2)_2$—, —$CH_2$—NHCO—$(CH_2)_4$—CONH— $(CH_2)_2$— or —$(CH_2)_6$—); or
—$(CH_2)_b$—$(CH_2$—$CH_2$—$O)_c$—$(CH_2)_d$—, wherein one to five of said —$CH_2$— groups are optionally substituted by a —C(O)NH— or —NHC(O)— group (such as —$(CH_2CH_2O)_8$—$(CH_2)_2$—, —$(CH_2CH_2O)_8$—$(CH_2)_2$—CONH—$(CH_2)_5$—CONH—$(CH_2)_5$— or —$(CH_2)_5$—CONH—$(CH_2)_5$—CONH—$(CH_2)_5$—CONH—$(CH_2)_5$—CONH—$(CH_2CH_2O)_8$—$(CH_2)_2$—).

In a further embodiment, $S_1$ represents a bond or a spacer selected from —$(CH_2)_a$—, wherein one or two of said —$CH_2$— groups are optionally substituted by a —C(O)NH— or —NHC(O)— group (such as —$(CH_2)_5$—CONH—$(CH_2)_5$—, —$(CH_2)_2$—, —$CH_2$—CONH—$(CH_2)_2$—, —$CH_2$—NHCO—$(CH_2)_4$—CONH—$(CH_2)_2$— or —$(CH_2)_6$—) or —$(CH_2)_b$—$(CH_2$—$CH_2$—$O)_c$—$(CH_2)_d$—, wherein one or two of said —$CH_2$— groups are optionally substituted by a —C(O)NH— or —NHC(O)— group (such as —$(CH_2CH_2O)_8$—$(CH_2)_2$—).

In a further embodiment, $S_1$ represents a bond or a spacer selected from —$(CH_2)_a$—, wherein one or two of said —$CH_2$— groups are optionally substituted by a —C(O)NH— or —NHC(O)— group (such as —$(CH_2)_5$—CONH—$(CH_2)_5$) or —$(CH_2)_b$—$(CH_2$—$CH_2$—$O)_c$—$(CH_2)_d$—, wherein one or two of said —$CH_2$— groups are optionally substituted by a —C(O)NH— or —NHC(O)— group (such as —$(CH_2CH_2O)_8$—$(CH_2)_2$—).

In a yet further embodiment, $S_1$ represents: a bond or a spacer selected from:
—$(CH_2)_a$—, wherein one or five of said —$CH_2$— groups are optionally substituted by a —C(O)NH— group (such as —$(CH_2)_5$—CONH—$(CH_2)_5$ or —$(CH_2)_5$—CONH—$(CH_2)_5$—CONH—$(CH_2)_5$—CONH —$(CH_2)_5$—CONH—$(CH_2)_5$—CONH—$(CH_2)_5$—); or
—$(CH_2)_b$—$(CH_2$—$CH_2$—$O)_c$—$(CH_2)_d$—, wherein two of said —$CH_2$— groups are optionally substituted by a —C(O)NH— group (such as —$(CH_2CH_2O)_8$—$(CH_2)_2$—, —$(CH_2CH_2O)_8$—$(CH_2)_2$—CONH—$(CH_2)_5$—CONH—$(CH_2)_5$— or —$(CH_2)_5$—CONH—$(CH_2)_5$—CONH—$(CH_2)_5$—CONH—$(CH_2CH_2O)_8$—$(CH_2)_2$—).

In one embodiment, $S_1$ represents a bond. In an alternative embodiment, $S_1$ represents —$(CH_2)_a$—, wherein one or five of said —$CH_2$— groups are optionally substituted by a —C(O)NH— group (such as —$(CH_2)_5$—CONH—$(CH_2)_5$— or —$(CH_2)_5$—CONH—$(CH_2)_5$—CONH—$(CH_2)_5$—CONH—$(CH_2)_5$—CONH—$(CH_2)_5$—CONH—$(CH_2)_5$—). In an alternative embodiment, $S_1$ represents —$(CH_2)_b$—$(CH_2$—$CH_2$—$O)_c$—$(CH_2)_d$—, wherein two of said —$CH_2$— groups are optionally substituted by a —C(O)NH— group (such as —$(CH_2CH_2O)_8$—$(CH_2)_2$—, —$(CH_2CH_2O)_8$—$(CH_2)_2$—CONH—$(CH_2)_5$—CONH—$(CH_2)_5$— or —$(CH_2)_5$—CONH—$(CH_2)_5$—CONH—$(CH_2)_5$—CONH—$(CH_2)_5$—CONH—$(CH_2CH_2O)_8$—$(CH_2)_2$—).

In a further embodiment, $S_1$ represents a spacer selected from: —$(CH_2)_a$—, wherein one of said —$CH_2$— groups is substituted by a —C(O)NH— group (such as —$(CH_2)_5$—CONH—$(CH_2)_5$); or —$(CH_2)_b$—$(CH_2$—$CH_2$—$O)_c$—$(CH_2)_d$— (such as —$(CH_2CH_2O)_8$—$(CH_2)_2$—).

In a yet further embodiment, $S_1$ represents a spacer selected from: —$(CH_2)_a$—, wherein one of said —$CH_2$— groups is substituted by a —C(O)NH— group (such as —$(CH_2)_5$—CONH—$(CH_2)_5$).

It will be appreciated that a, b, c, d, e, f, g and h are selected to maintain a suitable linker length between groups F and L. Examples of suitable linker lengths between F and L range from about 5 Å to about 50 Å or more in length, about 6 Å to about 45 Å, about 7 Å to about 40 Å, about 8 Å to about 35 Å, about 9 Å to about 30 Å, about 10 Å to about 25 Å, about 11 Å to about 20 Å, about 12 Å to about 15 Å. Thus, in one embodiment, a, b, c, d, e, f, g and h represent a total integer of no more than 30, such as between 5 and 30, such as between 7 and 29.

In a further embodiment, a represents an integer selected from 1 to 35. In a further embodiment, a represents an integer selected from 1 to 10. In a further embodiment, a represents an integer selected from 2 to 13. In a yet further embodiment, a represents an integer selected from 2, 4, 6, 9 or 11. In a yet further embodiment, a represents an integer selected from 10 to 35. In a yet further embodiment, a represents an integer selected from 11 or 35. In a still yet further embodiment, a represents an integer selected from 11.

In one embodiment, b represents an integer selected from 0 to 24. In a further embodiment, b represents an integer selected from 0 to 3. In a further embodiment, b represents an integer selected from 0, 2 or 3. In a yet further embodiment, b represents an integer selected from 0 or 24. In a yet further embodiment, b represents an integer selected from 0.

In one embodiment, c represents an integer selected from 1 to 15. In a further embodiment, c represents an integer selected from 1 to 12. In a yet further embodiment, c represents an integer selected from 1 to 10. In a yet further embodiment, c represents an integer selected from 8.

In one embodiment, d represents an integer selected from 1 to 3. In a further embodiment, d represents an integer selected from 1 or 2. In a yet further embodiment, d represents an integer selected from 2.

In one embodiment, $Y_1$ represents —C(O)NH— or —O(O)—. In a further embodiment, $Y_1$ represents —C(O)NH—.

In one embodiment, $S_2$ represents a spacer selected from: —$(CH_2)_e$—, wherein one to three of said —$CH_2$— groups are optionally substituted by a —C(O)NH— or —NHC(O)— group (such as —$(CH_2)_3$—NHCO—$CH_2$—, —$(CH_2)_3$—NHCO—$(CH_2)_5$—NHCO—$(CH_2)_5$—NHCO—$CH_2$—, —$(CH_2)_3$—NHCO—, —$(CH_2)_3$—, —$(CH_2)_3$—NHCO—$(CH_2)_4$—CONH—$CH_2$— or —$(CH_2)_3$—NH—$CH_2$—); or —$(CH_2)_f$—$(CH_2$—$CH_2$—$O)_9$—$(CH_2)_2$— wherein one to three of said —$CH_2$— groups are optionally substituted by a —C(O)NH— or —NHC(O)— group (such as —$(CH_2)_3$—NHCO—$(CH_2CH_2O)_4$—$(CH_2)_2$—NHCO—$CH_2$—, —$(CH_2)_3$—NHCO—$(CH_2)_2$—$(CH_2CH_2O)_4$—NHCO—$CH_2$— or —$(CH_2)_4$—NHCO—$(CH_2)_2$—$(CH_2CH_2O)_4$—NHCO—$CH_2$—).

In a further embodiment, $S_2$ represents a spacer selected from:
—$(CH_2)_e$—, wherein one or two of said —$CH_2$— groups are optionally substituted by a —C(O)NH— or —NHC(O)— group (such as —$(CH_2)_3$—NHCO—$CH_2$—, —$(CH_2)_3$—NHCO—, —$(CH_2)_3$—, —$(CH_2)_3$—NHCO—$(CH_2)_4$—CONH—$CH_2$— or —$(CH_2)_3$—NH—$CH_2$—); or
—$(CH_2)_e$—$(CH_2$—$CH_2$—$O)_g$—$(CH_2)_h$—, wherein one or two of said —$CH_2$— groups are optionally substituted by a —C(O)NH— or —NHC(O)— group (such as —$(CH_2)_3$—NHCO—$(CH_2)_2$—$(CH_2CH_2O)_4$—NHCO—$CH_2$— or —$(CH_2)_4$—NHCO—$(CH_2)_2$—$(CH_2CH_2O)_4$—NHCO—$CH_2$—).

In a further embodiment, $S_2$ represents a spacer selected from —$(CH_2)_e$—, wherein one or two of said —$CH_2$— groups are optionally substituted by a —C(O)NH— or —NHC(O)— group (such as —$(CH_2)_3$—NHCO—$CH_2$—).

In a further embodiment, $S_2$ represents a spacer selected from:
—$(CH_2)_e$—, wherein one or three of said —$CH_2$— groups are optionally substituted by a —NHC(O)— group (such as —$(CH_2)_3$—NHCO—$CH_2$— or —$(CH_2)_3$—NHCO—$(CH_2)_5$—NHCO—$(CH_2)_5$—NHCO—$CH_2$—); or
—$(CH_2)_f$—$(CH_2$—$CH_2$—$O)_g$—$(CH_2)_h$—, wherein two of said —$CH_2$— groups are optionally substituted by a —NHC(O)— group (such as —$(CH_2)_3$—NHCO—$(CH_2CH_2O)_4$—$(CH_2)_2$—NHCO—$CH_2$—).

In one embodiment, $S_2$ represents a spacer selected from —$(CH_2)_e$—, wherein one or three of said —$CH_2$— groups are optionally substituted by a —NHC(O)— group (such as —$(CH_2)_3$—NHCO—$CH_2$— or —$(CH_2)_3$—NHCO—$(CH_2)_5$—NHCO—$(CH_2)_5$—NHCO—$CH_2$—). In an alternative embodiment, $S_2$ represents a spacer selected from —$(CH_2)_f$—$(CH_2$—$CH_2$—$O)_g$—$(CH_2)_h$—, wherein two of said —$CH_2$— groups are optionally substituted by a —NHC(O)— group (such as —$(CH_2)_3$—NHCO—$(CH_2CH_2O)_4$—$(CH_2)_2$—NHCO—$CH_2$—).

In one embodiment, $S_2$ represents a spacer selected from —$(CH_2)_e$—, wherein three of said —$CH_2$— groups are optionally substituted by a —NHC(O)— group (such as —$(CH_2)_3$—NHCO—$(CH_2)_5$—NHCO—$(CH_2)_5$—NHCO—$CH_2$—).

In one embodiment, e represents an integer selected from 1 to 17. In a further embodiment, e represents an integer selected from 1 to 10. In a further embodiment, e represents an integer selected from 4 to 10. In a yet further embodiment, e represents an integer selected from 4, 5 or 10. In a still yet further embodiment, e represents an integer selected from 5 or 17. In a still yet further embodiment, e represents an integer selected from 5. In a still yet further embodiment, e represents an integer selected from 17.

In one embodiment, f represents an integer selected from 1 to 8. In a further embodiment, f represents an integer selected from 2 to 6. In a yet further embodiment, f represents an integer selected from 6. In a yet further embodiment, f represents an integer selected from 4.

In one embodiment, g represents an integer selected from 1 to 5. In a further embodiment, g represents an integer selected from 1 to 4. In a yet further embodiment, g represents an integer selected from 4.

In one embodiment, h represents an integer selected from 1 to 4. In a further embodiment, h represents an integer selected from 1 to 3. In a further embodiment, h represents an integer selected from 1 or 2. In a yet further embodiment, h represents an integer selected from 2. In a yet further embodiment, h represents an integer selected from 4.

In one embodiment, $X_1$ represents —C(O)—.

In one embodiment, $Y_2$ represents —O—.

In one embodiment, m represents an integer selected from 1 to 4. In a further embodiment, m represents an integer selected from 1 to 3. In a yet further embodiment, m represents an integer selected from 1, 2 or 3. In a yet further embodiment, m represents an integer selected from 1 or 3. In a yet further embodiment, m represents an integer selected from 1 or 2. In a yet further embodiment, m represents an integer selected from 1.

In one embodiment, Cy represents phenyl or biphenyl. In a further embodiment, Cy represents biphenyl.

References herein to the term "carbohydrate molecule capable of binding to a human anti-alpha-galactosyl antibody" include sugar (i.e. carbohydrate) moieties capable of binding to an immune response component (i.e. an anti-alpha-galactosyl antibody) of said human and consequently eliciting an immune response in a human. Examples of such carbohydrate molecules include alpha-galactosyl compounds and modified derivatives thereof. Further examples of suitable carbohydrate molecules include the alpha-gal epitopes listed in US 2012/0003251 as being suitable for use in the selective targeting and killing of tumour cells, the epitopes of which are herein incorporated by reference. In one embodiment, F is selected from galactosyl-alpha-1,3-galactosyl-beta-1,4-N-acetylglucosamine, alpha1-3 galactobiose, alpha1-3-beta1-4-galactotriose or galilipentasaccharide.

In one particular embodiment, F has a structure as shown in one of the following formulae:

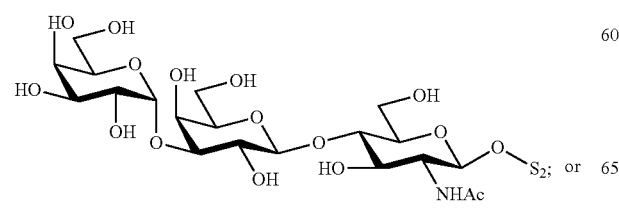; or

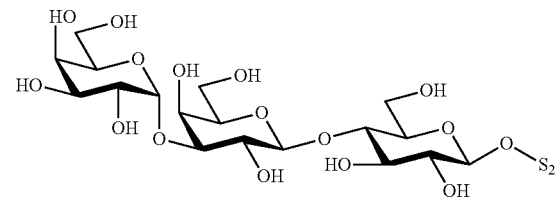

wherein $S_2$ refers to the point of attachment to the $S_2$ group.

In one particular embodiment, F has a structure as shown in the following formula:

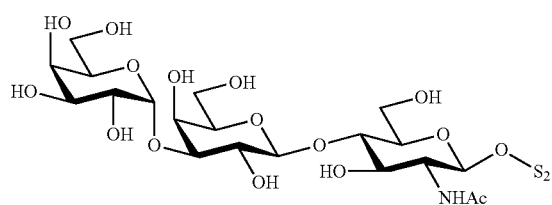

wherein $S_2$ refers to the point of attachment to the $S_2$ group.

References herein to the term "binding moiety" refer to any suitable moiety which is capable of binding to a further component. The invention requires the binding moiety to be a cationic anti-microbial peptide linked to $X_1$ by an amine.

In one embodiment, L represents a lipopeptide. In a further embodiment, the lipopeptide comprises polymyxin or a derivative thereof. Examples of suitable polymyxin and derivatives thereof are described in Velkov et al (2016) Future Med Chem 8(10), 1017-1025, the polymyxins and derivatives thereof are herein incorporated by reference. In one embodiment, the polymyxin or a derivative thereof is selected from Polymyxin B, Polymyxin $B_2$, Polymyxin Nonapeptide, Colistin A, Colistin B, CB-182,204 (Cubist Pharmaceuticals), 5a (Pfizer), 5x (Pfizer), CA 14 (Cantab Anti-Infectives) CA824 (Cantab Anti-Infectives), NAB739 (Northern Antibiotics), NAB741 (Northern Antibiotics), NAB7061 (Northern Antibiotics), 38 (University of Queensland), FADDI-002 (Monash University), FADDI-100 (Monash University), or derivatives thereof. In a further embodiment, the polymyxin is Polymyxin B or derivative which has the following structure:

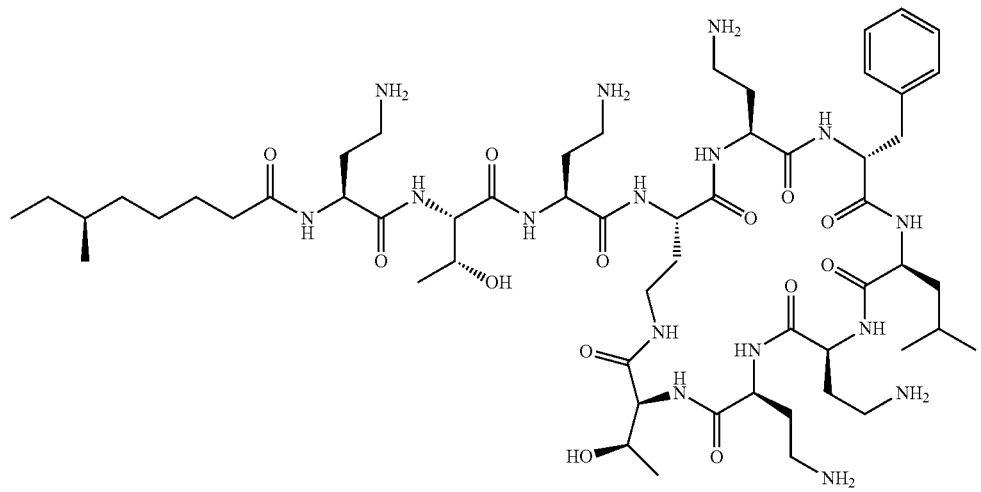
In a yet further embodiment, the Polymyxin B derivative comprises the following structures (where the point of attachment with $X_1$ is shown):
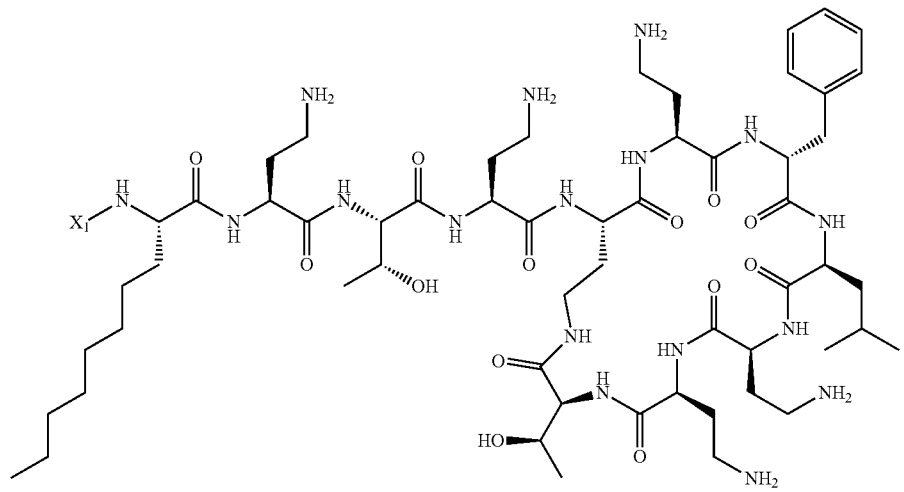
H₂N-[L-OctylGly]-Dab-Thr-Dab-Dab*-Dab-[D-Phe]-Leu-Dab-Dab-Thr*
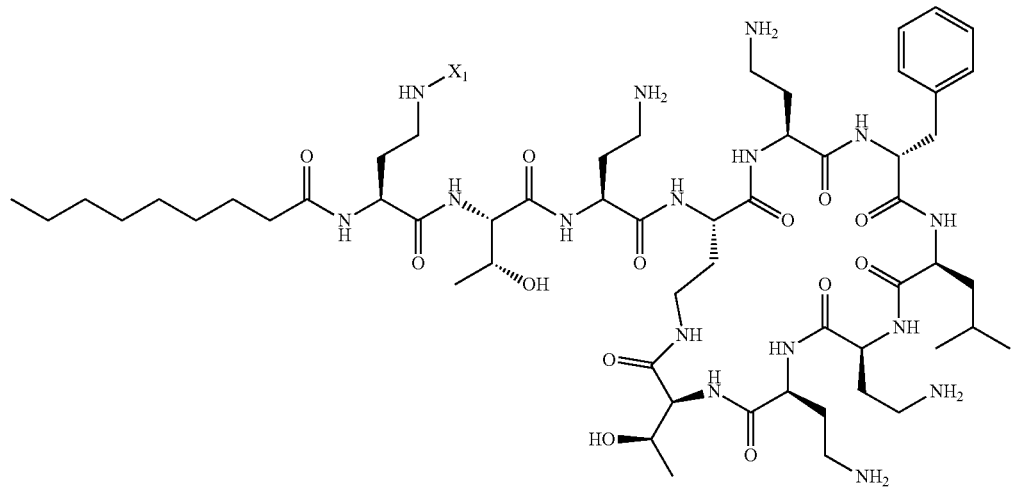
Nonanamide-Dab(NH₂)-Thr-Dab-Dab*-Dab-[D-Phe]-Leu-Dab-Dab-Thr*

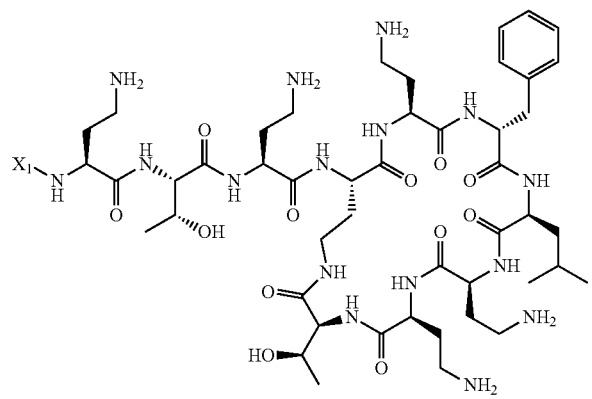
H₂N-Dab-Thr-Dab-Dab*-Dab-[D-Phe]-Leu-Dab-Dab-Thr*
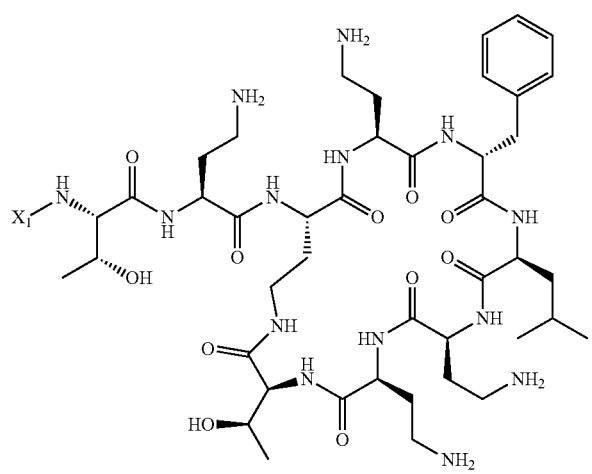
H₂N-Thr-Dab-Dab*-Dab-[D-Phe]-Leu-Dab-Dab-Thr*
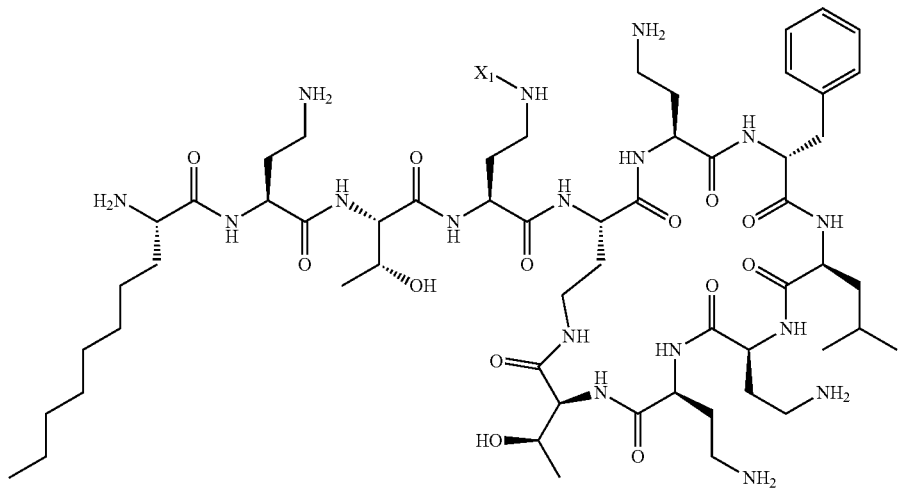
H₂N-[L-OctylGly]-Dab-Thr-Dab(NH₂)-Dab*-Dab-[D-Phe]-Leu-Dab-Dab-Thr*
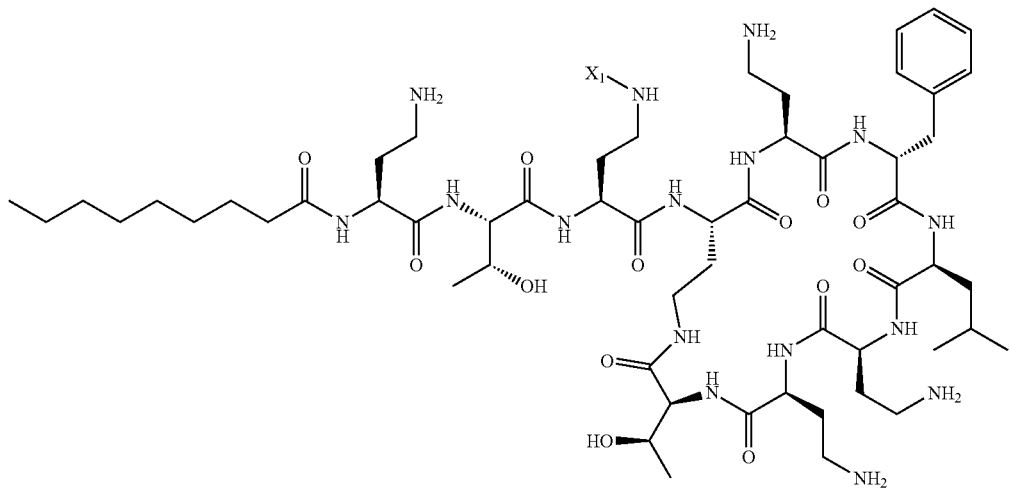
Nonanamide-Dab-Thr-Dab-Dab(NH₂)-Dab*-Dab-[D-Phe]-Leu-Dab-Dab-Thr*

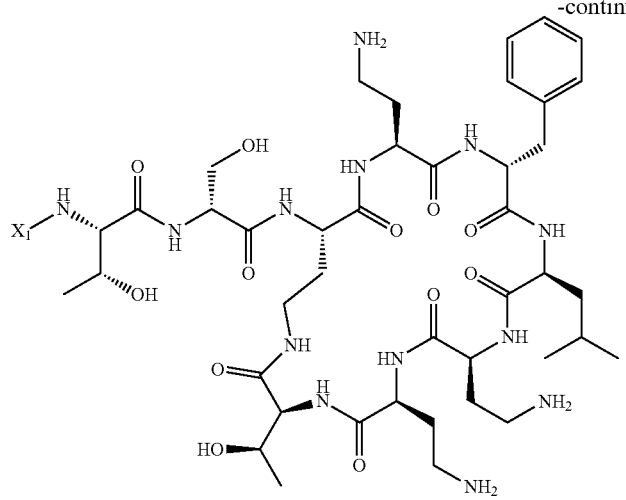

H₂N-Thr-[D-Ser]-Dab*-Dab-[D-Phe]-Leu-Dab-Dab-Thr*

It will be appreciated that the cationic anti-microbial peptides of the present invention will be configured to bind to a specific pathogen or infective agent.

In one embodiment, the invention provides a compound of formula (I) which comprises a compound of Examples 1-25 or a pharmaceutically acceptable salt thereof. In a further embodiment, the invention provides a compound of formula (I) which comprises a compound of Examples 1-14 or a pharmaceutically acceptable salt thereof. In a yet further embodiment, the invention provides a compound of formula (I) which comprises a compound of Examples 1-10 or a pharmaceutically acceptable salt thereof. In a still yet further embodiment, the invention provides a compound of formula (I) which comprises a compound of Examples 4, 6, 9, 17 or 22 or a pharmaceutically acceptable salt thereof. In a still yet further embodiment, the invention provides a compound of formula (I) which comprises a compound of Example 17 or a pharmaceutically acceptable salt thereof.

In one embodiment, the invention provides a compound of formula (I) which comprises a compound of Examples 1-25 or a pharmaceutically acceptable salt thereof. In a further embodiment, the invention provides a compound of formula (I) which is the free base or the trifluoroacetate salt of a compound of Examples 1-14. In a yet further embodiment, the invention provides a compound of formula (I) which is the free base or the trifluoroacetate salt of a compound of Examples 1-10. In a still yet further embodiment, the invention provides a compound of formula (I) which is the free base or the trifluoroacetate salt of a compound of Examples 4, 6, 9, 17 or 22. In a still yet further embodiment, the invention provides a compound of formula (I) which is the free base or the trifluoroacetate salt of a compound of Example 17.

A reference to a compound of formula (I) and sub-groups thereof also includes ionic forms, salts, solvates, isomers (including geometric and stereochemical isomers), tautomers, N-oxides, esters, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, isotopes and protected forms thereof as defined in any aspect of the invention (except intermediate compounds in chemical processes) are referred to as "compounds of the invention".

Compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds.

The salts of the present invention can be synthesized from the parent compound that contains a basic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate salt, also known as a hemisulfate salt.

Where the compounds of formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

Compounds of formula (I) containing an amine function may also form N-oxides. A reference herein to a compound of formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of formula (I) may exist in a number of different geometric isomeric, and tautomeric forms and references to compounds of formula (I) include all such forms. For the avoidance of doubt, where a compound can exist in one of several geometric isomeric or tautomeric forms and only one is specifically described or shown, all others are nevertheless embraced by formula (I).

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^{2}$H (D) and $^{3}$H (T), carbon, such as $^{11}$C $^{13}$C and $^{14}$C, fluorine, such as $^{18}$F, nitrogen, such as $^{13}$N and $^{15}$N, oxygen, such as $^{15}$O, $^{17}$O and $^{18}$O.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$O, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

Methods for the Preparation of Compounds of Formula (I)

In this section, as in all other sections of this application unless the context indicates otherwise, references to formula (I) also include all other sub-groups and examples thereof as defined herein.

The compounds pertaining to the invention described herein may be prepared in a stepwise synthetic sequence as illustrated in the Schemes below. The syntheses involve the preparation of various central constructs (Cy) that enable choice of valency for F and choice of peptide for L within the molecule. Compounds of formula (I) can be prepared in accordance with synthetic methods well known to the skilled person. For example, one skilled in the art will appreciate that the chemical steps and choice of protecting groups may be managed in any order to enable synthetic success.

According to a further aspect of the invention there is provided a process for preparing a compound of formula (I) as hereinbefore defined which comprises:

(a) preparing a compound of formula (I) wherein $Y_1$ represents —CONH— (i.e. a compound of formula (IA)) by reacting a compound of formula (II) with a compound of formula (III) followed by a suitable deprotection step:

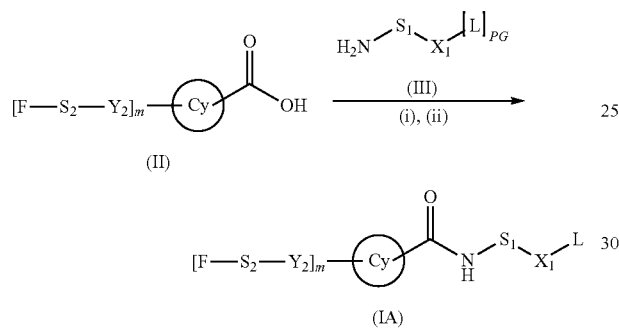

wherein $S_2$, $Y_2$, m, Cy, $S_1$, $X_1$, L and F are as defined hereinbefore and PG is a suitable peptide protecting group such as Dde; or (b) preparing a compound of formula (I) wherein $Y_1$ represents —CONH— and $X_1$ represents —C(O)— (i.e. a compound of formula (IB)) by reacting a compound of formula (IV) with a compound of formula (V) followed by a suitable deprotection step:

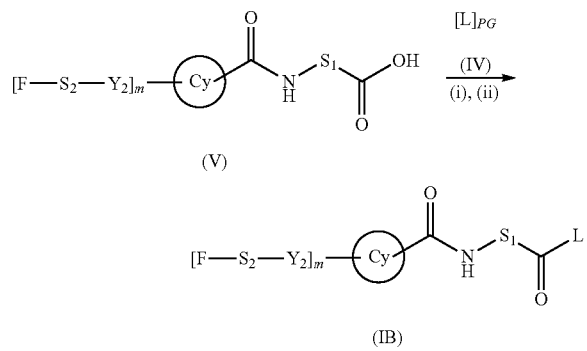

wherein $S_2$, $Y_2$, m, Cy, $S_1$, L and F are as defined hereinbefore and PG is a suitable peptide protecting group such as Dde; or (c) preparing a compound of formula (I) by reacting a compound of formula (VI) with a compound of formula (VII) followed by a suitable deprotection step:

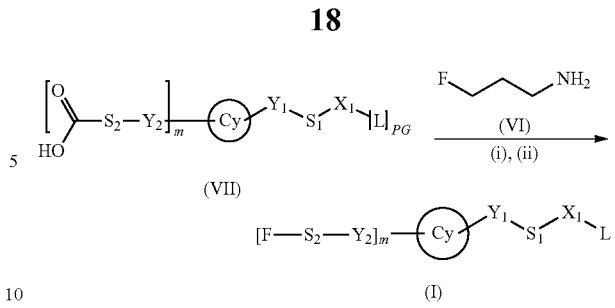

wherein $S_2$, $Y_2$, m, Cy, $S_1$, $X_1$, L and F are as defined hereinbefore, PG is a suitable peptide protecting group such as Dde; or (d) preparing a compound of formula (I) by reacting a compound of formula (XII) with a compound of formula (XIII) followed by a suitable deprotection step, wherein $Y_1$ represents a CONH group:

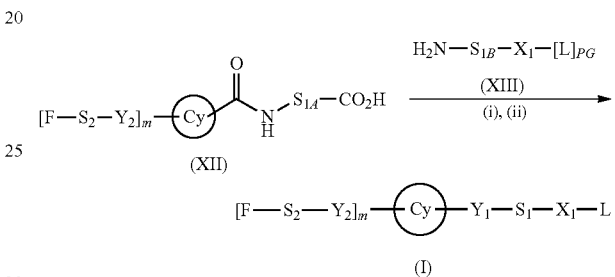

wherein $S_2$, $Y_2$, m, Cy, $X_1$, L and F are as defined hereinbefore, $S_{1A}$ and $S_{1B}$ together form an $S_1$ group and PG is a suitable peptide protecting group such as Dde; or (e) interconversion of a compound of formula (I) or protected derivative thereof to a further compound of formula (I) or protected derivative thereof.

Step (i) in processes (a) to (d) typically comprise an amide bond formation reaction, which typically comprises activation of the carboxylic acid with either phosphate containing reagents, triazine based reagents or carbodiimide containing reagents in the presence of an organic base in an organic solvent. Preferred conditions comprise HATU ((1-[bis(dimethylamino)methylene]-1H-1,2,3-triazolo[4,5-b]pyridinium 3-oxidehexafluorophosphate) with diisopropylethylamine in DMF.

Step (ii) in processes (a) to (d) typically comprise any suitable deprotection reaction, the conditions of which will depend upon the nature of the protecting group. When the protecting group comprises Dde, such a deprotection will typically comprise the use of hydrazine in DMF. When the protecting group comprises Cbz or benzyl, such a deprotection will typically comprise hydrogenation over a suitable catalyst such as palladium on carbon. When the protecting group comprises tertbutoxycarbonyl or tert-butyl, such a deprotection will be acid mediated and will typically comprise TFA in DCM.

Process (e) typically comprises interconversion procedures known by one skilled in the art. For example, in compounds of formula (I), a first substituent may be converted by methods known by one skilled in the art into a second, alternative substituent. A wide range of well known functional group interconversions are known by a person skilled in the art for converting a precursor comound to a compound of formula (I) and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described in processes (a), (b), (c), (d) and (e) are followed or preceded by one or more reactions known to the skilled of the art and are performed in an appropriate order to achieve the requisite substitutions on $S_2$, $Y_2$, m, Cy, $S_1$, $X_1$, $Y_1$, L and F defined above to afford other compounds of formula (I). Non-limiting examples of such reactions whose conditions can be found in the literature include:

protection of reactive functions,
deprotection of reactive functions,
halogenation,
dehalogenation,
dealkylation,
alkylation and arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

Compounds of formula (II) may be prepared according to the methods described in Scheme 1 from compounds of formula (VIII) and (VI) according to process steps (i) and (ii) as described hereinbefore.

Scheme 1

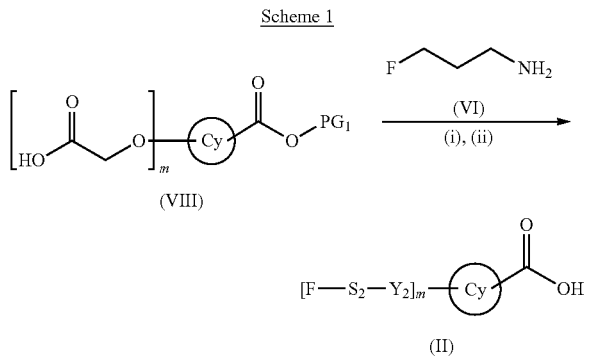

wherein m, Cy, $Y_2$, $S_2$ and F are as defined hereinbefore and $PG_1$ is a protecting group comprising benzyl.

Additionally, compounds of formula (V) may be prepared from compounds of formula (II) according to process steps (i) and (ii) as described hereinbefore with employment of a suitably chosen linker ($S_1$) comprising a suitable protecting group, such as benzyl, which is either commercially available or prepared as described in the literature by one skilled in the art.

Compounds of formula (VII) may be prepared according to the methods described in Scheme 2 from compounds of formula (III) and (IX) according to process steps (i) and (ii) as described hereinbefore.

Scheme 2

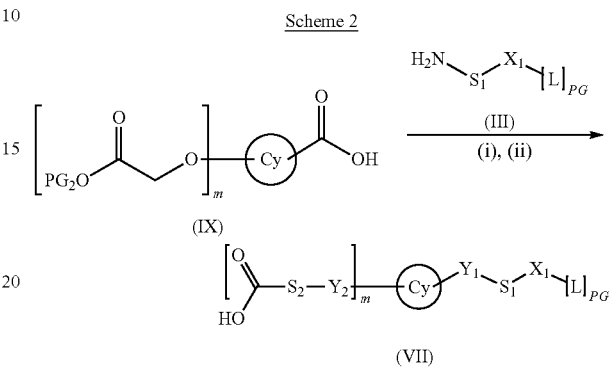

wherein m, Cy, $Y_2$, $S_1$, $S_2$, $X_1$ and F are as defined hereinbefore, $Y_1$ is —CONH—, $PG_2$ is a protecting group comprising tert-butyl and PG is a suitable peptide protecting group such as Dde, Compounds of formula (VIII) may be prepared according to the methods described in Scheme 3 from compounds of formula (X) and (XI) according to process steps (iii) and (ii), an alkylation reaction followed by a deprotection reaction as described hereinbefore, respectively.

Scheme 3

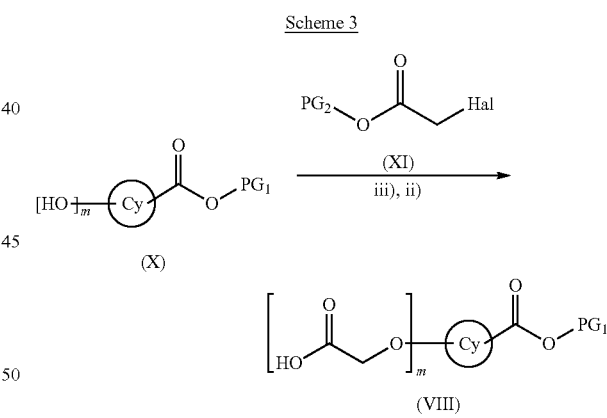

wherein m and Cy are as defined hereinbefore, $PG_2$ is a protecting group comprising tert-butyl, $PG_1$ is a protecting group comprising benzyl and Hal is a halide such as Cl, Br or I.

Step (iii) typically comprises alkylation conditions with compounds of formula (XI) in an inorganic base in a polar organic solvent at room temperature. Preferred conditions comprise potassium carbonate in DMF.

Similarly, compounds of formula (IX) may also be prepared according to Scheme 3 wherein alternative deprotection conditions may be employed. Following the alkylation step, wherein $PG_1$ is benzyl, $PG_1$ may be preferentially deprotected under hydrogenation conditions as previously described hereinbefore.

When Cy is bi-phenyl, compounds of formula (X) may be prepared by employment of a Suzuki reaction to construct the biphenyl unit. Preferred conditions comprise tetrakistriphenyl phosphine palladium (0) with sodium carbonate in dioxane and water at 100° C. When suitable required protecting groups are employed, such as TBS, such protecting groups may be deprotected using a fluoride mediated deprotection. Preferred conditions comprise TBAF in THF at room temperature.

Compounds of formula (XII) and (XIII) wherein $S_1$ contains $S_{1A}$ or $S_{1B}$ may be prepared according to Scheme 1, according to the methods described herein or prepared according to the literature.

Compounds of formula (III), (IV), (VI) and (XI) are either commercially available, prepared according to the methods described herein or prepared according to the literature.

Pharmaceutical Compositions

While it is possible for the compound of formula (I) to be administered alone, it is preferable to present it as a pharmaceutical composition (e.g. formulation).

Thus, according to a further aspect, the invention provides a pharmaceutical composition, and methods of making a pharmaceutical composition comprising (e.g admixing) at least one compound of the invention where L represents a cationic anti-microbial peptide, together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity (i.e. generally recognised as safe (GRAS)), irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the invention can be formulated in accordance with known techniques, see for example, Remington's Pharmaceutical Sciences, Mack Publishing Company, Easton, Pa., USA.

The pharmaceutical compositions can be in any form suitable for parenteral, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a compound of the invention. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various anti-bacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous or subcutaneous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for subcutaneous (s.c.) administration.

The compound of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral or subcutaneous formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. One example of a patient pack includes a prefilled syringe. Such pre-filled syringes already contain the drug substance. The front end portion of a pre-filled syringe to which a needle is to be attached is sealed with a nozzle cap. Prior to injection, the nozzle cap is removed from the front end portion and a needle is attached thereto. A gasket is then slid by pushing a plunger rod toward the front end portion so that the drug is expelled.

Compositions for nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compound of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect.

Therapeutic Uses

According to a further aspect of the invention, there is provided a compound of formula (I) as defined herein for use in therapy.

According to a further aspect of the invention, there is provided a compound of formula (I) as defined herein for use in the treatment of a disease or disorder mediated and/or caused by an infective agent.

According to a further aspect of the invention, there is provided the use of a compound of formula (I) as defined herein in the manufacture of a medicament for use in the treatment of a disease or disorder mediated and/or caused by an infective agent.

According to a further aspect of the invention, there is provided a method of treating a disease or disorder mediated and/or caused by an infective agent which comprises administering to an individual in need thereof a compound of formula (I) as defined herein.

Examples of infective agents include any pathogen such as a bacteria, fungus, parasite or virus. Thus, in one embodiment, the disease or disorder mediated by and/or caused by an infective agent is bacterial infection.

Examples of such as bacterial infection include infection by the following bacteria: *Staphylococcus* sp. such as *Staphylococcus aureus* (including methicillin resistant *Staphylococcus aureus* (MRSA)), *Clostridia* sp (e.g. *Clostridium difficile, Clostridium tetani* and *Clostridium botulinum*), *Enterobacter* species, *Mycobacterium tuberculosis, Shigella* sp. such as *Shigelladysenteriae, Campylobacter* sp. such as *Campylobacterjejuni, Enterococcus* sp. such as *Enterococcus faecalis, Bacillus anthracis, Yersinia pestis, Bordetella pertussis, Streptococcal* species, *Salmonella thyphimurim, Salmonella enterica, Chlamydia* species, *Treponemapallidum, Neisseria gonorrhoeae, Borreliaburgdorferi, Vibrio cholerae, Corynebacterium diphtheriae, Helicobacter pylori*, Gram-negative pathogens, such as *Acinetobacter baumannii, Pseudomonas aeruginosa, Klebsiella pneumoniae,* and *Escherichia coli* (and including strains that are resistant to one or more classes of antibiotics, especially multi-drug resistant (MDR) strains).

The compound of the invention is generally administered to a subject in need of such administration, for example a human or animal patient, preferably a human.

The compound of the invention will typically be administered in amounts that are therapeutically or prophylactically useful and which generally are non-toxic. However, in certain situations (for example in the case of life threatening diseases), the benefits of administering a compound of the invention may outweigh the disadvantages of any toxic effects or side effects, in which case it may be considered desirable to administer a compound of the invention in amounts that are associated with a degree of toxicity.

The compound of the invention may be administered over a prolonged term (i.e. chronic administration) to maintain beneficial therapeutic effects or may be administered for a short period only (i.e. acute administration). Alternatively they may be administered in a continuous manner or in a manner that provides intermittent dosing (e.g. a pulsatile manner).

A typical daily dose of the compound of the invention can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the invention can either be administered on a daily basis or on a repeat basis every 2, or 3, or 4, or 5, or 6, or 7, or 10 or 14, or 21, or 28 days for example. Alternatively, the compound of the invention can be administered by infusion, multiple times per day.

The compound of the invention may be administered in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound of the invention may be administered once or more than once each day. The compound of the invention can be administered continuously (i.e. taken every day without a break for the duration of the treatment regimen). Alternatively, the compound of the invention can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the invention for periods of one hour daily for up to ten days in particular up to five days for one week, and the treatment repeated at a desired interval such as two to four weeks, in particular every three weeks.

More particularly, a patient may be given an infusion of a compound of the invention for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, and in particular a continuous infusion of 24 hours to 72 hours.

Ultimately, however, the quantity of compound of the invention administered and the type of composition used will be commensurate with the nature of the disease or physiological condition being treated and will be at the discretion of the physician.

It will be appreciated that the compound of the invention can be used as a single agent or in combination with other therapeutic agents. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

Where the compound of the invention is administered in combination therapy with one, two, three, four or more other therapeutic agents (preferably one or two, more preferably one), the agents can be administered simultaneously or sequentially. In the latter case, the two or more agents will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and compound of the invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound of the invention and the one or more other therapeutic agent(s) when given as a combination may be determined by the person skilled in the art. Said ratio and the exact dosage and frequency of administration depends on the particular compound of the invention and the other therapeutic agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compound of present invention. A particular weight ratio for the compound of the invention and another therapeutic agent may range from 1/10 to 10/1, more in particular from 1/5 to 5/1, even more in particular from 1/3 to 3/1.

EXAMPLES

The invention will now be illustrated, but not limited, by reference to the specific embodiments described in the following examples. Compounds are named using an automated naming package (ChemDraw) or are as named by the chemical supplier.

The following synthetic procedures are provided for illustration of the methods used; for a given preparation or step the precursor used may not necessarily derive from the individual batch synthesised according to the step in the description given.

Analytical Methods

Wherein examples and preparations cite analytical data, the following analytical methods were used unless otherwise specified:

LCMS

System: LCMS Agilent 1100 (quaternary pump); mass spectrometer: Waters Micromass ZQ Column: XBridge C18 4.6×50 mm, 5 μm.

Solvent: A=water; B=acetonitrile, C=10 mm ammonium formate in water; D=0.05% formic acid in acetonitrile Column temperature: 25° C., injection volume: 5 μL LCMS Method A: 4.5 Minute Acidic Run

| Time (mins) | A (%) | B (%) | C (%) | D (%) | Flow (mL/min) |
|---|---|---|---|---|---|
| 0 | 95 | 0 | 0 | 5 | 2.0 |
| 3.5 | 0 | 95 | 0 | 5 | 2.0 |
| 4.5 | 0 | 95 | 0 | 5 | 2.0 |
| 4.6 | 95 | 0 | 0 | 5 | 2.0 |

LCMS Method B: 4.5 Minute Buffered Run

| Time (mins) | A (%) | B (%) | C (%) | D (%) | Flow (mL/min) |
|---|---|---|---|---|---|
| 0 | 0 | 5 | 95 | 0 | 2.0 |
| 3.5 | 0 | 95 | 5 | 0 | 2.0 |
| 4.5 | 0 | 95 | 5 | 0 | 2.0 |
| 4.6 | 0 | 5 | 95 | 0 | 2.0 |

NMR

NMR details were recorded on an Oxford Instruments AS400.

MS

Wherein MS data is reported, for large molecular weight compounds a mass-to-charge ratio (m/z) is typically observed.

Abbreviations

Wherein the following abbreviations have been used, the following meanings apply:

Ahx is aminohexyl;
Alloc is allyloxycarbonyl;
aq. is aqueous;
Boc is tert-butyloxycarbonyl;
br s is broad singlet;
$CDCl_3$ is deuterochloroform;
CTC resin is chlorotrityl chloride resin;
d is doublet;
Dab is 2,4-diaminobutyric acid;
DCM is dichloromethane;
Dde is (1,(4,4-dimethyl-2,6-dioxocyclohex-1-ylidene)-3-ethyl);
DIPEA is diisopropylethylamine;
DMF is dimethylformamide;
DMSO is dimethylsulfoxide;
$d_6$-DMSO is deuterated DMSO;
ES is electrospray ionisation technique;
EtOAc is ethyl acetate;
Fmoc is 9-fluorenylmethoxycarbonyl;
g is gram;
Gly is glycine;
HATU is O-(7-azabenzotriazol-1-yl)-N,N,N',N'-tetramethyluronium hexafluorophosphate;
HBTU is O-(benzotriazol-1-yl)-N,N,N',N'-tetramethyluronium hexafluorophosphate;
HCl is hydrochloric acid;
HOBt is hydroxybenzotriazole;
HPLC is high performance liquid chromatography;
$KHCO_3$ is potassium hydrogen carbonate;
L is litre;
LCMS is liquid chromatography mass spectrometry;
Leu is leucine;
m is multiplet;
mg is milligram;
M is molar;
MeCN is acetonitrile;
MeOH is methanol;
$MgSO_4$ is magnesium sulfate;
MHz is megaHertz;
mL is millilitre;
mmol is millimole;
MS is mass spectrometry;
$NaHCO_3$ is sodium hydrogen carbonate;
NaOH is sodium hydroxide;
$NH_3$ is ammonia;
NMR is nuclear magnetic resonance;
Pd/C is palladium on carbon;
$Pd(PPh_3)_4$ is tetrakis(triphenylphosphine)palladium(0);
$Pd(PPh_3)_2Cl_2$ is palladium(II)bis(triphenylphosphine)dichloride
Phe is phenylalanine;
$PhSiH_3$ is phenylsilane;
Psi is pounds per square inch;
Rt is retention time;
s is singlet;
t is triplet;
TBTU is O-(benzotriazol-1-yl)-N,N,N',N'-tetramethyluronium tetrafluoroborate;
TEA is triethylamine;
Thr is threonine;

TIS is triisopropylsilane;

TFA is trifluoroacetic acid;

μL is microlitre and v is volume.

Wherein alpha-Gal is referred to, the following intermediate applies:

3-(((2R,3R,4R,5S,6R)-3-acetamido-5-((((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amine

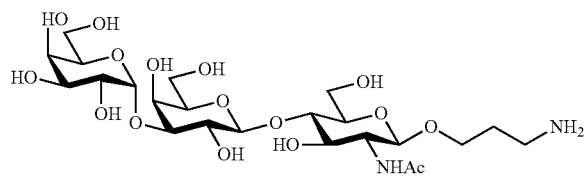

This intermediate may be prepared according to the methods described by Bovin et al (Mendeleev Communications (2002), (4), 143-145).

Synthesis of Peptide Intermediates

PM B scaffolds were constructed according to standard Solid Phase Peptide Synthesis (SPPS) using appropriately protected amino acids and CTC resin. Either Fmoc-Dab(Dde)-CTC resin, Fmoc-Thr(OtBu)-CTC resin or Fmoc-Leu-CTC resin were chosen as suitable starting points, and the scaffolds were cyclised at an appropriate place in the synthesis. All protected aminoacids and linker starting materials are commercially available or prepared according to the references cited herein.

Using SPPS, three alternative Polymyxin scaffold strategies were employed:

Method 1: wherein the Polymyxin scaffold is synthesised with no linker

Method 2: wherein the Polymyxin scaffold is synthesised with addition of a linker in solution phase following cleavage from the resin Method 3: wherein the Polymyxin scaffold is synthesised with addition of a linker as an extra on-resin step Protected amino acids were chosen from: Fmoc-Leu-OH, Fmoc-[D-Phe]-OH, Fmoc-Dab(Dde)-OH, Fmoc-Dab(Alloc)-OH, Fmoc-Thr-(OtBu)-OH, Fmoc-[D-Ser(OtBu)]—OH and Boc-Dab(Dde)-OH.

Linker starting materials were chosen from either Boc-PEG$_8$-OH, Boc-Ahx-Ahx-OH (WO2008123844), Boc-[L-OctylGly]-OH, Fmoc-[L-OctylGly]-OH or combinations thereof.

Additionally, some peptide scaffolds were terminated with nonanoic acid.

The peptide scaffolds were analysed using HPLC: Agilent 1260 LCMS: Agilent 1200+6410 MS.

Preparation 1

H$_2$N-Dab(Dde)-Thr(OH)-Dab(Dde)-Dab*-Dab(Dde)-[D-Phe]-Leu-Dab(Dde)-Dab(Dde)-Thr(OH)*

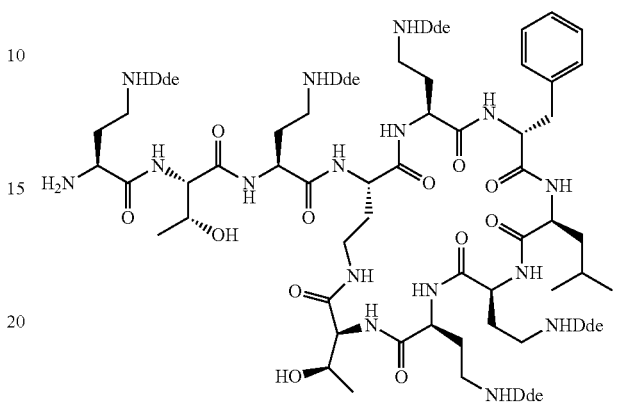

Method 1

The peptide chain was elongated on CTC resin commencing with Fmoc-Leu-OH [to CTC resin (1 mmol, 1 g, 1.0 mmol/g) and Fmoc-Leu-OH (0.353 g, 1.0 mmol, 1.0 eq) in DCM (10.00 mL) was added DIPEA (4.0 eq) and the reaction was mixed for 2 hours. MeOH (1.0 mL) was added and the reaction was capped and mixed for 30 minutes]. 20% piperidine in DMF was used for de-blocking, and the desired amino acid sequence was constructed using HBTU and DIPEA in DMF for all residues except for Fmoc-Dab(Alloc)-OH which was coupled using HATU and DIPEA in DMF to afford Boc-Dab(Dde)-Thr(OtBu)-Dab(Dde)-Dab(Alloc)-Dab(Dde)-[D-Phe]-Leu-O-CTC-resin. At this point the resin was treated with Pd(PPh$_3$)$_2$Cl$_2$ (0.1 eq) and PhSiH$_3$ (10 eq) in DCM followed by resin washing with DMF and MeOH to effect alloc deprotection. The peptide was then further elongated as above with the required remaining amino acids. The peptide was cleaved from the resin with 1% TFA in DCM for 2 minutes and adjusted to pH=7 with DIPEA in DCM. TBTU (2eq) and HOBt (2 eq) were then added and the reaction was stirred for 1 hour to effect cyclisation. The reaction was washed with 5% aqueous HCl and concentrated in vacuo to afford Boc-Dab(Dde)-Thr(OtBu)-Dab(Dde)-Dab*-Dab(Dde)-[D-Phe]-Leu-Dab(Dde)-Dab(Dde)-Thr(OtBu)*. The crude peptide was treated with TFA/water (95% TFA, 5% water, 20 mL) and stirred at room temperature for 2 hours. The reaction was treated with cold isopropyl ether and centrifuged three times. The residue was dried under vacuum and purified using reverse phase column chromatography (HPLC:Mobile Phase: A: 0.1% TFA in H$_2$O, B:0.1% TFA in MeCN; Flow: 1.0 mL/min T=50° C.; Column: YMC-Pack ODS-A 150*4.6 mm, 5 μm; Instrument: Agilent 1200 HPLC (5-521) followed by lyophilisation to afford the title compound (80 mg).

The intermediate was taken directly on to the next step.

Preparation 2

H₂N-Dab-Thr(OH)-Dab-Dab*-Dab-[D-Phe]-Leu-Dab-Dab-Thr(OH)*    5

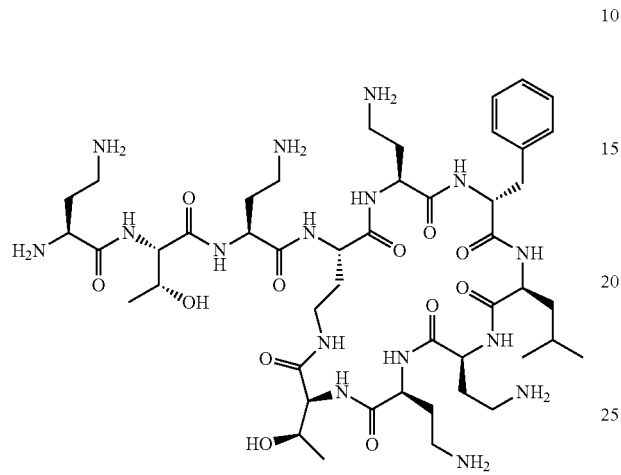

Following global deprotection of the Dde protecting groups from Preparation 1 (3% hydrazine/MeOH), the following data was obtained:

Rt=14.23 minutes, ES+MS m/z 1063.4 [M+1] and 532.2 [M+2]/2; theoretical mass: 1062.6.

Preparation 3

H₂N-L-octylGly-Dab(Dde)-Thr(OH)-Dab(Dde)-Dab*-Dab(Dde)-[D-Phe]-Leu-Dab(Dde)-Dab(Dde)-Thr(OH)*    40

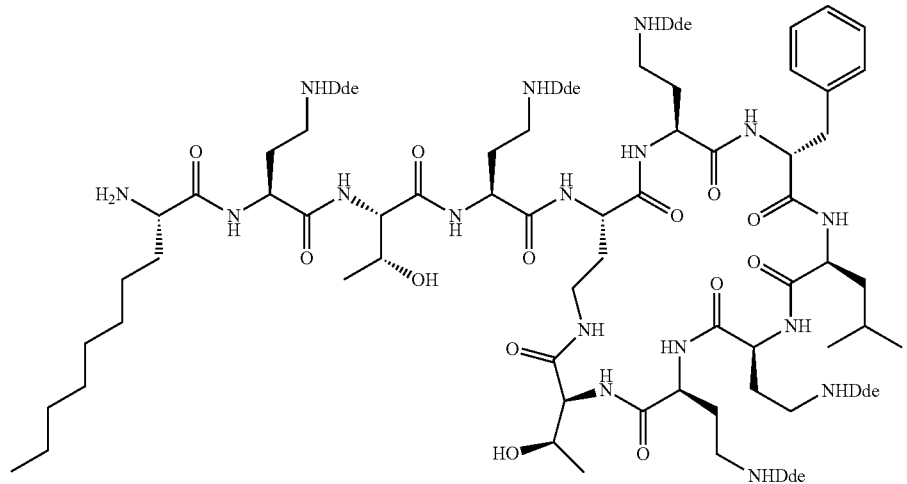

The title compound may be prepared according to Method 1 using either Fmoc-Dab(Dde)-CTC resin or Fmoc-Leu-CTC resin as starting points together with Boc-[L-octylGly]-OH. The intermediate was taken directly on to the next step.

Preparation 4

Nonanamide-Dab(NH$_2$)-Thr(OH)-Dab(Dde)-Dab*-Dab(Dde)-[D-Phe]-Leu-Dab(Dde)-Dab(Dde)-Thr(OH)*

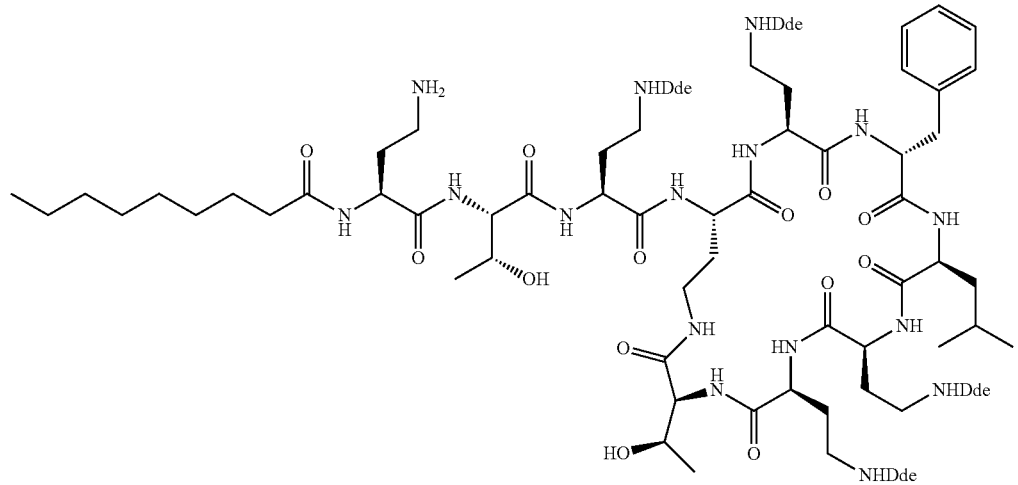

The title compound was prepared according to Method 1 using Fmoc-Dab(Dde)-CTC resin or Fmoc-Leu-CTC resin as starting points together with nonanoic acid.

The intermediate was taken directly on to the next step.

Preparation 5

Nonanamide-Dab(Dde)-Thr(OH)-Dab(PEG$_8$NH$_2$)-Dab*-Dab(Dde)-[D-Phe]-Leu-Dab(Dde)-Dab(Dde)-Thr(OH)*

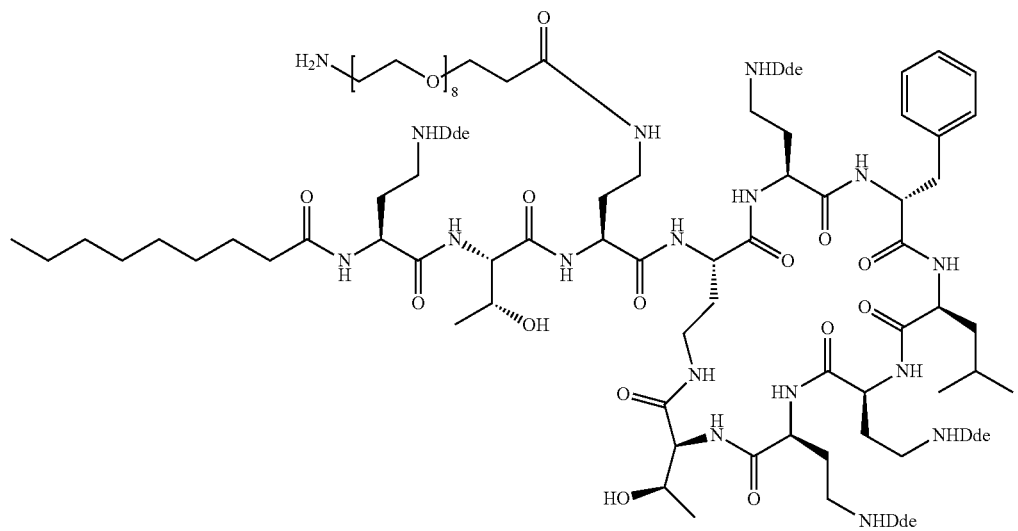

Method 2

The peptide chain was elongated on CTC resin commencing with Fmoc-Thr(OtBu)-OH [to CTC Resin (0.5 mmol, 0.5 g, 1.0 mmol/g) and Fmoc-Thr(OtBu)-OH (200 mg, 0.5 mmol, 1.0 eq) in DCM (5.0 mL), was added DIPEA (4.0 eq) and the reaction was mixed for 2 hours. MeOH (0.5 mL) was added and the reaction was capped and mixed for 30 minutes]. 20% piperidine in DMF was used for de-blocking and the desired amino acid sequence was constructed using HATU (2.85 eq) and DIPEA (6.0 eq) in DMF (2.0 mL) to afford nonanamide-Dab(Dde)-Thr(OtBu)-Dab(Boc)-Dab(Alloc)-Dab(Dde)-[D-Phe]-Leu-Dab(Dde)-O-CTC-resin. At this point the resin was treated with Pd(PPh$_3$)$_2$Cl$_2$ (0.1 eq) and PhSiH$_3$ (10 eq) in DCM followed by resin washing with DMF and MeOH to effect alloc deprotection and dried under nitrogen overnight. The peptide was further elongated as above with the required remaining amino acids. The peptide was cleaved from the resin with 1% TFA/DCM (2×5 mL) for 2 minutes and adjusted to pH=7 with DI PEA in DCM. TBTU (2 eq) and HOBt (2 eq) were added followed by DIPEA (2 eq), and the mixture was stirred for 1 hour to effect cyclisation. The reaction was washed with 5% aqueous HCl and concentrated in vacuo to afford Nonanamide-Dab(Dde)-Thr(OH)-Dab(Boc)-Dab*-Dab(Dde)-[D-Phe]-

Leu-Dab(Dde)-Dab(Dde)-Thr(OH)*. The crude peptide was treated with 95% TFA/2.5% H₂O/2.5% TIS (5 mL) at room temperature and stirred for 30 minutes. The reaction was precipitated with cold isopropyl ether (50 mL) and centrifuged (3 min at 3000 rpm). The crude peptide was washed with isopropyl ether (2×50 mL), centrifuged, and purified using Preparative HPLC (Mobile phase A: 0.1% TFA in H₂O, B: H₂O) followed by lyophilisation to afford the scaffold without the linker.

To a solution of the peptide in DCM, was added Boc-PEG₈-OH (1.2 eq) and HBTU (1.2 eq) followed by DIPEA (2 eq) and the reaction was stirred for 30 minutes at room temperature.

The reaction was washed with 5% HCl (aq) twice, and concentrated in vacuo. The residue was treated with 20% TFA/DCM for 20 minutes and concentrated in vacuo. The residue was purified using preparative HPLC (Mobile phase A: 0.1% TFA in H₂O, B: H₂O) and lyophilised to afford the title compound.

ES⁺ MS m/z 1142.6 [M+2]/2 and 762.1 [M+3]/3; theoretical mass: 2283.8

Preparation 6

H₂N-PEG₈-[L-octylGly]-Dab(Dde)-Thr(OH)-Dab(Dde)-Dab*-Dab(Dde)-[D-Phe]-Leu-Dab(Dde)-Dab(Dde)-Thr(OH)*

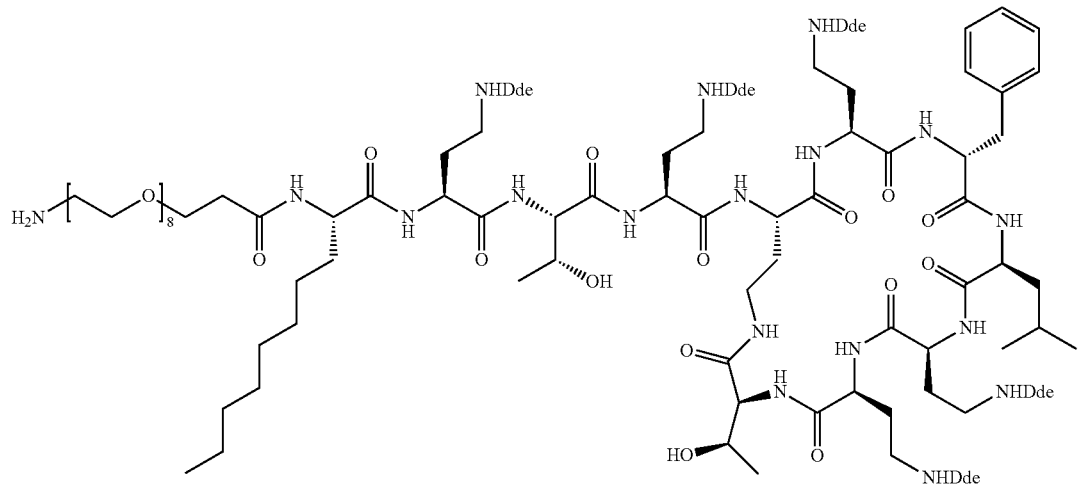

Method 3

The peptide chain was elongated on CTC resin commencing with Fmoc-Dab(Dde)-OH [to CTC Resin (2 mmol, 2 g, 1.0 mmol/g) and Fmoc-Dab(Dde)-OH (1.08 g, 2 mmol, 1.0 eq) in DCM (30 mL), was added DIPEA (4.0 eq) and the reaction was mixed for 2 hours. MeOH (2 mL) was added and the reaction was capped and mixed for 30 minutes]. 20% piperidine in DMF was used for de-blocking and the desired amino acid sequence was constructed using HATU (2.85 eq) and DIPEA (6.0 eq) in DMF (10 mL) to afford Boc(PEG₈)-[L-octylGly]-Dab(Dde)-Thr(OtBu)-Dab(Dde)-Dab(Alloc)-Dab(Dde)-[D-Phe]-Leu-Dab(Dde)-O-CTC-resin. At this point the resin was treated with Pd(PPh₃)₂Cl₂ (0.1 eq) and PhSiH₃ (10 eq) in DCM followed by resin washing with DMF and MeOH to effect alloc deprotection and dried under nitrogen overnight. The peptide was further elongated as above with the required remaining amino acids. The peptide was treated with 1% TFA/DCM (2×20 mL) for 2 minutes and adjusted to pH=7 with DIPEA and diluted with DCM. TBTU (2 eq) and HOBt (2 eq) were added followed by DIPEA (2 eq), and the mixture was stirred for 1 hour to effect cyclisation. The reaction was washed with 5% aqueous HCl and concentrated in vacuo to afford Boc(PEG$_8$)-[L-octylGly]-Dab(Dde)-Thr(OH)-Dab(Dde)-Dab*-Dab(Dde)-[D-Phe]-Leu-Dab(Dde)-Dab(Dde)-Thr(OH)*.

The crude peptide was treated with 95% TFA/2.5% H$_2$O/2.5% TIS (5 mL) at room temperature and stirred for 30 minutes. The reaction was precipitated with cold isopropyl ether (300 mL) and centrifuged (3 min at 3000 rpm). The crude peptide was washed with isopropyl ether (2×100 mL), centrifuged, and purified using Preparative HPLC (Mobile phase A: 0.1% TFA in H$_2$O, B: H$_2$) followed by lyophilisation to afford the title compound.

Rt=10.6-11.9 minutes, ES$^+$ MS m/z 1239.2 [M+2]/2 and 826.4 [M+3]/3; theoretical mass: 2477.0

Preparation 7

Nonanamide-Dab(Ahx-Ahx-NH$_2$)-Thr(OH)-Dab(Dde)-Dab*-Dab(Dde)-[D-Phe]-Leu-Dab(Dde)-Dab(Dde)-Thr(OH)*

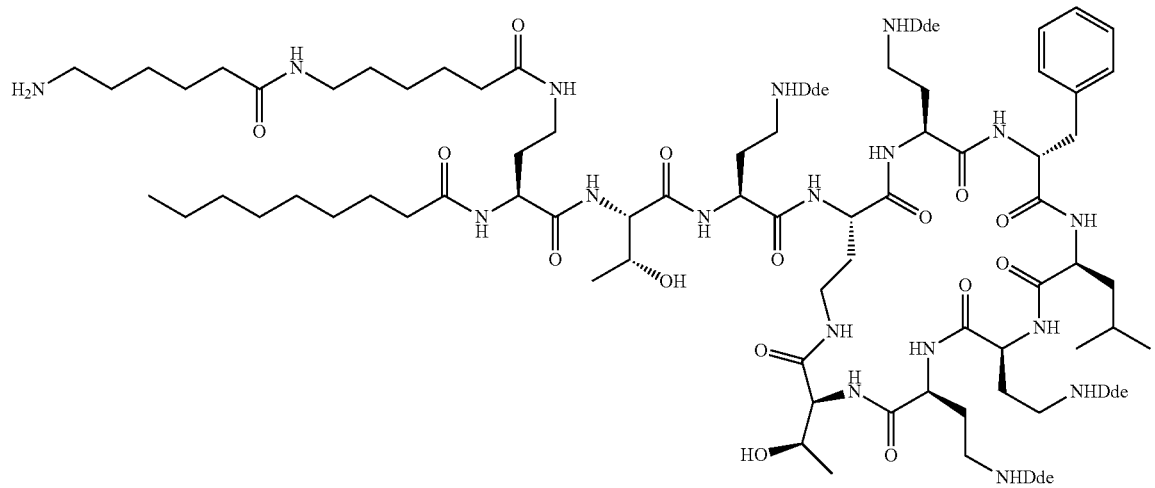

The title compound may be prepared according to Method 2 using Fmoc-Dab(Dde)-CTC resin as a starting point together with nonanoic acid and Boc-Ahx-Ahx-OH.

Rt=8.2-9.3 minutes, ES$^+$ MS m/z 1043.7 [M+2]/2 and 696.3 [M+3]/3; theoretical mass: 2086.6

Preparation 8

H₂N-Ahx-Ahx-[L-octylGly]-Dab(Dde)-Thr(OH)-
Dab(Dde)-Dab*-Dab(Dde)-[D-Phe]-Leu-Dab(Dde)-
Dab(Dde)-Thr(OH)*

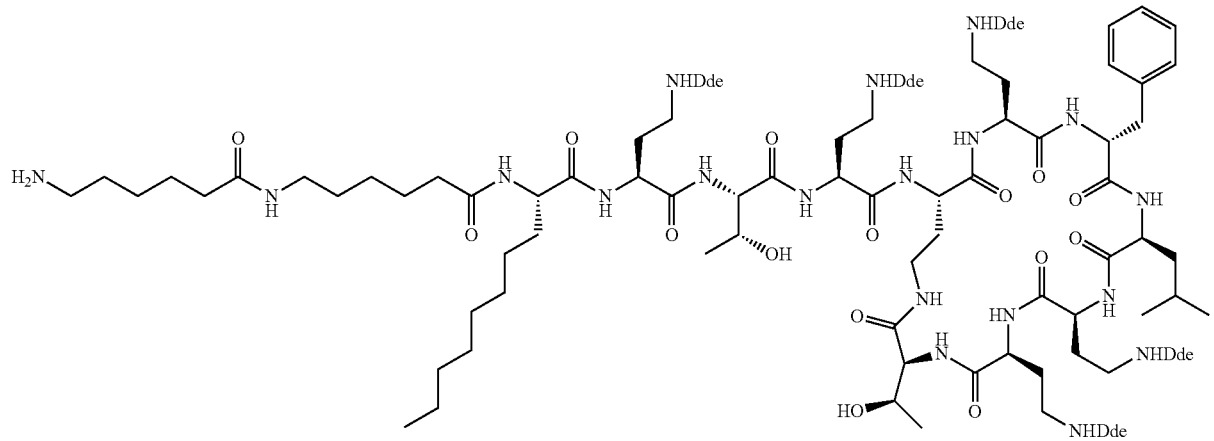

The title compound may be prepared according to Method 3 using Fmoc-Dab(Dde)-CTC resin as a starting point together with Boc-Ahx-Ahx-OH and Fmoc-[L-octylGly]-OH.

Rt=11.9-12.9 minutes, ES⁺ MS m/z 1140.2 [M+2]/2 and 760.7 [M+3]/3; theoretical mass: 2279.9

Preparation 9

Fmoc-[L-octylGly]-Dab(Dde)-Thr(OH)-Dab
(PEG₈H₂)-Dab*-Dab(Dde)-[D-Phe]-Leu-Dab(Dde)-
Dab(Dde)-Thr(OH)*

;1

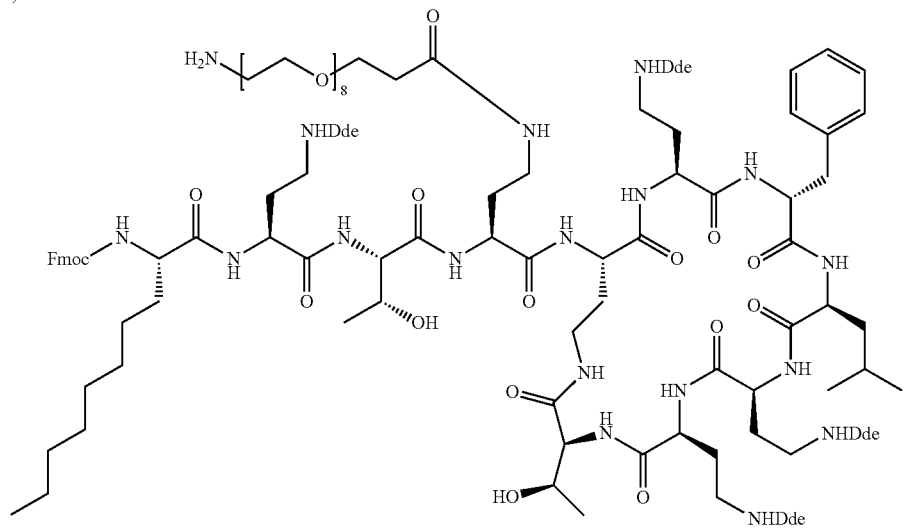

The title compound may be prepared according to Method 2 using Fmoc-Thr(OtBu)-CTC resin as a starting point together with Boc-PEG₈-OH and Fmoc-[L-octylGly]-OH.

The intermediate was taken on directly to the next step.

Preparation 10

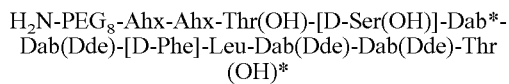

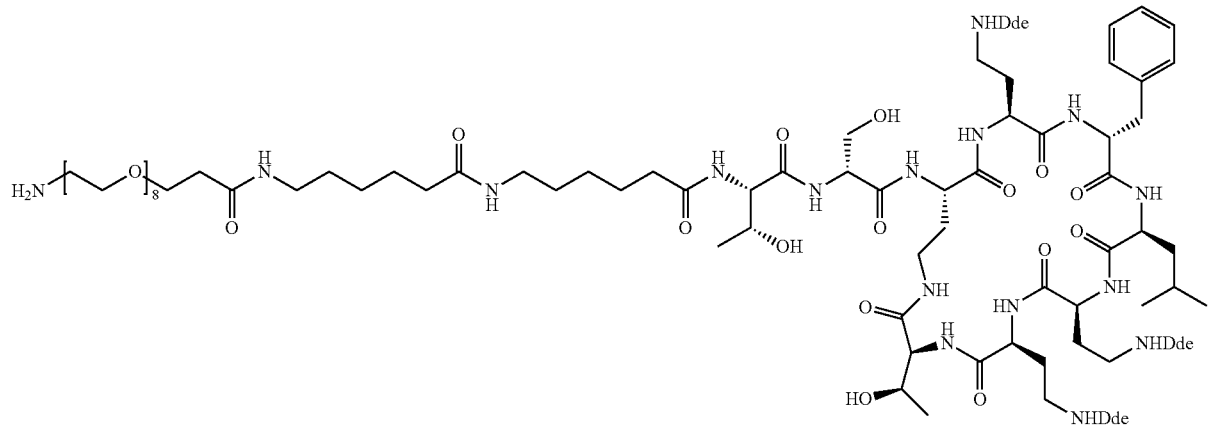

The title compound may be prepared according to Method 2 using Fmoc-Dab(Dde)-CTC resin as a starting point together with Boc-PEG$_8$-OH and Boc-Ahx-Ahx-OH.
The intermediate was taken on directly to the next step.

Preparation 11

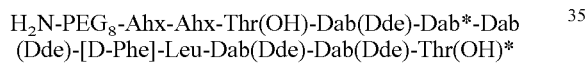

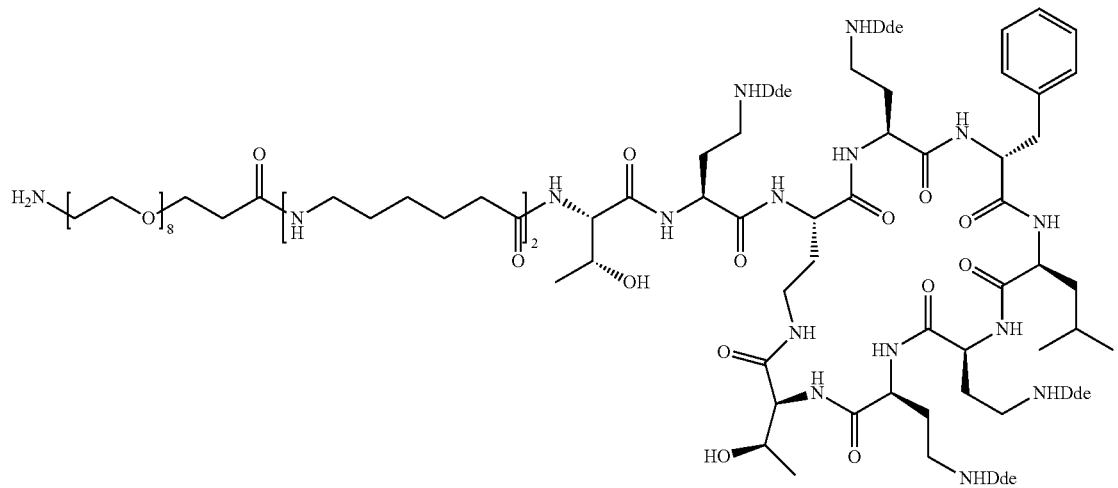

The title compound may be prepared according to Method 2 using Fmoc-Dab(Dde)-CTC resin as a starting point together with Boc-PEG$_8$-OH and Boc-Ahx-Ahx-OH.
The intermediate was taken on directly to the next step.

Preparation 12

H₂N-Ahx-Ahx-Thr(OH)-[D-Ser(OH)]-Dab*-Dab(Dde)-[D-Phe]-Leu-Dab(Dde)-Dab(Dde)-Thr(OH)*

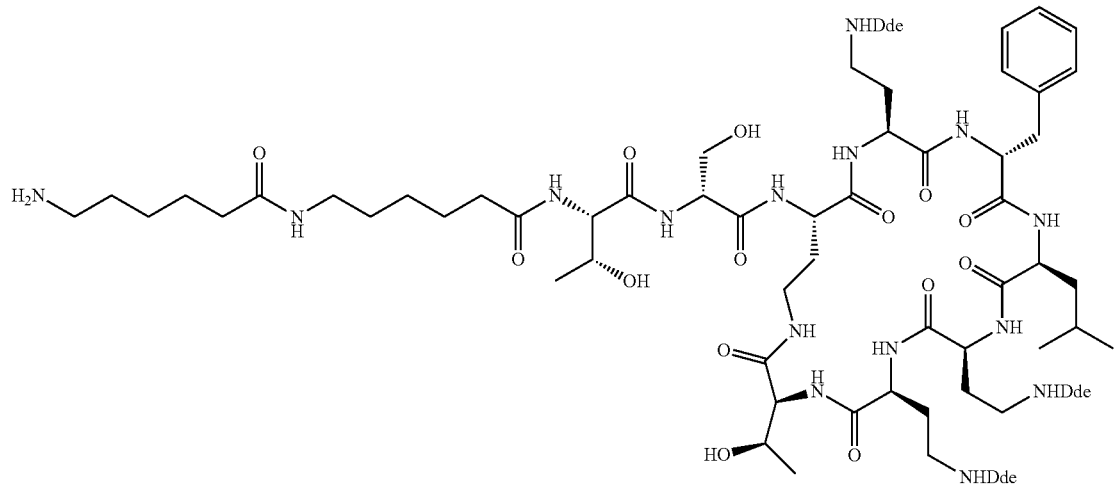

The title compound may be prepared according to Method 3 using Fmoc-Dab(Dde)-CTC resin as a starting point together with Boc-Ahx-Ahx-OH.

The intermediate was taken on directly to the next step.

Preparation 13

H₂N-Ahx-Ahx-Thr(OH)-Dab(Dde)-Dab*-Dab(Dde)-[D-Phe]-Leu-Dab(Dde)-Dab(Dde)-Thr(OH)*

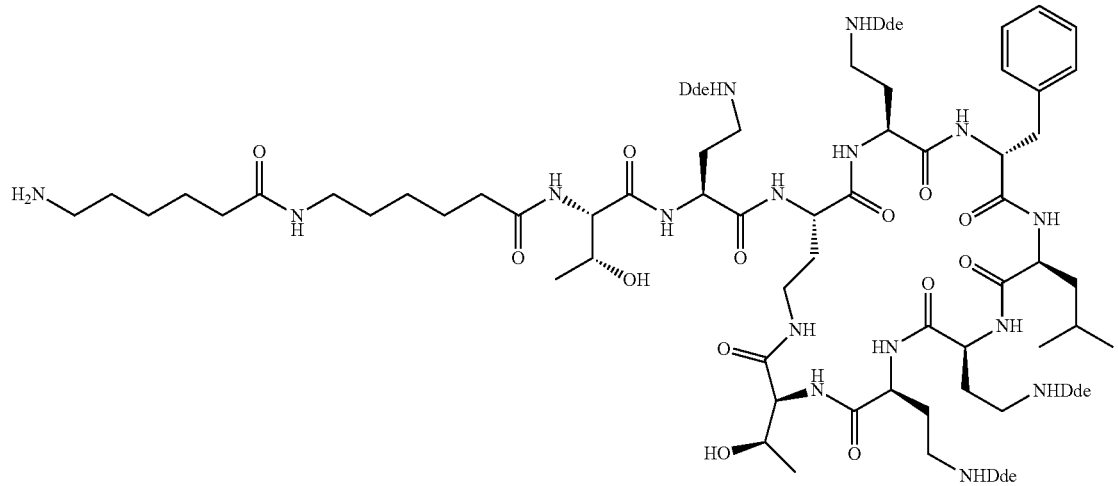

The title compound may be prepared according to Method 3 using Fmoc-Dab(Dde)-CTC resin as a starting point together with Boc-Ahx-Ahx-OH.

The intermediate was taken on directly to the next step.

Synthesis of Alpha-Gal Intermediates

Preparation 14

6-(6-(4'-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-ylcarboxamido)hexanamido)hexanoic Acid

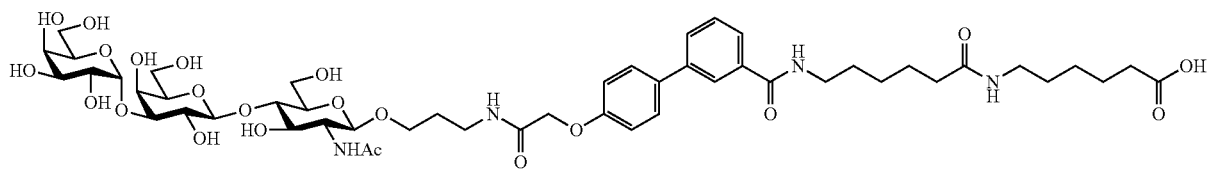

To a solution of Preparation 15 (30 mg, 0.035 mmol) and benzyl 6-(6-aminohexanamido)hexanoate (JACS 136 (52) 18034-18043 (2014), 14.1 mg, 0.042 mmol) in DMF (600 µL) was added triethylamine (17 µL, 0.123 mmol) followed by HATU (16 mg, 0.042 mmol). The reaction was stirred at room temperature overnight. The reaction was concentrated in vacuo, dissolved in DMSO and purified using reverse phase column chromatography eluting with 7-60% MeCN/water with 0.1% ammonia to afford the desired benzyl protected intermediate (19.8 mg, 48%).

LCMS (Method B) Rt=2.45 minutes; ES$^+$ MS m/z 1173.9 [M+H]$^+$

The isolated intermediate was dissolved in MeOH/water (1:1 v/v, 10 mL) and Pd/C (10%, 10 mg) was added. The reaction was placed under an atmosphere of hydrogen (50 psi) and stirred for 3 hours at room temperature. The catalyst was removed by filtration through a syringe filter and the solvent removed under reduced pressure to afford the title compound as a colourless solid (20.4 mg, >99%).

LCMS (Method B) Rt=1.70 minutes; ES$^-$ MS m/z 1081.8 [M–H]$^-$

Preparation 15

4'-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic Acid

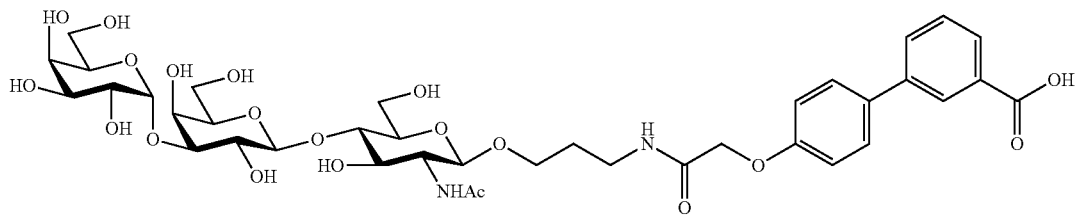

To 2-((3'-((benzyloxy)carbonyl)-[1,1'-biphenyl]-4-yl)oxy)acetic acid (Preparation 16, 55 mg, 152 µmol) in DMF (7.5 mL) was added TEA (63.4 µL, 455 µmol) followed by a solution of alpha-Gal (119 mg, 197 µmol) in DMSO (500 µL). HATU (86.6 mg, 228 µmol) was added as a solution in DMF (500 µL), and the reaction was left to stir for 16 hours under nitrogen at room temperature. The solvent was removed in vacuo and the residue purified using reverse phase column chromatography eluting with 7-60% MeCN/water with 0.1% NH$_3$ to afford the desired benzyl protected intermediate as a colourless solid (93.5 mg, 65%).

LCMS (Method B) Rt=2.54 minutes, ES$^+$ MS m/z 947.6 [M+H]$^+$

The isolated intermediate was dissolved in MeOH/water (1:1 v/v, 5 mL), and to the solution was added Pd/C (10%, 10 mg). The reaction was placed under an atmosphere of hydrogen (50 psi) and stirred for 3 hours at room temperature. The catalyst was removed by filtration through a syringe filter and the solvent removed in vacuo. The residue was purified using reverse phase column chromatography eluting with 5-40% MeCN/water with 0.1% NH$_3$ to afford the title compound as a colourless solid (71.6 mg, 84%).

LCMS (Method A) Rt=1.83 minutes, ES$^+$ MS m/z 857.6 [M+H]$^+$

Preparation 16

2-((3'-((Benzyloxy)carbonyl)-[1,1'-biphenyl]-4-yl)oxy)acetic Acid

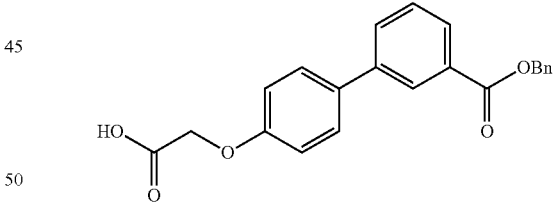

A solution of benzyl 4'-(2-(tert-butoxy)-2-oxoethoxy)-[1,1'-biphenyl]-3-carboxylate (Preparation 17, 7.80 g, 18.6 mmol) in DCM/TFA/water (10:10:1 v/v/v, 80 mL) was stirred for 2 hours at room temperature. The reaction was concentrated in vacuo, azeotroped with dioxane/toluene (1:1, v/v, 80 mL), triturated with toluene, filtered and dried in a vacuum oven to afford the title compound as a colourless solid (6.11 g. 90%).

LCMS (Method B) Rt=2.43 minutes, ES+ MS m/z 363.2 [M+H]+

$^1$H NMR (400 MHz, d$_6$-DMSO): δ ppm 13.00 (1H, s), 8.15 (1H, t), 7.95-7.90 (2H, m), 7.65-7.55 (3H, m), 7.50-7.45 (2H, m), 7.45-7.30 (3H, m) 7.05-7.00 (2H, m), 5.40 (2H, s), 4.70 (2H, s).

Preparation 17

Benzyl 4'-(2-(tert-butoxy)-2-oxoethoxy)-[1,1'-biphenyl]-3-carboxylate

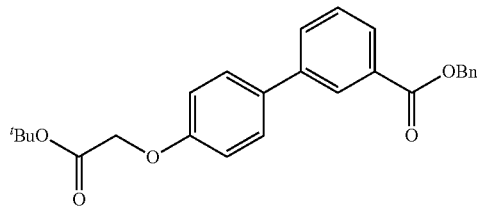 [SMILES: CC(C)(C)OC(=O)COc1ccc(-c2cccc(C(=O)OCc3ccccc3)c2)cc1]

To benzyl 4'-hydroxy-[1,1'-biphenyl]-3-carboxylate (Preparation 18, 15 g, 49.3 mmol) dissolved in DMF (150 mL) was added tert-butyl bromoacetate (10.9 mL, 73.9 mmol) and potassium carbonate (20.4 g, 148 mmol). The resulting suspension was stirred for 16 hours at room temperature under nitrogen. The reaction was concentrated in vacuo and the residue was dissolved in water (150 mL) and extracted with EtOAc (2×150 mL). The combined organic layers were washed with brine (150 mL), NaOH (2M aqueous, 150 mL), dried over MgSO$_4$ and concentrated in vacuo. The residue was purified using silica gel column chromatography eluting with 5-40% EtOAc/heptane to afford the title compound as a colourless oil (17.8 g, 86%).

LCMS (Method B) Rt=4.14 minutes, no mass ion observed.

$^1$H NMR (400 MHz, CDCl$_3$): δ ppm 8.25 (1H, s), 8.00 (1H, d), 7.70 (1H, d), 7.55 (2H, d), 7.50-7.25 (6H, m), 7.00 (2H, d), 5.40 (2H, s), 4.55 (2H, s), 1.50 (9H, s).

Preparation 18

Benzyl 4'-hydroxy-[1,1'-biphenyl]-3-carboxylate

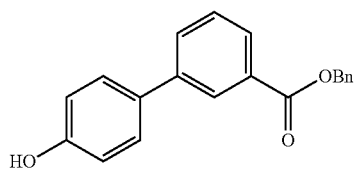 [SMILES: O=C(OCc1ccccc1)c1cccc(-c2ccc(O)cc2)c1]

A mixture of benzyl 3-bromobenzoate (Preparation 19, 15 g, 51.5 mmol), sodium carbonate (19.1 g, 180 mmol) and (4-hydroxyphenyl)boronic acid (8.53 g, 61.8 mmol) dissolved in dioxane/water (5:1 v/v, 450 mL) was deoxygenated for 30 minutes under nitrogen. Pd(PPh$_3$)$_4$ (5.95 g, 5.15 mmol) was added and the reaction was heated to 100° C. for 90 minutes under nitrogen. After cooling to room temperature, EtOAc (450 mL) and water (450 mL) were added and the layers were separated. The aqueous layer was extracted with EtOAc (2×450 mL) and the combined organic layers washed with brine (450 mL). The organic layer was dried over MgSO$_4$ and the solvent removed in vacuo to afford a black residue. The residue was filtered through a pad of silica washing with EtOAc/heptane (1:1 v/v, 2 L) and concentrated in vacuo. The residue was triturated with toluene (75 mL) and filtered. The resulting solid was washed with further toluene (25 mL) and dried under reduced pressure to afford the title compound as a tan solid (12.7 g, 81%).

LCMS (Method B) Rt=3.39 minutes, ES− MS m/z 303.3 [M−H]−

$^1$H NMR (400 MHz, CDCl$_3$): δ ppm 8.25 (1H, s), 8.00 (1H, d), 7.70 (1H, d), 7.50-7.30 (8H, m), 6.90 (2H, d), 5.40 (2H, s), 5.00 (1H, br s).

Preparation 19

Benzyl 3-bromobenzoate

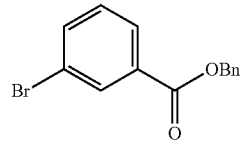 [SMILES: O=C(OCc1ccccc1)c1cccc(Br)c1]

To a solution of 3-bromobenzoic acid (20 g, 99.5 mmol) dissolved in DMF (100 mL) was added KHCO$_3$ (9.96 g, 99.5 mmol). Benzyl bromide (11.8 mL, 99.5 mmol) was added dropwise and the reaction was stirred at room temperature under nitrogen overnight. The reaction was concentrated in vacuo. The residue which was partitioned between EtOAc (200 mL) and water (200 mL). The layers were separated and the organic layer was washed with citric acid (1M, 200 mL), NaHCO$_3$ (saturated, aqueous, 200 mL) and brine (200 mL). The organic layer was dried over MgSO$_4$ and the solvent removed under reduced pressure to afford the title compound as a pale yellow oil (28.3 g, 97%).

LCMS (Method B) Rt=3.80 minutes, no ionisation observed.

$^1$H NMR (400 MHz, CDCl$_3$): δ ppm 8.20 (1H, s), 8.00 (1H, s), 7.65 (1H, s), 7.50-7.25 (6H, m), 5.35 (2H, s).

Preparation 20

6-(6-(3',5,5'-Tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxamido)hexanamido)hexanoic Acid

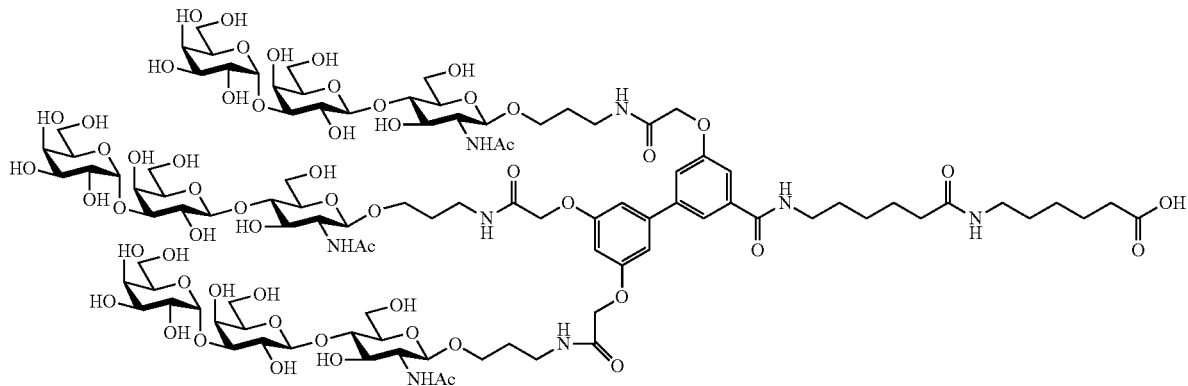

The title compound was prepared using Preparation 21 and benzyl 6-(6-aminohexanamido)hexanoate (JACS 136 (52) 18034-18043 (2014)) according to Preparation 14.

LCMS (Method B) Rt=1.47 minutes, ES$^+$ MS m/z 1201.3 [M+2H]$^+$/2; theoretical mass: 2400.0

Preparation 21

3',5,5'-Tris(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic Acid

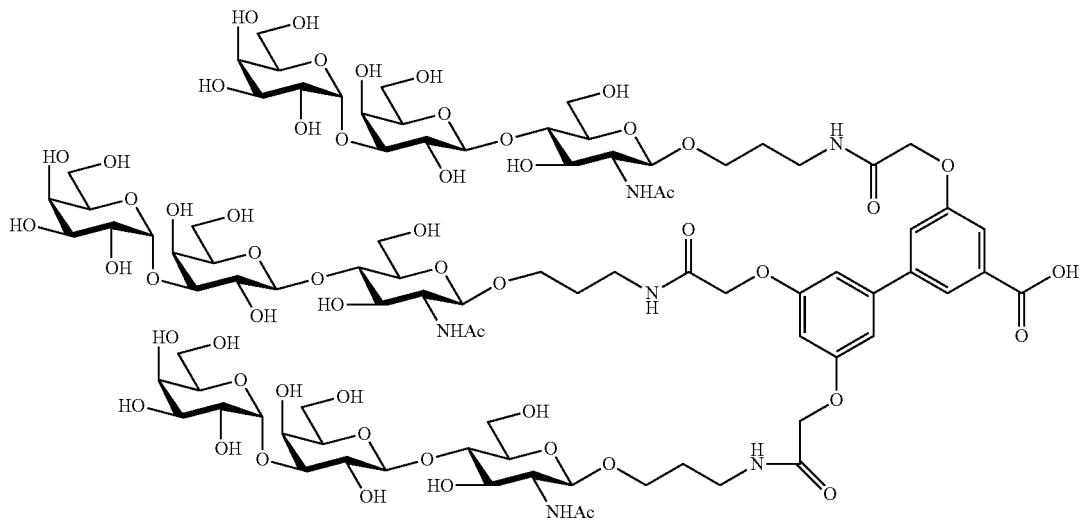

The title compound was prepared using alpha-Gal and 2,2',2''-((5'-((benzyloxy)carbonyl)-[1,1'-biphenyl]-3,3',5-triyl)tris(oxy))triacetic acid (WO2017060729) according to Preparation 14.

LCMS (Method B) Rt=1.27 minutes, ES$^+$ MS m/z 1088.4 [M+2H]$^+$/2, theoretical mass: 2174.0.

Preparation 22

4'-(2-((6-((6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-carboxylic Acid

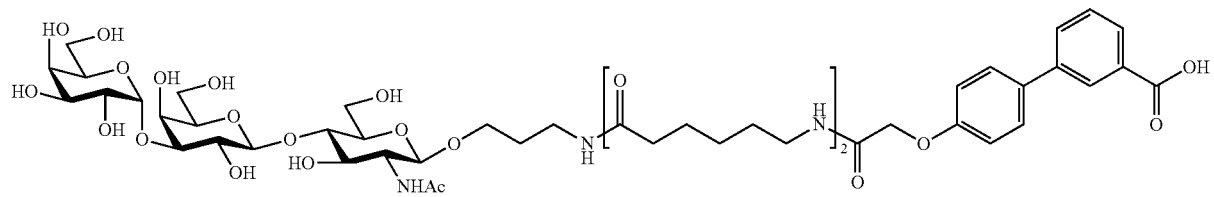

Benzyl 4'-(2-((6-((6-((3-(((2R,3R,4R,5S,6R)-3-acetamido-5-(((2S,3R,4S,5S,6R)-3,5-dihydroxy-6-(hydroxymethyl)-4-(((2R, 3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-carboxylate (Preparation 23, 215 mg) was dissolved in a solution of TEA and water (1:1 v/v, 10 mL) and stirred overnight. The reaction was concentrated in vacuo and the residue was purified using reverse phase column chromatography eluting with 1-30% MeCN/water with 0.1% NH$_3$. The resulting residue that contained starting material was further treated with a solution of TEA and water (1:1 v/v, 10 mL) and stirred for 5 days. The reaction was concentrated in vacuo and the residue was purified using reverse phase column chromatography eluting with 1-30% MeCN/water with 0.1% NH$_3$ followed by 1-20% MeCN/water with 0.1% NH$_3$ to afford the title compound as a colourless solid (total=172 mg, 87%).

LCMS (Method B) Rt=1.65 minutes, ES$^+$ MS m/z 1083.9 [M+H]$^+$

Preparation 23

Benzyl 4'-(2-((6-((6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-carboxylate

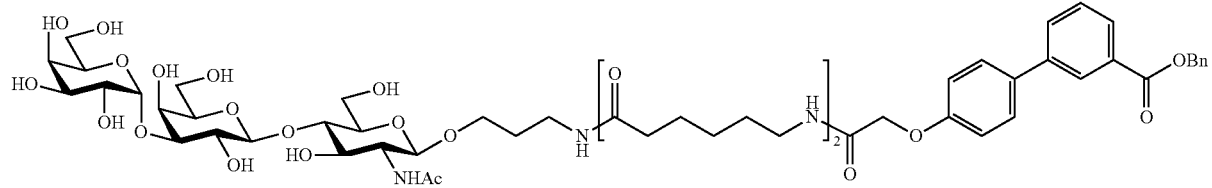

To a solution of 6-(6-(2-((3'-((benzyloxy)carbonyl)-[1,1'-biphenyl]-4-yl)oxy)acetamido)hexanamido)hexanoic acid (Preparation 24, 110 mg, 187 μmol) dissolved in DMF (2.2 mL) was added HATU (106 mg, 280 μmol) and TEA (80 μL, 560 μmol). A solution of alpha-Gal (146 mg, 243 μmol) in DMSO (1 mL) was added and the reaction was stirred for 1 hour. The reaction was purified directly using reverse phase column chromatography eluting with 10-70% MeCN in water with 0.1% $NH_3$ to afford title compound as a colourless solid (215 mg, 98%).

LCMS (Method B) Rt=2.62 minutes, $ES^+$ MS m/z 1173.7 $[M+H]^+$

Preparation 24

6-(6-(2-((3'-((benzyloxy)carbonyl)-[1,1'-biphenyl]-4-yl)oxy)acetamido)hexanamido) hexanoic Acid

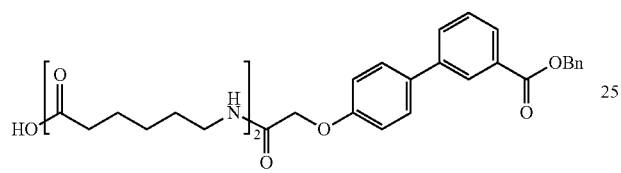

Benzyl 4'-(2-((6-((6-(tert-butoxy)-6-oxohexyl)amino)-6-oxohexyl)amino)-2-oxoethoxy)-[1,1'-biphenyl]-3-carboxylate (Preparation 25, 320 mg, 496 μmol) was dissolved in a solution of DCM, TFA and water (10:10:1 v/v/v, 10 mL) and stirred for 3 hours. The reaction was concentrated in vacuo and the residue azeotroped with dioxane/toluene (1:1 v/v, 3×24 mL). The crude material was purified using reverse phase column chromatography eluting with 10-80% MeCN/water with 0.1% formic acid to afford the title compound as a colourless solid (168 mg, 66%).

LCMS (Method B) Rt=2.81 minutes, $ES^-$ MS m/z 589.2 $[M]^-$ $^1$H NMR (400 MHz, $CDCl_3$): δ ppm 8.25 (1H, s), 8.02 (1H, d), 7.72 (1H, d), 7.59 (2H, d), 7.52-7.45 (3H, m), 7.42-7.35 (3H, m), 7.00 (2H, d), 6.74 (1H, br s), 5.71 (1H, br s), 5.40 (2H, s), 4.56 (2H, s), 3.44-3.39 (2H, m), 3.32-3.28 (2H, m), 2.37 (2H, t), 2.15 (2H, t), 1.68-1.51 (6H, m), 1.41-1.33 (6H, m) ppm.

Preparation 25

Benzyl 4'-(2-((6-((6-(tert-butoxy)-6-oxohexyl)amino)-6-oxohexyl)amino)-2-oxoethoxy)-[1,1'-biphenyl]-3-carboxylate

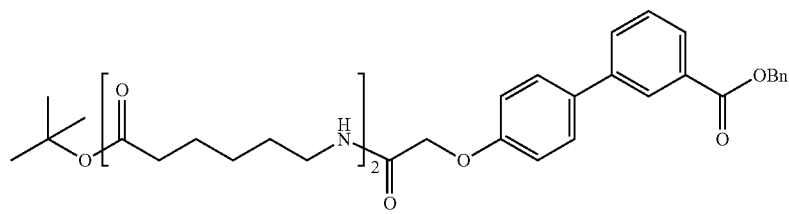

To a solution 2-((3'-((benzyloxy)carbonyl)-[1,1'-biphenyl]-4-yl)oxy)acetic acid (Preparation 16, 150 mg, 414 µmol, 1 eq) dissolved in DMF (3 mL) was added TEA (173 µL, 1.2 mmol) and a solution of tert-butyl 6-(6-aminohexanamido)hexanoate (Preparation 31, 162 mg, 538 µmol) in DMF (2 mL). HATU was then added (236 mg, 621 µmol) and the reaction was stirred for 1 hour at room temperature. The reaction was purified directly using silica gel column chromatography eluting with 0-100% EtOAc in Heptanes to afford the title compound as a colourless oil (320 mg, >100%).

LCMS (Method B) Rt=3.70 minutes, ES− MS m/z 645.3 [M]−

$^1$H NMR (400 MHz, CDCl$_3$): δ ppm 8.25 (1H, s), 8.05-8.00 (1H, m), 7.75-7.70 (1H, m), 7.60 (2H, d), 7.50-7.45 (3H, m), 7.40-7.35 (3H, m), 7.00 (2H, d), 6.70 (1H, br s), 5.60 (1H, br s), 5.40 (2H, s), 4.55 (2H, s), 2.25-2.10 (4H, m), 1.70-1.55 (9H, m), 1.55-1.45 (3H, m), 1.45 (9H, s), 1.40-1.30 (4H, m) ppm.

Preparation 26

1-(4'-(2-((6-((6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-yl)-1,8,15,22-tetraoxo-2,9,16,23-tetraazanonacosan-29-oic Acid

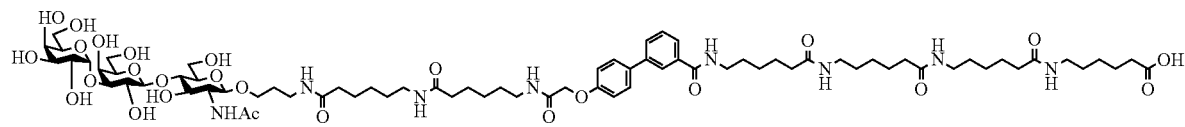

To a solution of benzyl 1-(4'-(2-((6-((6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-yl)-1,8,15,22-tetraoxo-2,9,16,23-tetraazanonacosan-29-oate (Preparation 27, 50 mg, 30 µmol) in MeOH (5 mL) and water (5 mL) was added 5% Pd/C (5 mg). The reaction was de-gassed and stirred under an atmosphere of hydrogen (balloon) overnight. The reaction was filtered through a syringe filter and the solution concentrated in vacuo to afford the title compound as a pale gray solid (26 mg, 60%).

LCMS (Method B) Rt=1.88 minutes, ES− MS m/z 1537.4 [M]−

Preparation 27

Benzyl 1-(4'-(2-(((6-((6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-yl)-1,8,15,22-tetraoxo-2,9,16,23-tetraazanonacosan-29-oate

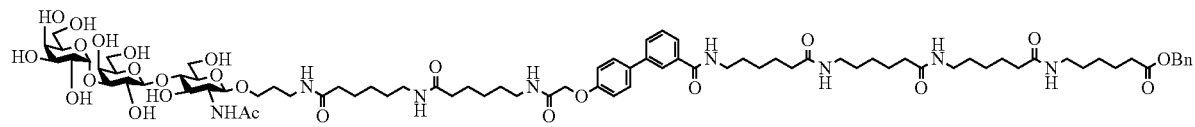

To a solution 4'-(2-(((6-((6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-carboxylic acid (Preparation 22, 50 mg, 46 μmol) in DMF (2 mL) was added HATU (26 mg, 69 μmol) and TEA (19 μL, 138 μmol). A solution of benzyl 6-(6-(6-(6-aminohexanamido)hexanamido)hexanamido)hexanoate hydrochloride (WO2017060729, 36 mg, 60 μmol) in DMF (2 mL) and TEA (13 μL, 92 μmol) was added to give a yellow solution and the reaction was stirred for 1 hour at room temperature. The reaction was purified directly using reverse phase column chromatography eluting with 2-70% MeCN in water with 0.1% $NH_3$ to afford the title compound as a colourless solid (50 mg, 66%).

LCMS (Method B) Rt=2.41 minutes, ES$^+$ MS m/z 1627.5 [M+H]$^+$

Preparation 28

1-(4',5-bis(2-(((6-((6-(3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-yl)-1,8,15,22-tetraoxo-2,9,16,23-tetraazanonacosan-29-oic Acid

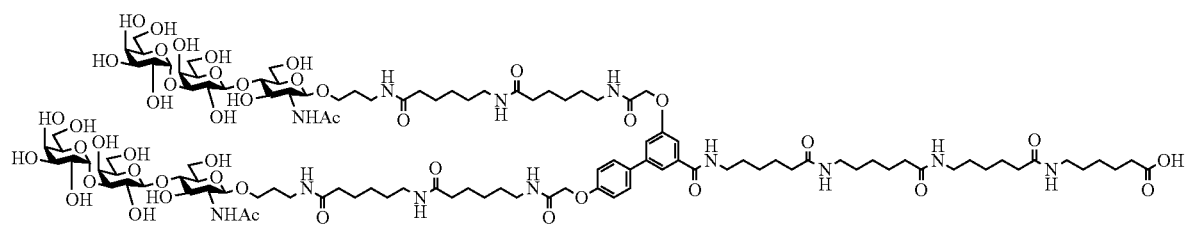

The title compound was prepared according the methods described for Preparation 27 and 26 using 4',5-bis(2-((6-((6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-carboxylic acid (Preparation 29) and benzyl 6-(6-(6-(6-aminohexanamido)-hexanamido)hexanamido)hexanoate (WO2017060729).

LCMS (Method B) Rt=1.72 minutes, ES$^+$ MS m/z 1211.7 [M+2H]$^+$/2; theoretical mass: 2420.7

Preparation 29

4',5-bis(2-((6-((6-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-6-oxohexyl)amino)-6-oxohexyl)amino)-2-oxoethoxy)-[1,1'-biphenyl]-3-carboxylic Acid

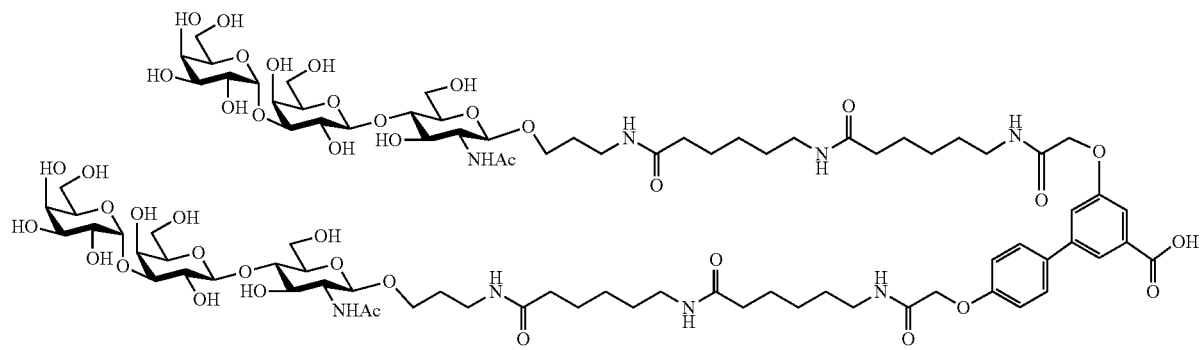

The title compound was prepared according to the methods described for Preparation 22 and 23 using 6,6'-((6,6'-((2,2'-((5-((benzyloxy)carbonyl)-[1,1'-biphenyl]-3,4'-diyl)bis(oxy))bis(acetyl))bis(azanediyl))bis(hexanoyl))bis(azanediyl))dihexanoic acid (Preparation 30) and alpha-Gal.

LCMS (Method B) Rt=1.55 minutes, ES$^-$ MS m/z 1967.3 [M−H]$^-$

Preparation 30

6,6'-((6,6'-((2,2'-((5-((benzyloxy)carbonyl)-[1,1'-biphenyl]-3,4'-diyl)bis(oxy))bis(acetyl))bis(azanediyl))bis(hexanoyl))bis(azanediyl))dihexanoic Acid

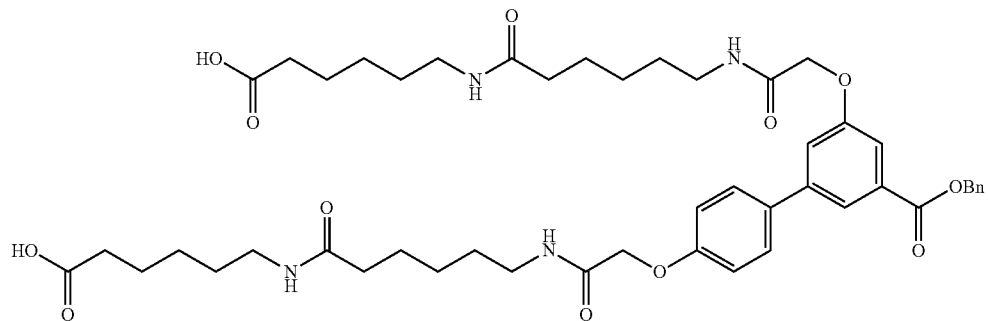 [SMILES: O=C(O)CCCCCNC(=O)CCCCCNC(=O)COc1ccc(-c2cc(OCC(=O)NCCCCCC(=O)NCCCCCC(=O)O)cc(C(=O)OCc3ccccc3)c2)cc1]

The title compound was prepared according to the methods described for Preparation 25 and 24 using tert-butyl 6-(6-aminohexanamido)hexanoate (Preparation 31) and 2,2'-((5-((benzyloxy)carbonyl)-[1,1'-biphenyl]-3,4-diyl)bis(oxy))diacetic acid (WO2017060729).

LCMS (Method B) Rt=2.67 minutes, ES⁻ MS m/z 889.5 [M−H]⁻

Preparation 31 tert-butyl 6-(6-aminohexanamido)hexanoate

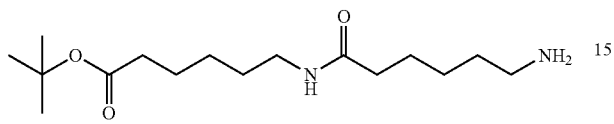

The title compound was prepared according to the methods described for Preparation 27 and 26 using tert-butyl 6-aminohexanoate and 6-{[(benzyloxy)carbonyl]amino}hexanoic acid.

¹H NMR (400 MHz, CDCl₃): δ ppm 5.71 (1H, br s), 3.30-3.20 (2H, m), 2.80-2.70 (2H, m), 2.28-2.07 (4H, m), 1.72-1.29 (21H, m).

SYNTHESIS OF EXAMPLES

Example 1

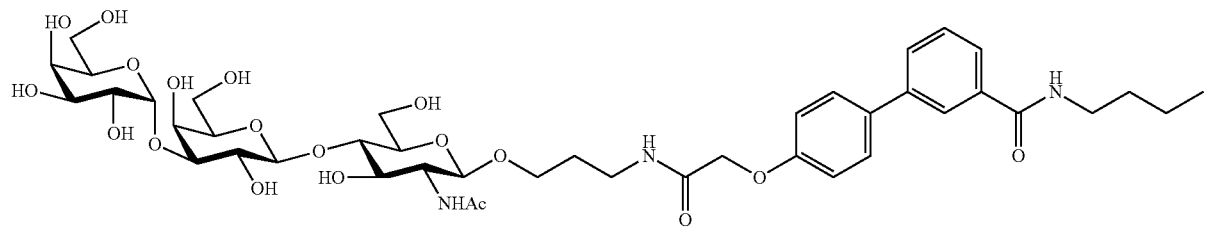

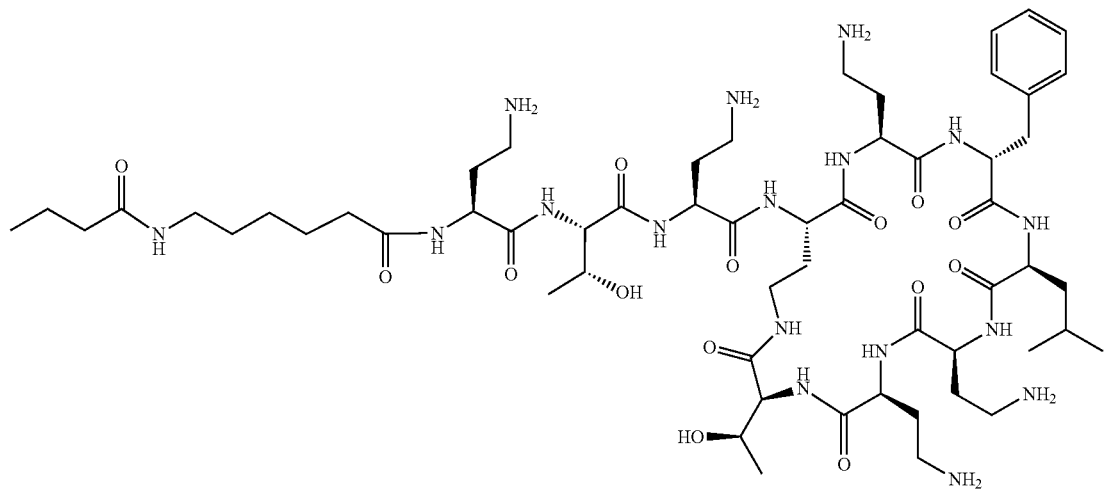

To a solution of Preparation 14 (1.2 mg, 0.0011 mmol) in DMF (0.5 mL) was added DIPEA (4.0 eq) and a solution of Preparation 1 (2.5 mg, 0.0024 mmol) in DMF (200 μL). HATU (1.2 eq) was then added and the reaction was stirred at room temperature for 1 hour. The reaction was purified by reverse phase column chromatography (C-18, 4 g, 0-70% MeCN/water) and dried under vacuum. The residue was dissolved in 3% hydrazine/MeOH (0.5 mL) and the reaction was shaken for 30 minutes. The material was purified using preparative HPLC column chromatography (column: Gemini-NX 5u C18 110A 150*4.6 mm; Flow: 1.0 ml/min T=30° C.; Mobile Phase A: 0.1% TFA in H$_2$O B: 0.1% TFA in MeCN; Instrument: Agilent 1260 HPLC-(5-521) and lyophilized to afford the title compound as the trifluoroacetate salt (0.1 mg).

HPLC (Method 1) Rt=15.11-15.76 minutes;

MS m/z 1064.0 [M+2H]$^+$/2 and 710 [M+3H]$^+$/3, theoretical mass: 2127.0.

The following Examples 2-25 were prepared using the appropriate Preparations herein and according to Example 1 (amide bond formation followed by hydrazinolysis). The Examples were isolated as TFA salts and analysed by HPLC as described below:

Method 1: Gemini-NX 5 um, C18, 110A, 150×4.6 mm; Flow: 1.0 mL/min. Mobile Phase A: 0.1% TFA in H$_2$O B: 0.1% TFA in MeCN; Instrument: Agilent 1200 HPLC-BE (1-614). Gradient: 0 mins (85% A), 20 mins (55% A), 20.1 mins (10% A), 23 mins (10% A).

Method 2: XBridge C18, 3.5 um, 2.1×30 mm. Flow: 1.0 mL/min. Mobile Phase A: 0.1% TFA in water; Mobile phase B: MeCN. Gradient: 0 mins (5% B), 6 mins (95% B), 7 mins (95% B), 8 mins (5% B). Temp: 40° C.

Example 2

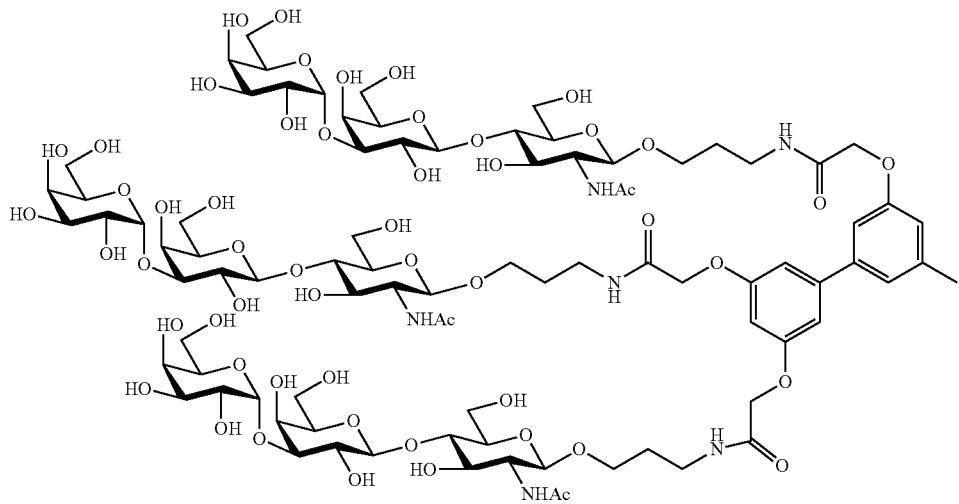

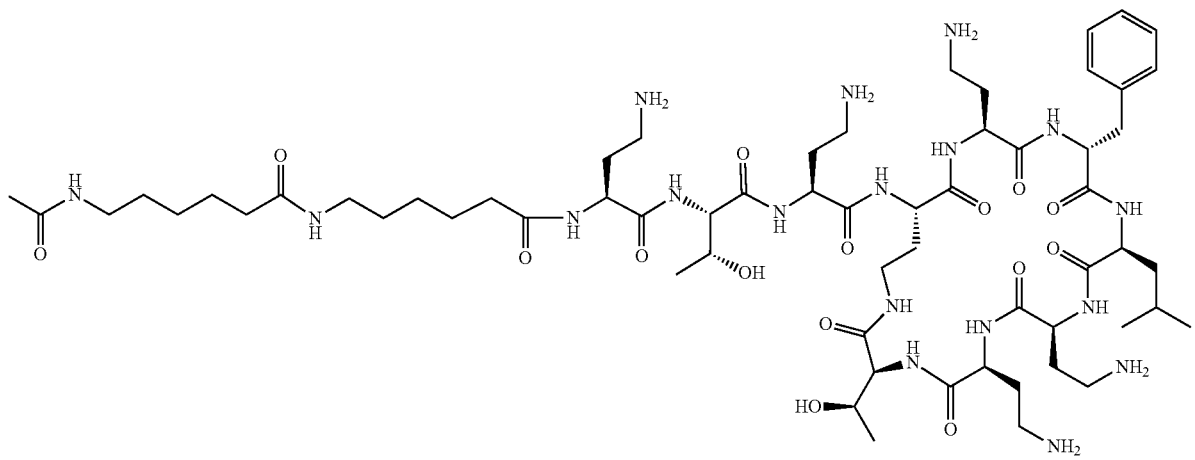

The compound of Example 2 was prepared in an analogous manner to the procedure described in Example 1 using Preparation 20 and Preparation 1.

HPLC (Method 1) Rt=6.31-7.31 minutes
MS m/z 1149.0 [M+3H]$^+$/3, theoretical mass: 3445.6

Example 3

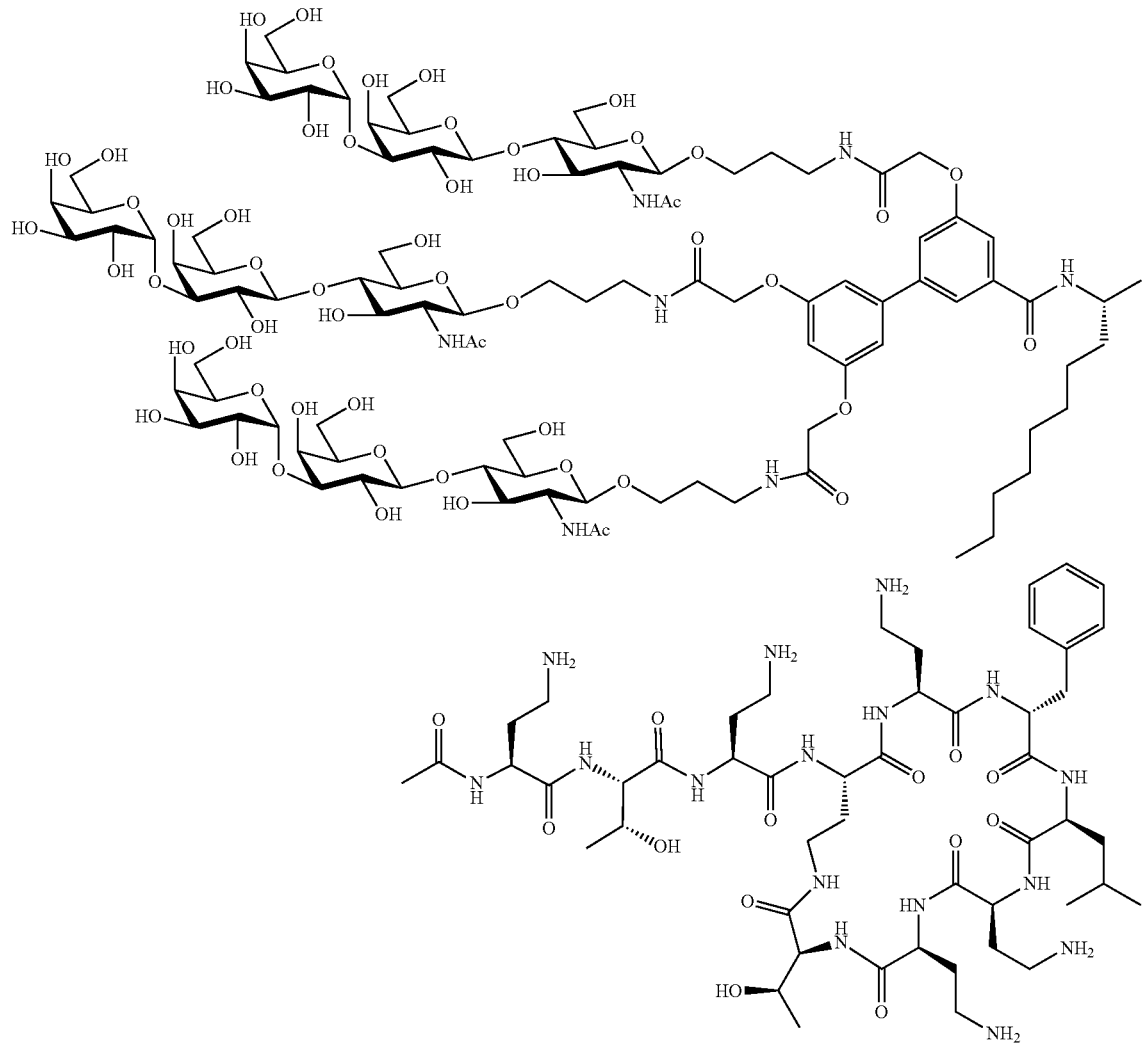

The compound of Example 3 was prepared in an analogous manner to the procedure described in Example 1 using Preparation 21 and Preparation 3.

HPLC (Method 1) Rt=9.66-10.84 minutes
MS m/z 1130 [M+3H]$^+$/3, theoretical mass: 3388.6

Example 4

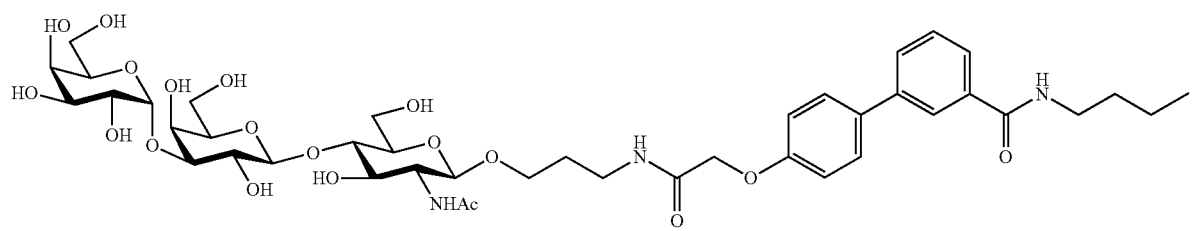

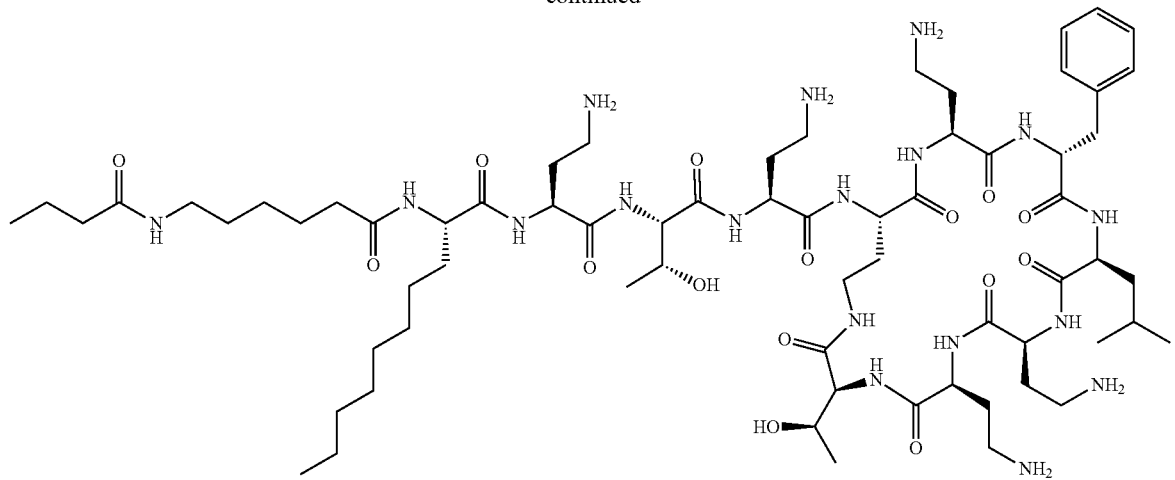
The compound of Example 4 was prepared in an analogous manner to the procedure described in Example 1 using Preparation 14 and Preparation 3.
HPLC (Method 1) Rt=9.82-10.24 minutes
MS m/z 1149.0 [M+2H]$^+$/2, theoretical mass: 2297.7
Example 5
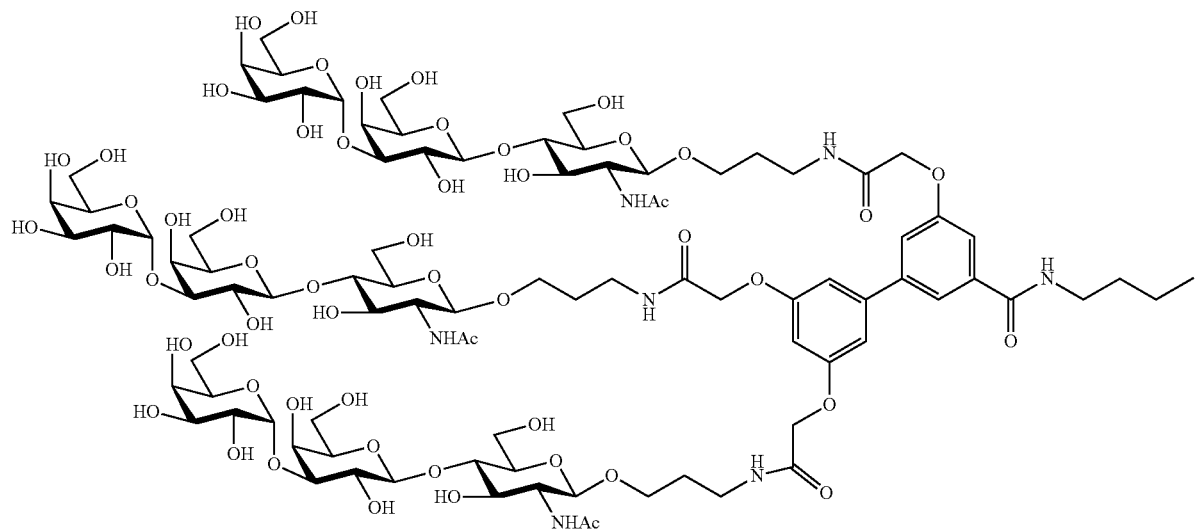

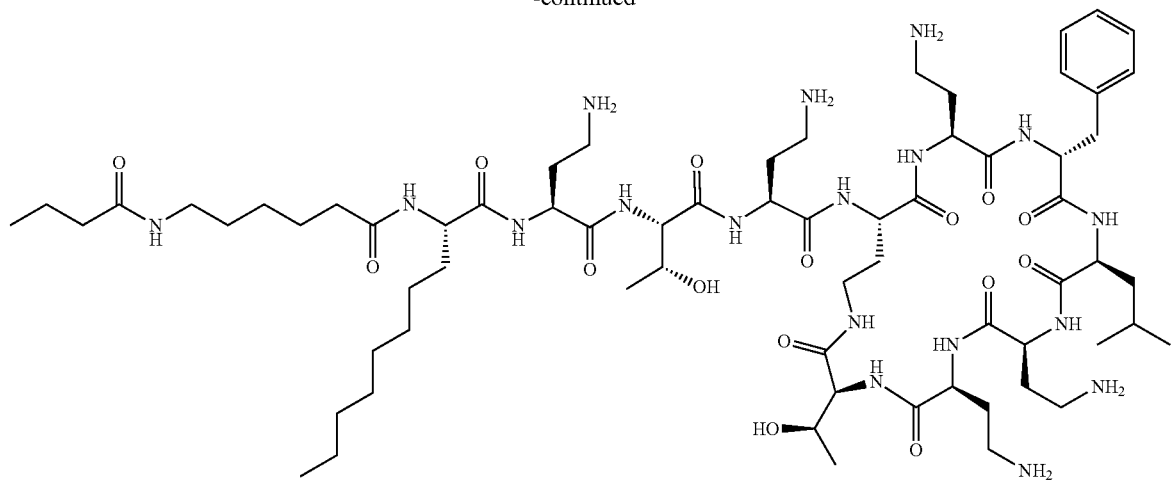
The compound of Example 5 was prepared in an analogous manner to the procedure described in Example 1 using Preparation 20 and Preparation 3.
HPLC (Method 1) Rt=10.23-10.81 minutes
MS m/z 904.0 [M+4H]$^+$/4, theoretical mass: 3614.9
Example 6
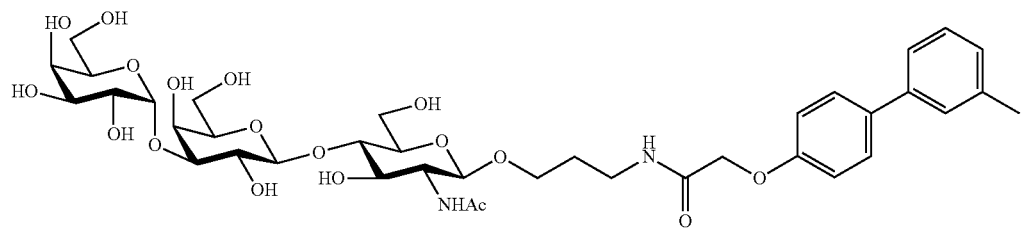
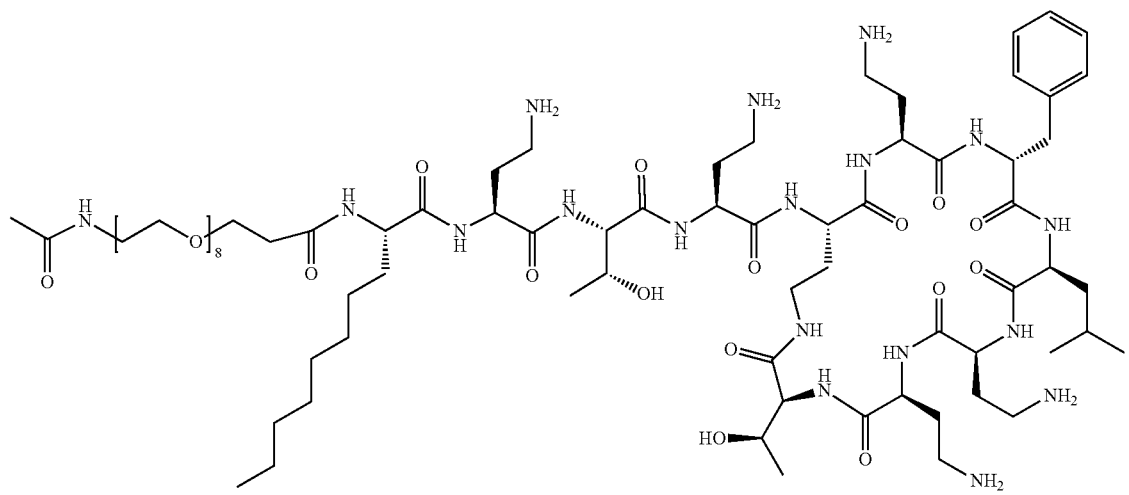

The compound of Example 6 was prepared in an analogous manner to the procedure described in Example 1 using Preparation 15 and Preparation 6.
HPLC (Method 1) Rt=9.71-10.55 minutes
HPLC (Method 2) Rt=2.953 minutes
MS m/z 832 [M+3H]⁺/3, theoretical mass: 2493.0
Example 7
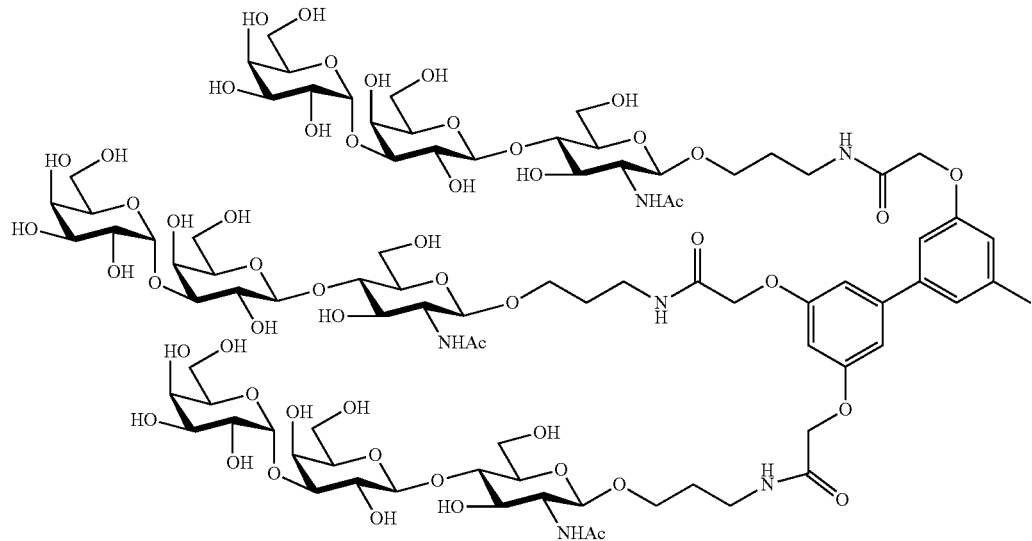
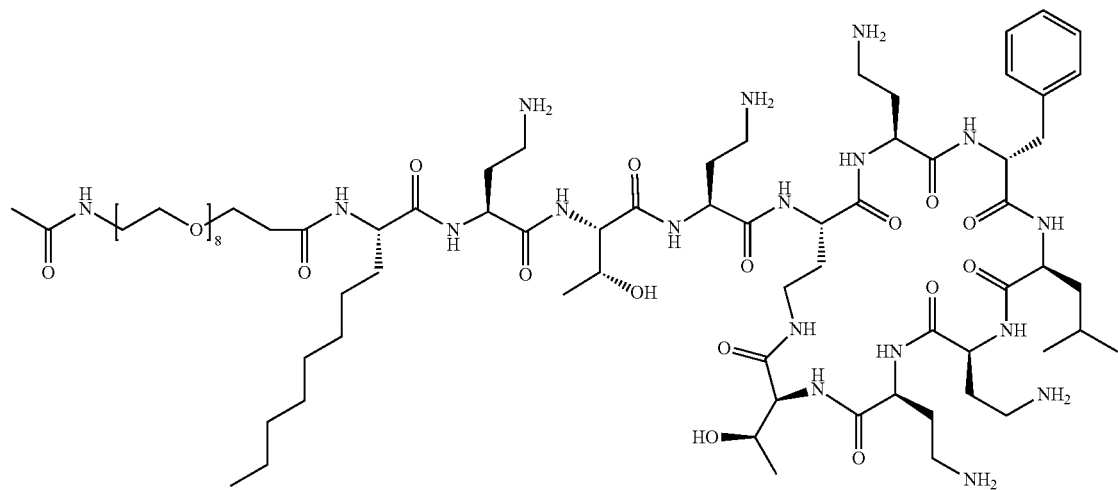

The compound of Example 7 was prepared in an analogous manner to the procedure described in Example 1 using Preparation 21 and Preparation 6.
HPLC (Method 1) Rt=10.06-10.98 minutes
HPLC (Method 2) Rt=2.640 minutes
MS m/z 1271 [M+3H]⁺/3, theoretical mass: 3809.0
Example 8
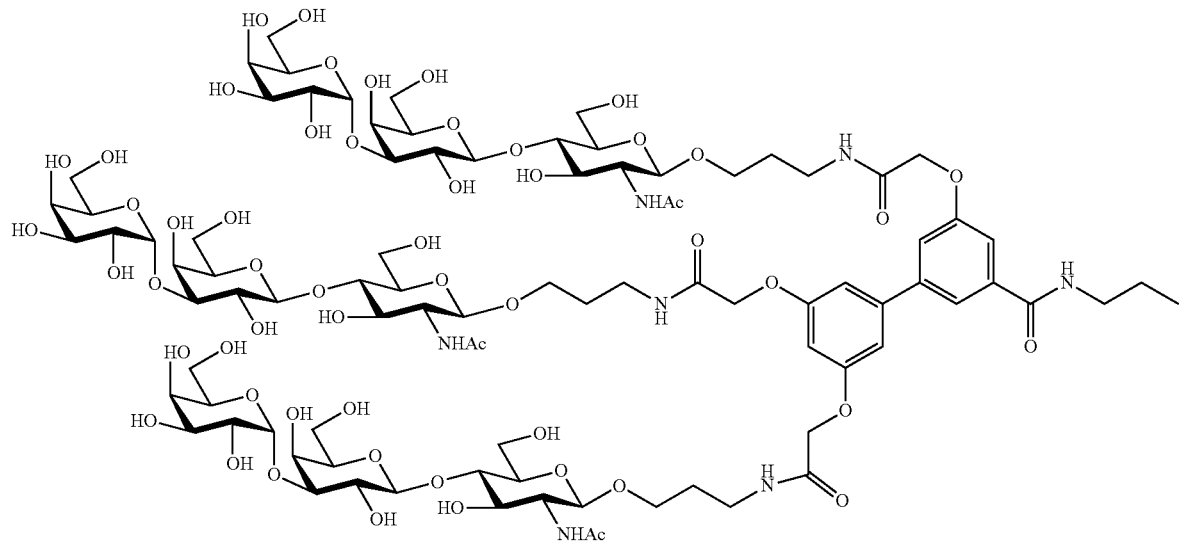
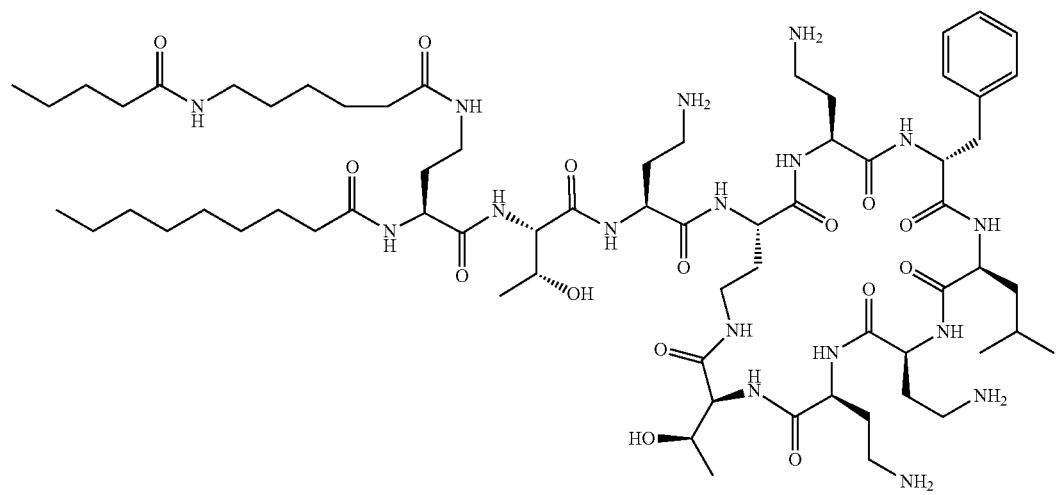

The compound of Example 8 was prepared in an analogous manner to the procedure described in Example 1 using Preparation 20 and Preparation 4.
HPLC (Method 1) Rt=14.43-15.24 minutes
MS m/z 897 [M+4H]$^+$/4, theoretical mass: 3585.8

Example 9

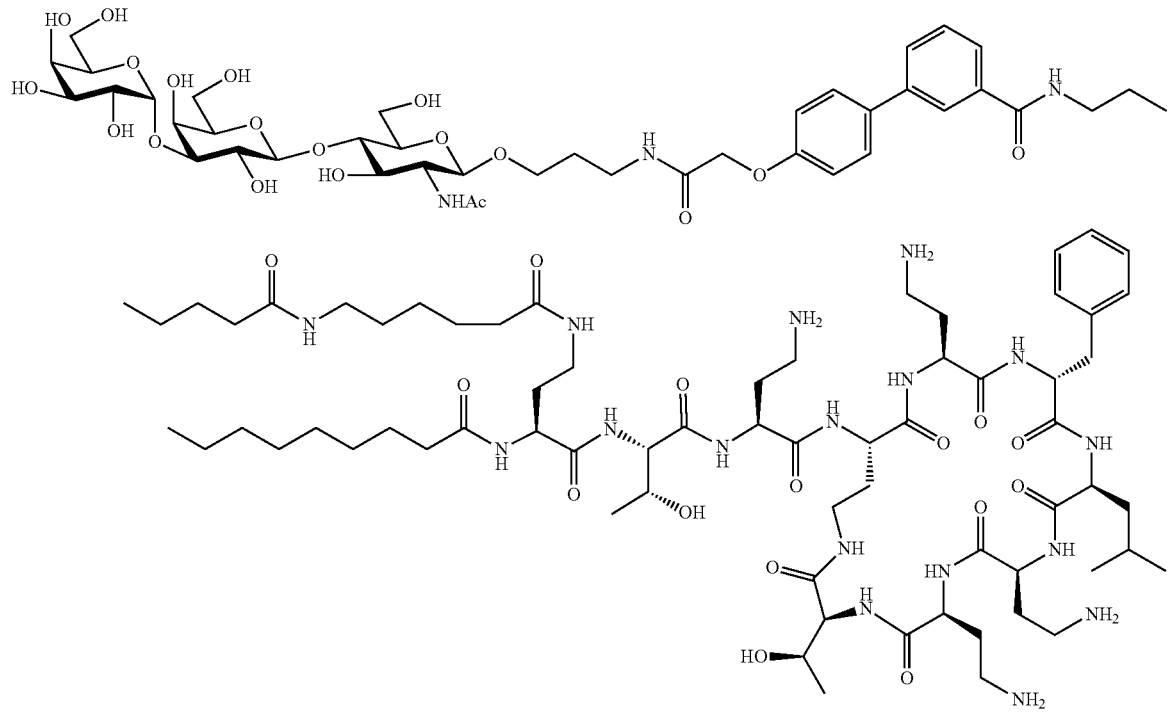

The compound of Example 9 was prepared in an analogous manner to the procedure described in Example 1 using Preparation 14 and Preparation 4.
HPLC (Method 1) Rt=17.57-17.84 minutes
MS m/z 1134 [M+2H]$^+$/2, theoretical mass: 2268.6

Example 10

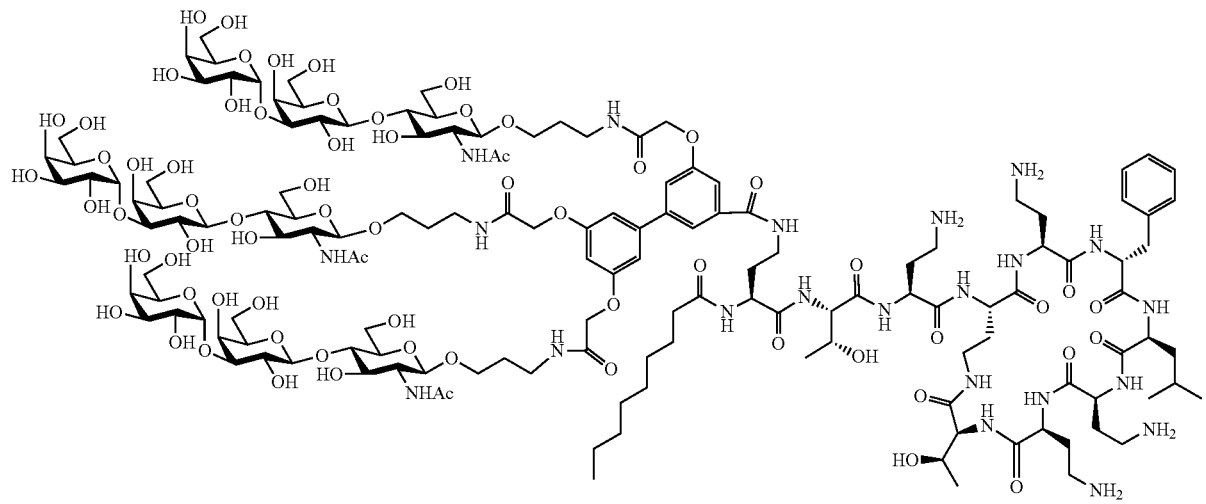

The compound of Example 10 was prepared in an analogous manner to the procedure described in Example 1 using Preparation 21 and Preparation 4.

HPLC (Method 1) Rt=13.70-14.50 minutes
MS m/z 1120 [M+3H]$^+$/3, theoretical mass: 3359.5

Example 11

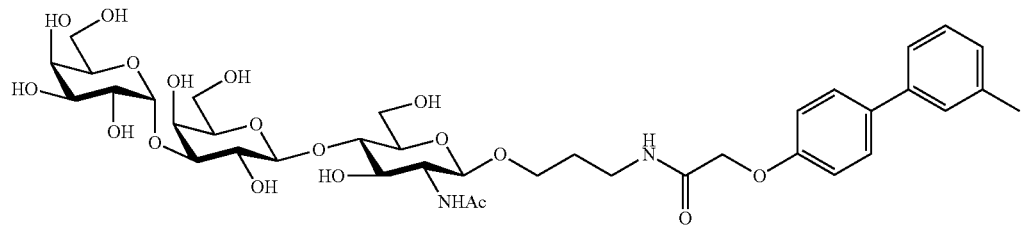

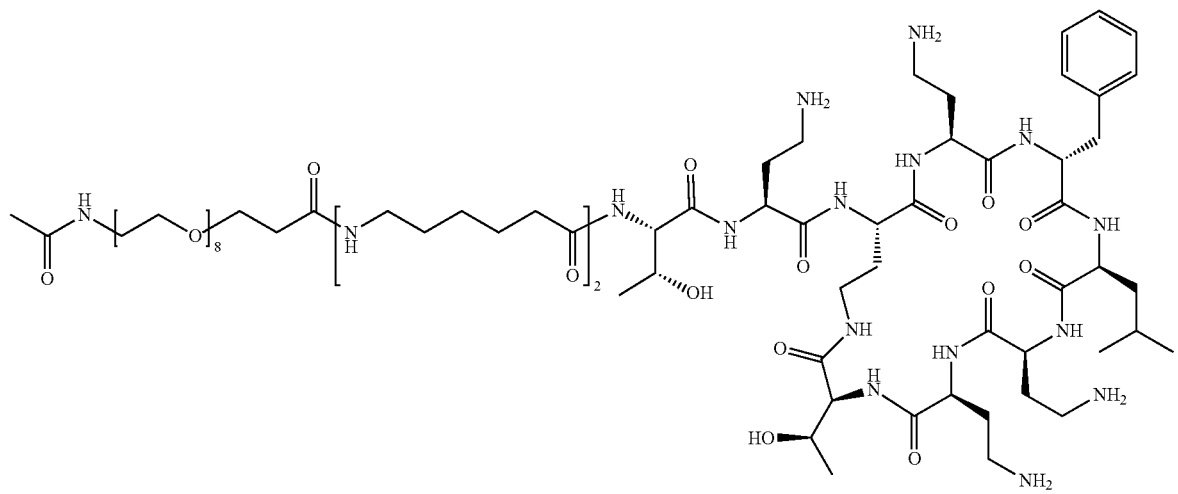

The compound of Example 11 was prepared in an analogous manner to the procedure described in Example 1 using Preparation 15 and Preparation 11.

HPLC (Method 1) Rt=9.75-10.79 minutes
MS m/z 817.9 [M+3H]$^+$/3, theoretical mass: 2450.3

Example 12

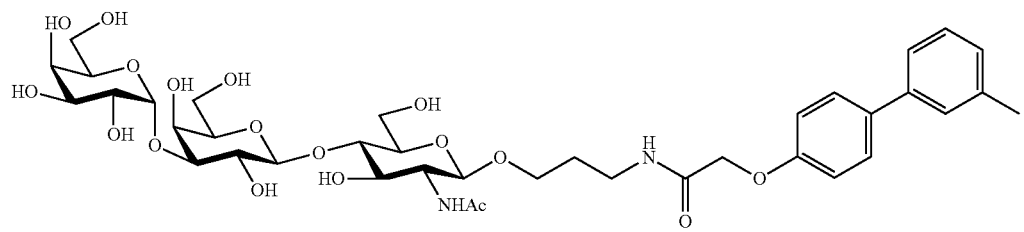

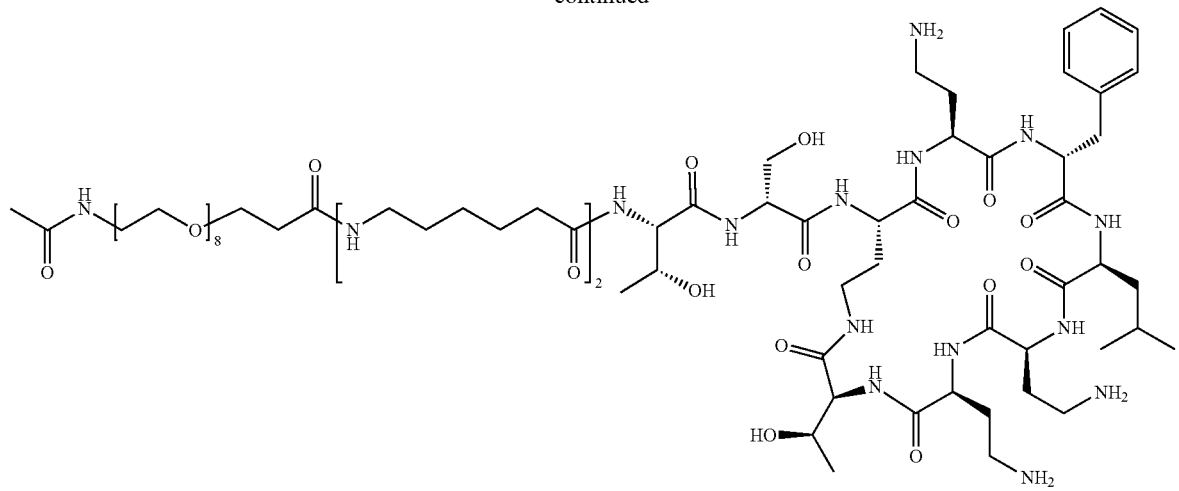
The compound of Example 12 was prepared in an analogous manner to the procedure described in Example 1 using Preparation 15 and Preparation 10.
HPLC (Method 1) Rt=10.77-11.23 minutes
HPLC (Method 2) Rt=3.065 minutes
MS m/z 1219.8 [M+2H]$^+$/2, theoretical mass: 2437.3
Example 13
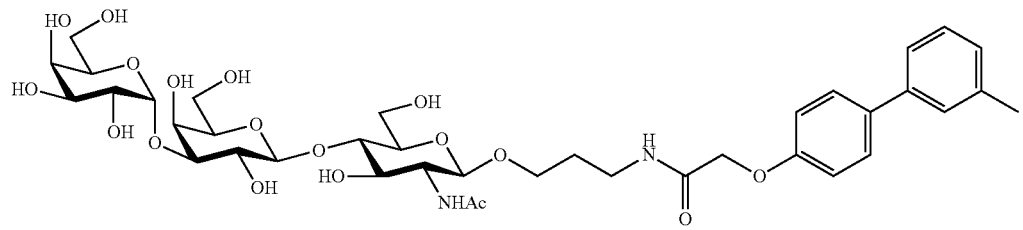
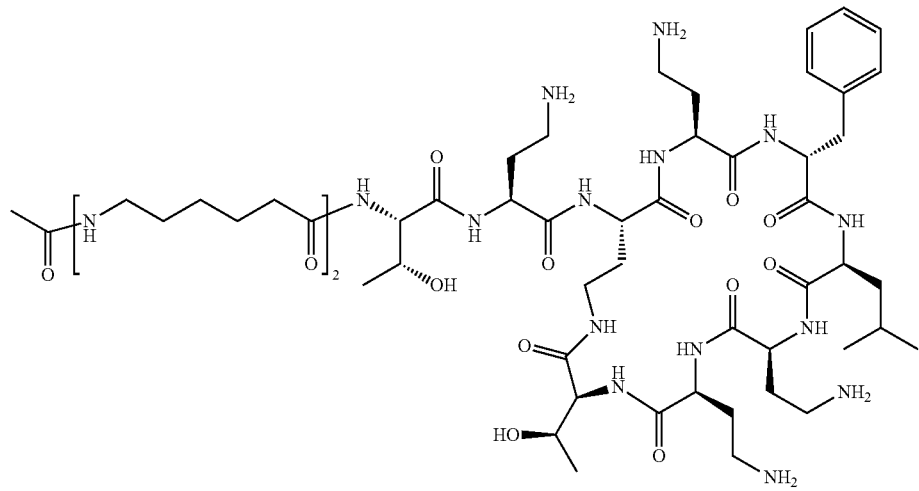

The compound of Example 13 was prepared in an analogous manner to the procedure described in Example 1 using Preparation 15 and Preparation 13.
HPLC (Method 1) Rt=8.77-11.14 minutes
MS m/z 1014.0 [M+2H]$^+$/2, theoretical mass: 2026.0

Example 14

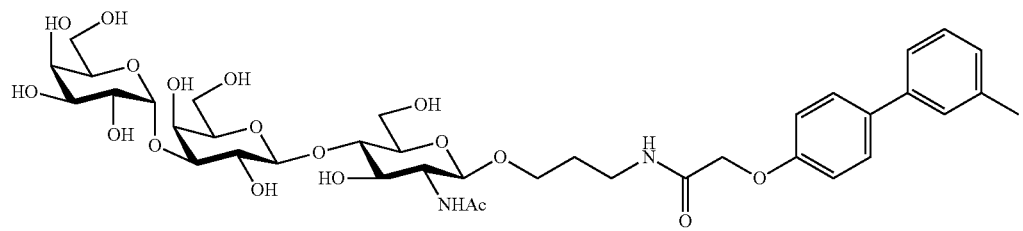

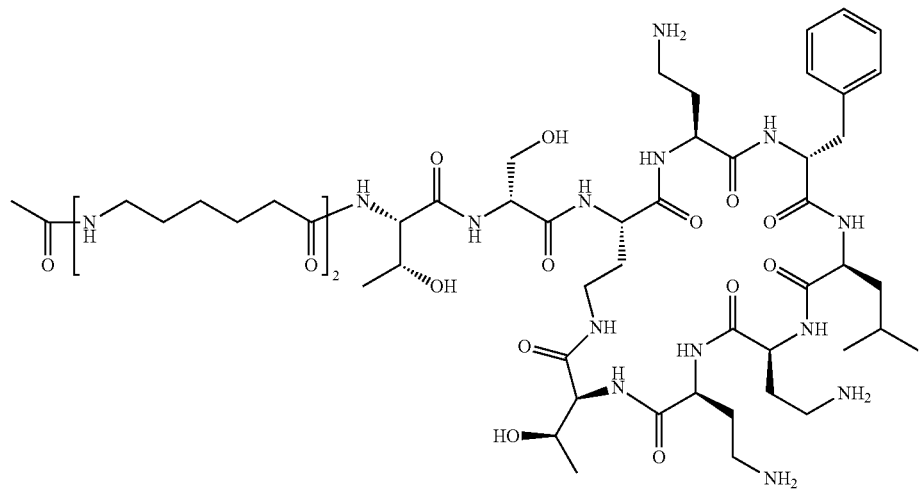

The compound of Example 14 was prepared in an analogous manner to the procedure described in Example 1 using Preparation 15 and Preparation 12.
HPLC (Method 1) Rt=10.71-11.64 minutes
MS m/z 1007.8 [M+2H]$^+$/2, theoretical mass: 2013.6

Example 15

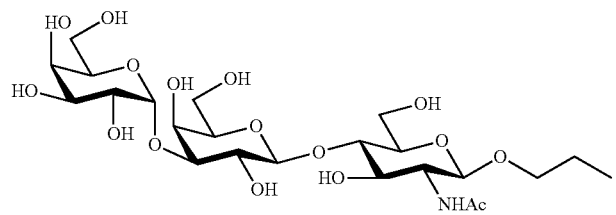

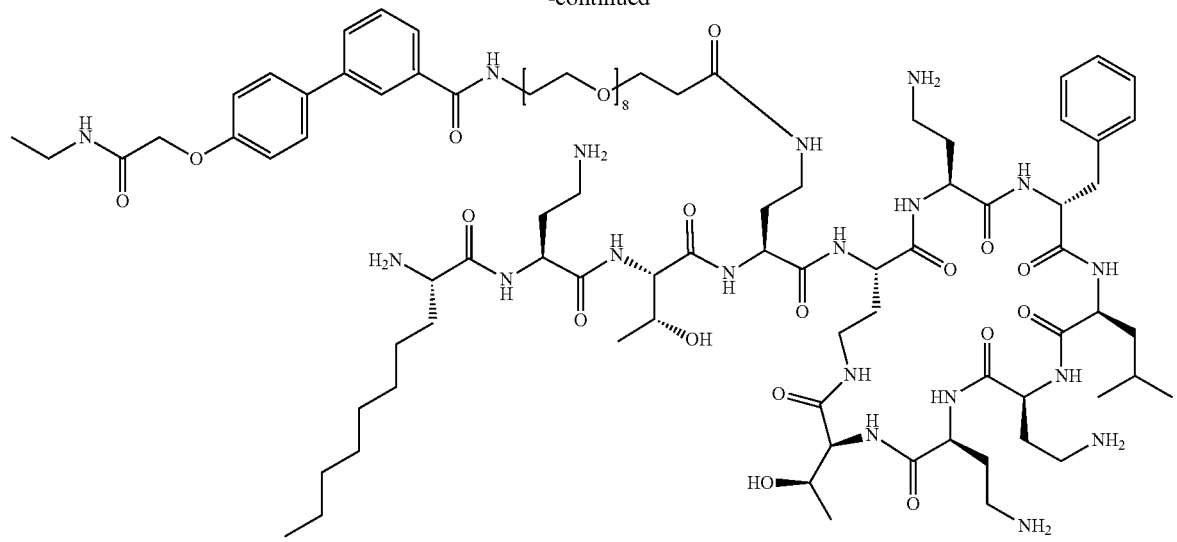
The compound of Example 15 was prepared in an analogous manner to the procedure described in Example 1 using Preparation 15 and Preparation 9.
HPLC (Method 2) Rt=8.390 minutes
MS m/z 1248.3 [M+2H]$^+$/2, 832.3 [M+3H]$^+$/3 theoretical mass: 2493.3
Example 16
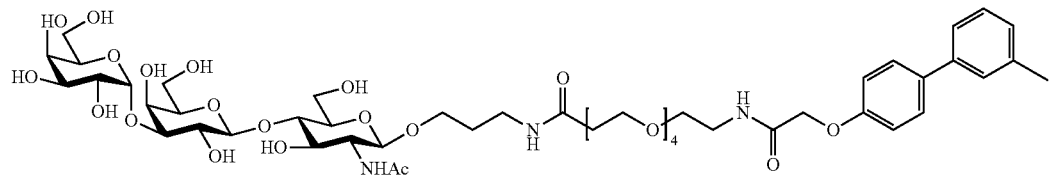
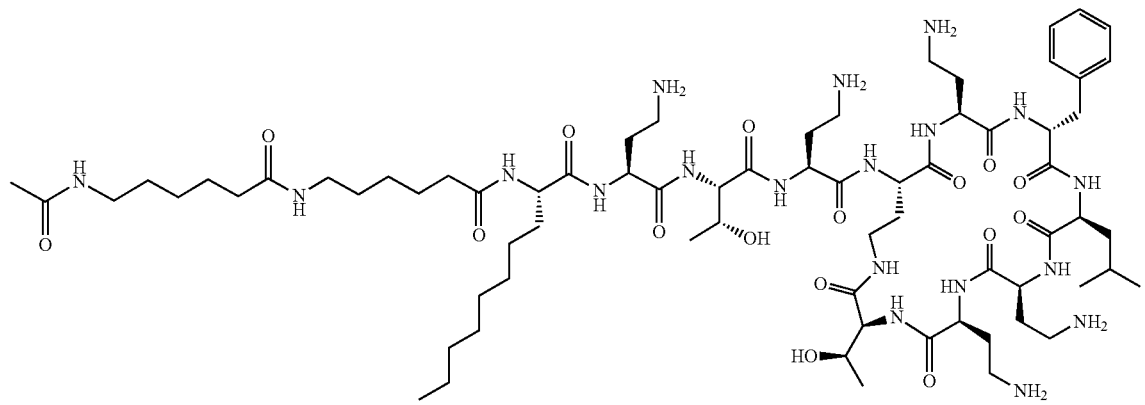

The compound of Example 16 was prepared in an analogous manner to the procedure described in Example 1 using 4-((22-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxylic acid (WO2017060729) and Preparation 8.

HPLC (Method 2) Rt=2.944 minutes
MS m/z 1273.0 [M+2H]$^+$/2, 849.1 [M+3H]$^+$/3; theoretical mass: 2543.4

Example 17

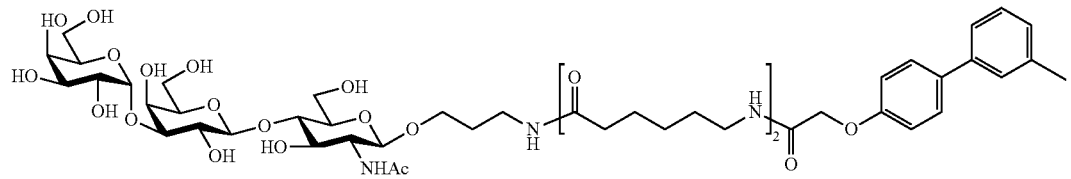

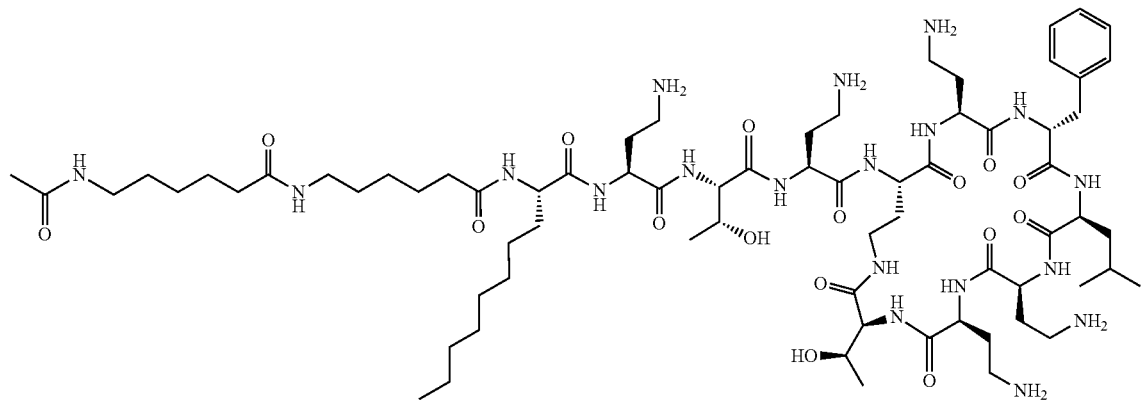

The compound of Example 17 was prepared in an analogous manner to the procedure described in Example 1 using Preparation 22 and Preparation 8.

HPLC (Method 2) Rt=2.964 minutes
MS m/z 1262.5 [M+2H]$^+$/2, 841.9 [M+3H]$^+$/3; theoretical mass: 2522.41

Example 18

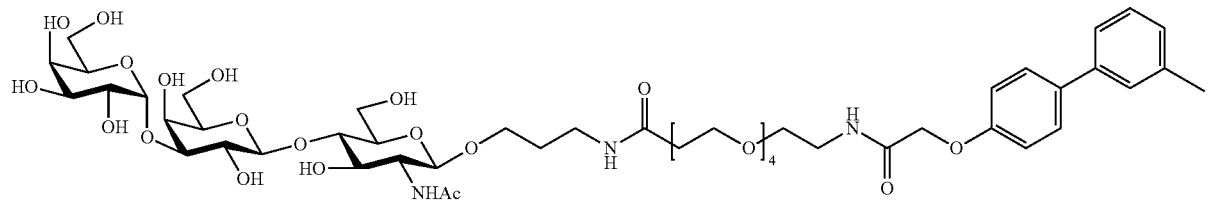

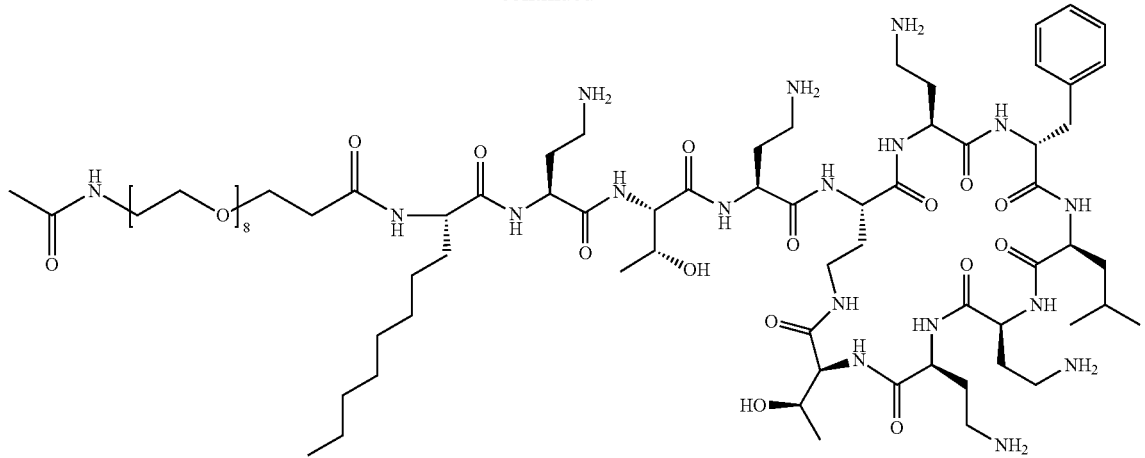

The compound of Example 18 was prepared in an analogous manner to the procedure described in Example 1 using 4'-((22-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxylic acid (WO2017060729) and Preparation 6.

HPLC (Method 2) Rt=2.963 minutes

MS m/z 914.9 [M+3H]$^+$/3, 686.3 [M+4H]$^+$/4; theoretical mass: 2740.5

Example 19

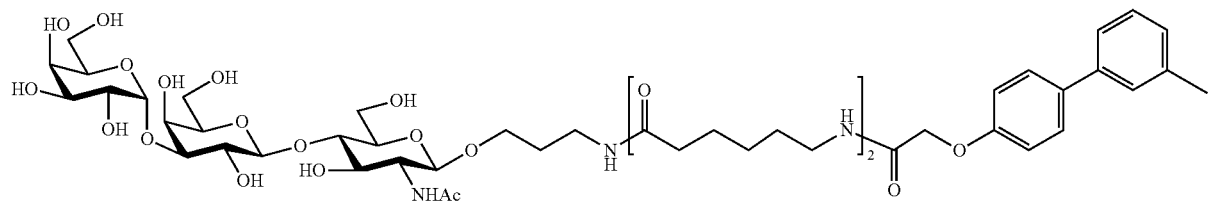

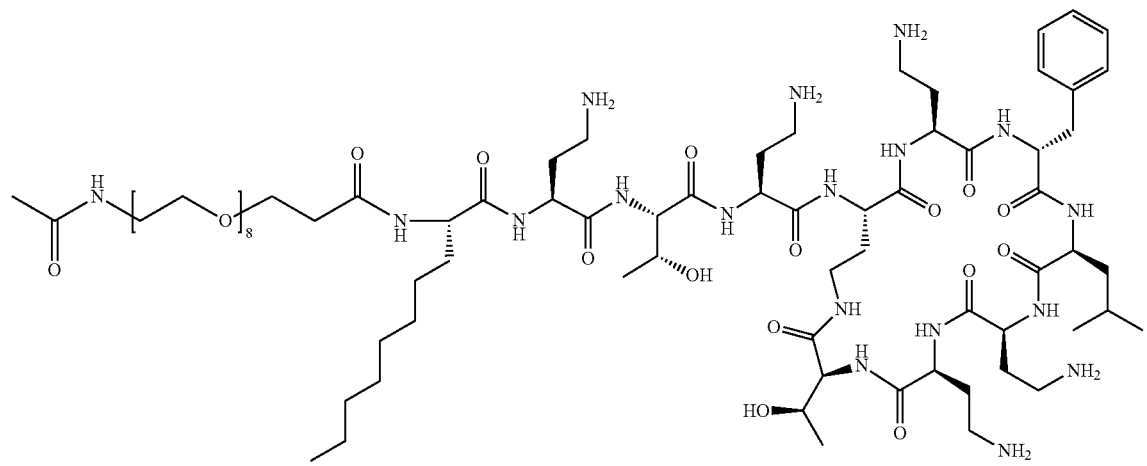

The compound of Example 19 was prepared in an analogous manner to the procedure described in Example 1 using Preparation 22 and Preparation 6.
HPLC (Method 2) Rt=2.998 minutes
MS m/z 1361.6 [M+2H]$^+$/2, 907.9 [M+3H]$^+$/3; theoretical mass: 2719.49

Example 20

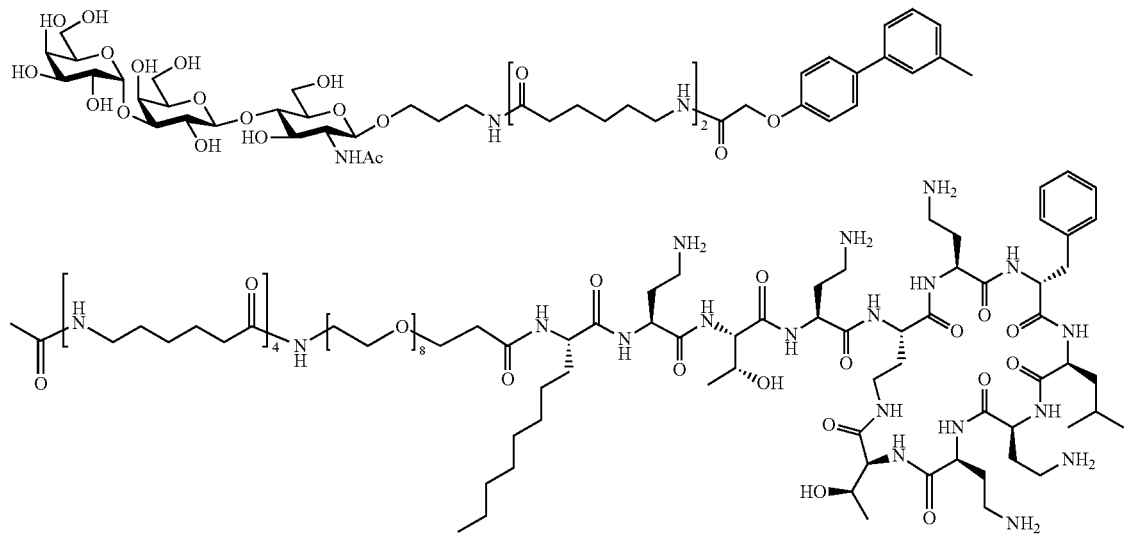

The compound of Example 20 was prepared in an analogous manner to the procedure described in Example 1 using Preparation 26 and Preparation 6.
HPLC (Method 2) Rt=3.033 minutes
MS m/z 1058.7 [M+3H]$^+$/3, 794.1 [M+4H]$^+$/4; theoretical mass: 3173.82

Example 21

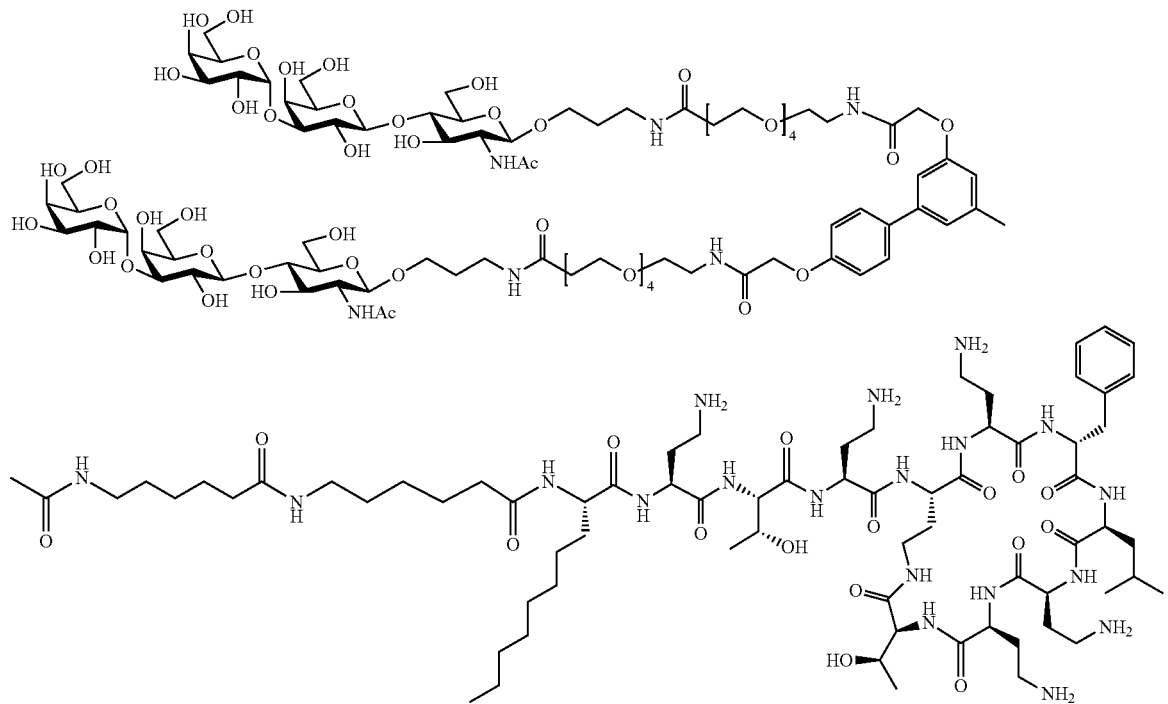

The compound of Example 21 was prepared in an analogous manner to the procedure described in Example 1 using 4',5-Bis((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)[1,1'-biphenyl]-3-carboxylic acid (WO2017060729) and Preparation 8.

HPLC (Method 2) Rt=2.761 minutes

MS m/z 1151.3 [M+3H]$^+$/3, 863.6 [M+4H]$^+$/4; theoretical mass: 3448.8

Example 22

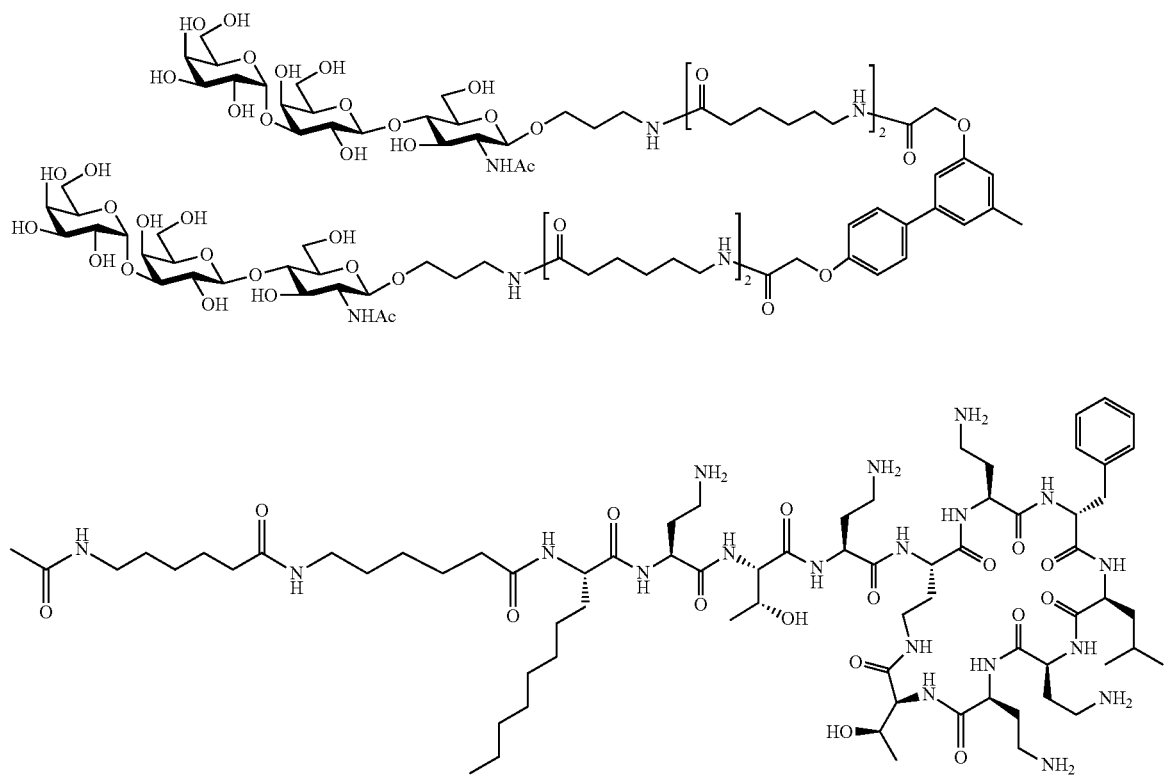

The compound of Example 22 was prepared in an analogous manner to the procedure described in Example 1 using Preparation 29 and Preparation 8.

HPLC (Method 2) Rt=2.791 minutes

MS m/z 1137.1 [M+3H]$^+$/3, 853.2 [M+4H]$^+$/4; theoretical mass: 3406.8

Example 23

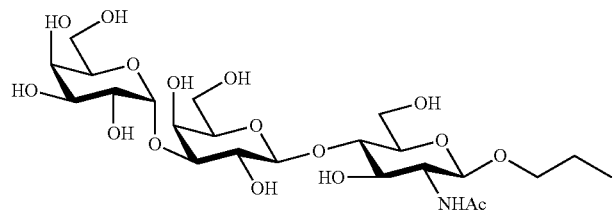

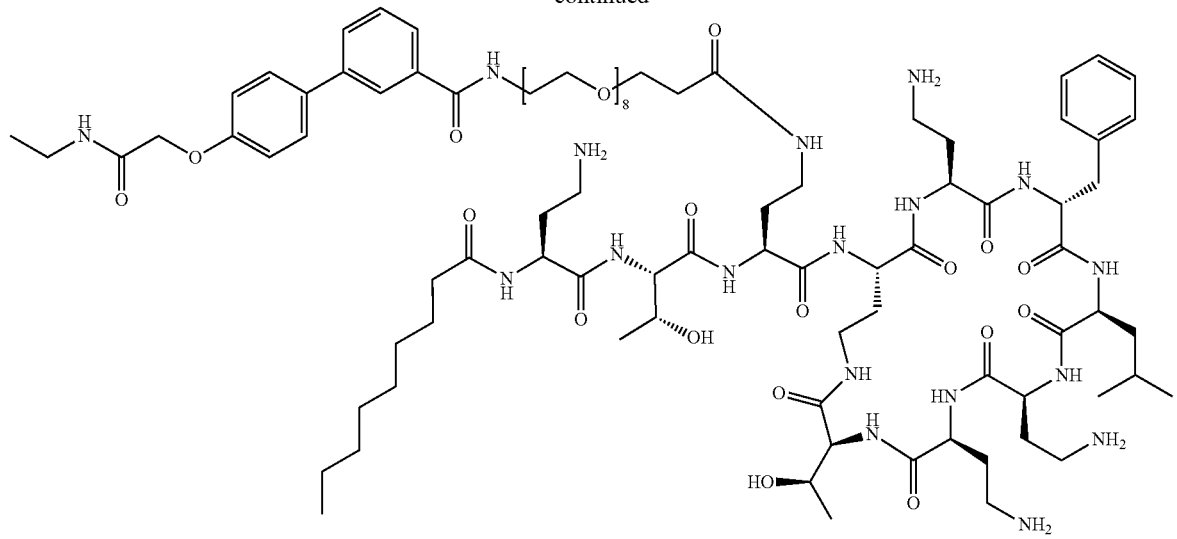
The compound of Example 23 was prepared in an analogous manner to the procedure described in Example 1 using Preparation 15 and Preparation 5.
HPLC (Method 2) Rt=2.983 minutes
MS m/z 1233.7 [M+2H]$^+$/2, 822.7 [M+3H]$^+$/3; theoretical mass: 2464.30
Example 24
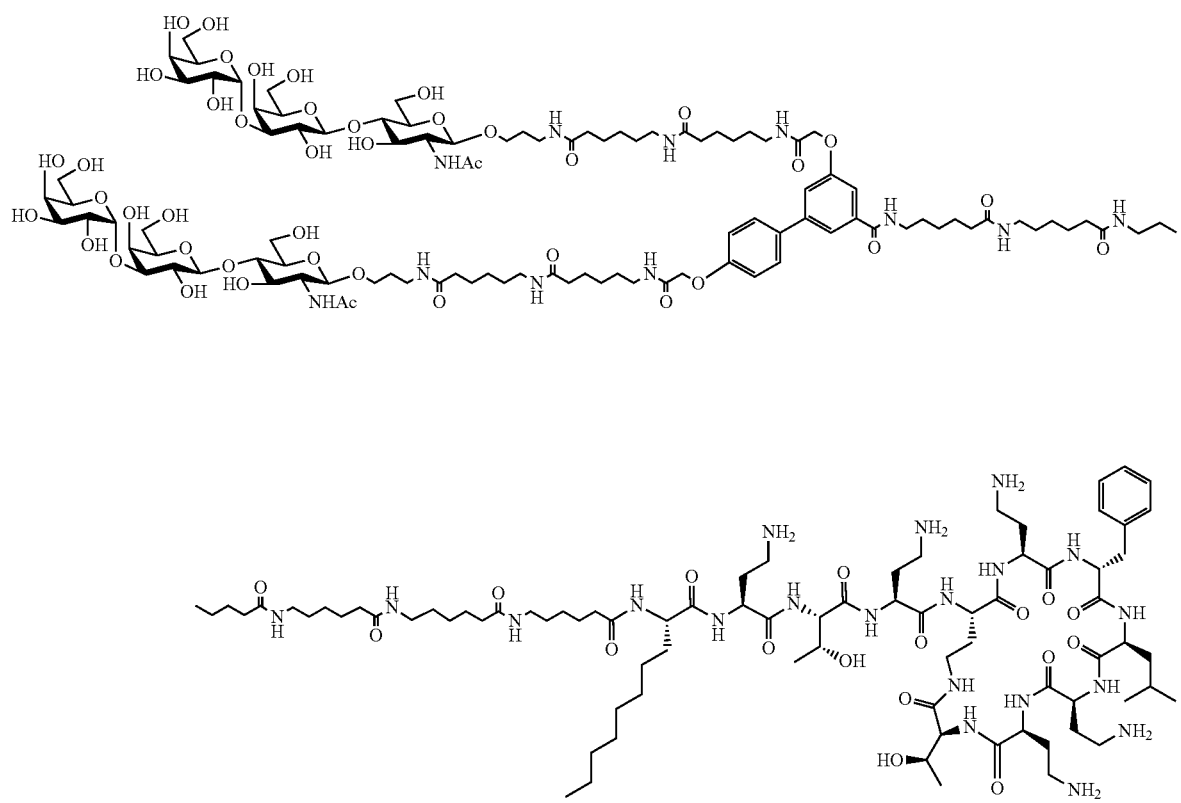

The compound of Example 24 was prepared in an analogous manner to the procedure described in Example 1 using Preparation 28 and Preparation 8.

HPLC (Method 2) Rt=2.852 minutes

MS m/z 1287.6 $[M+3H]^+/3$, 966.3 $[M+4H]^+/4$; theoretical mass: 3861.5

Example 25

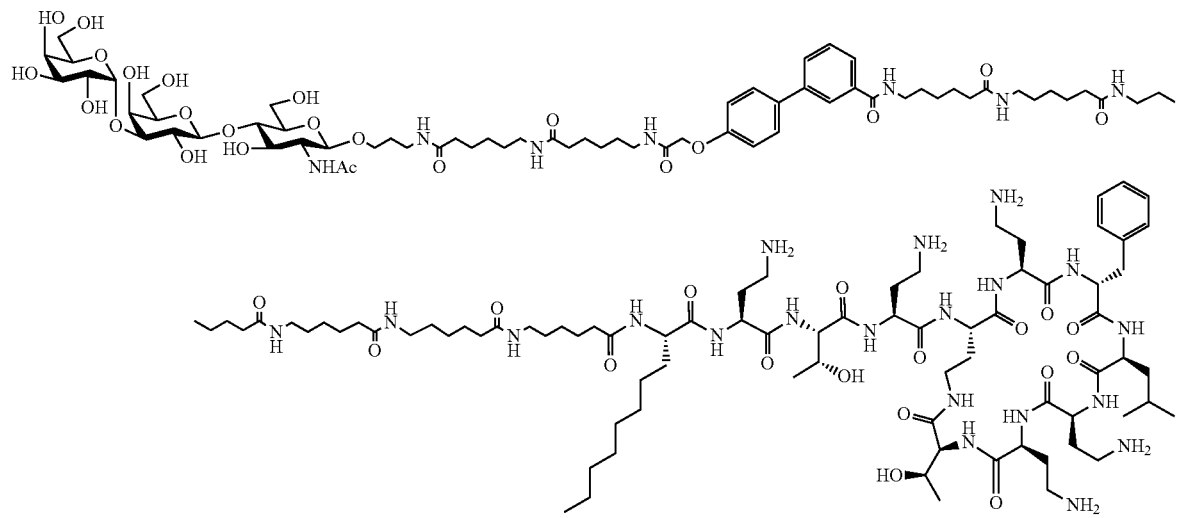

The compound of Example 25 was prepared in an analogous manner to the procedure described in Example 1 using Preparation 26 and Preparation 8.

HPLC (Method 2) Rt=2.990 minutes

MS m/z 993.0 $[M+3H]^+/3$, 745.1 $[M+4H]^+/4$; theoretical mass: 2976.6

Biological Assays

Binding of Compounds to Purified LPS

The binding of compounds to LPS from Gram-negative bacteria is evaluated by measuring displacement of a dansylated derivative of polymyxin B from LPS in an established assay (J. Pharm. Sci. (2016), 105(2), 1006-10; Antimicrob Agents Chemother. (1986), 29(3), 495-550; Anal. Biochem (2011), 409 (2), 273-283). Dansylated polymyxin B was titrated into a LPS solution and the fluorescent intensity was measured (exc 485 nm, em 535 nm). Titration of increasing concentration of lead conjugates or polymyxin B into solution containing LPS and dansylated Polymyxin B corresponding to 95% probe occupancy resulted in decreased fluorescence emission by displacement of dansylated polymyxin B for the candidate.

The lipopolysaccharide (LPS) binding activities of synthetic Polymyxin derived peptides and the Examples herein are evaluated by measuring displacement of Dansyl-Polymxyin B (DPMB) bound to E. coli LPS and P. aeruginosa LPS.

Materials

LPS from Escherichia coli was purchased from Sigma Aldrich, cat #L3024. LPS from Pseudomonas aeruginosa was purchased from Sigma Aldrich, cat #L9143. Polymyxin B sulfate (PMB_std) was purchased from Alfa Aesar, cat #J63074. Polymyxin B nonapeptide hydrochloride (PMB_nona) was purchased from Sigma Aldrich, cat #P2076. Nuclease free water was purchased from Qiagen, cat #129114.

Assay Protocol

Figure 1:
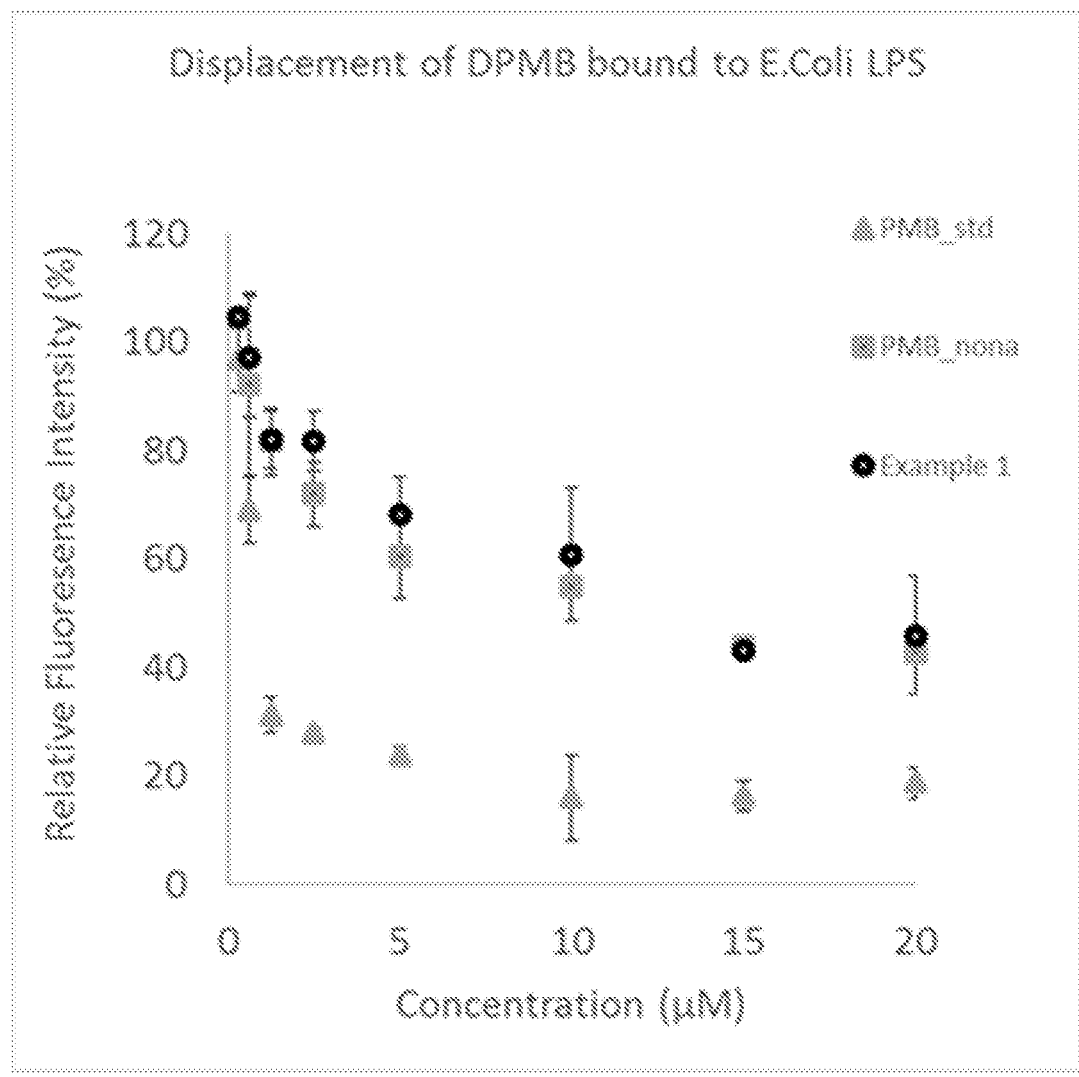
FIG. 1: Displacement of DPMB bound to *E. coli* LPS for 'PMB_std', 'PMB_nona' and Example 1. Percent fluorescence intensity was plotted as a function of test compound concentration. The 100% fluoresence intensity was defined by the positive control of DPMB+LPS. The 0% fluoresence intensity was defined by a negative control of DPMB+water. Samples were run in triplicate for 'PMB_std'. Samples were run in duplicate for 'PMB_nona' and Example 1. The error bars represent SD.
Figure 2:
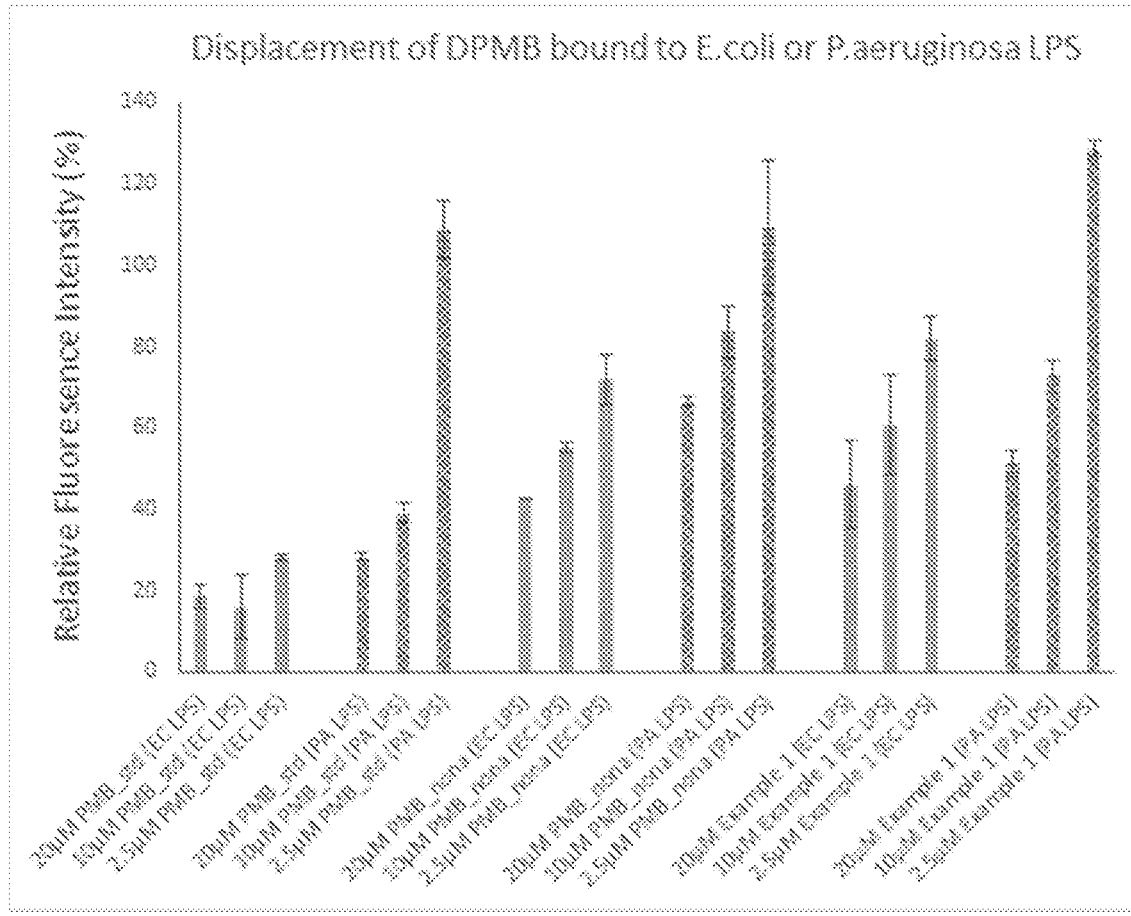
FIG. 2: Displacement of DPMB bound to *E. coli* LPS or *P. aeruginosa* LPS. Percent fluorescence intensity was plotted as a function of test compound concentration. The 100% fluoresence intensity was defined by the positive control of DPMB+LPS. The 0% fluoresence intensity was defined by a negative control of DPMB+water. Samples were run in triplicate for 'PMB_std' and 'PMB_int'. Samples were run in duplicate for 'PMB_nona' and Example 1. The error bars represent SD.

Bacterial LPS was prepared to 20 µg/ml in nuclease free water. DPMB was made to 4 µM in nuclease free water. Bacterial LPS at 20 µg/ml (40 µl) or a negative control of water (40 µl) was equilibrated with DPMB at 4 µM (20 µl) by holding for 5 minutes at room temperature with shaking (450 rpm), in a solid black 96 well plate. Titrations of test compounds at 4× final assay concentration (20 µl) were added to the LPS and DPMB, the assay plate was held for 10 minutes at room temperature with shaking (450 rpm). Fluorescence intensity was captured on an Envision 2102 multilabel plate reader (Em340, Ex485). The compound of Example 1 was tested in the above mentioned binding assay and the results are shown in FIGS. 1 and 2.

Antibody Recruitment Assay by Flow Cytometry Using Anti-Alpha-Galactosyl IgM Antibody Flow cytometry was used to demonstrate binding of L (as a cationic anti-microbial peptide) to E. coli and F (as the carbohydrate molecule capable of binding to a human anti-alpha-galactosyl antibody). A secondary FITC labelled anti-human IgM antibody was used to detect binding of anti-alpha-galactosyl to the compound.

Method 1

The assays were carried out in polystyrene 96-well U bottom plates (Costar). The 96-well plates were pre-blocked with casein blocking buffer (Thermo Fisher 37528) and then washed three times with (HBSS+/+) (Life Technologies 14025-050) prior to assay. E. coli K12 (Public Health England, NCTC 10538) were grown in LB broth (Fisher BP1426-500) to late exponential phase. Subsequently, the bacteria were centrifuged at 10 000 rpm for 5 minutes and resuspended in HBSS+/+ at a bacterial density of $2*10^9$ CFU/mL. Baclight red bacterial stain (ThermoFisher B35001) was added to the bacteria to a final concentration of 1 µM and incubated at room temperature for 10 min. Bacteria were centrifuged (10 000 rpm, 5 minutes) and resuspended in HBSS+/+ at a concentration of $2*10^9$ CFU/mL. $1×10^8$ CFU were then incubated with 20 µM of Examples 2-14 (see Table 1) or buffer alone, at room temperature, shaking at 450 rpm for 1 hour. The bacteria were washed with 3×200 µL HBSS+/+ (centrifuged at 4000 rpm, 5 minutes), prior to adding 50 µL of Anti-alpha galactosyl human IgM M86 antibody (Absolute Antibody Ab00532) at 25 µg/mL in HBSS+/+. Plate was incubated at room temperature for 1 hour shaking at 450 rpm. The bacteria were washed with 3×200 µL HBSS+/+ (centrifuged for 4000 rpm, 5 minutes), prior to adding 100 µL of Anti-human IgM-FITC antibody (Biolegend 314506) at 1:10 dilution in HBSS+/+ and incubated at room temperature for 1 hour shaking at 450 rpm. After a final wash of 3×200 µL HBSS+/+ the bacteria were resuspended in 200 µL HBSS+/+ and evaluated on a FC500 (Beckman Coulter). Bacteria were live gated in the FL-4 channel and median fluorescent shift was recorded in the FL-1 channel. Data from all samples were analysed in the Kaluza software package (Beckman Coulter). Experiment was repeated twice.

Table 1 demonstrates the capture of anti-alpha galactosyl IgM antibodies to the surface of the bacteria using the flow cytometry assay described above. The fold shift over background was calculated by dividing the Median Fluorescent Intensity obtained in the presence 20 µM Examples by the Median Fluorescence Intensity obtained in the absence of Examples. The shift in fluorescence intensity (FITC) occurs due to the binding event at each end of the molecule.

TABLE 1

| Example No. | Anti-alpha galactosyl IgM recruitment at 20 µM (Median Fold shift over vehicle) | Number of Tests (n) |
| --- | --- | --- |
| 1 | 3 | n = 2 |
| 2 | 5 | n = 1 |
| 3 | 7 | n = 2 |
| 4 | 14 | n = 2 |
| 5 | 17 | n = 2 |
| 6 | 24 | n = 2 |
| 7 | 28 | n = 2 |
| 8 | 10 | n = 2 |
| 9 | 21 | n = 4 |
| 10 | 2 | n = 2 |
| 14 | 1 | n = 2 |
| 13 | 2 | n = 2 |
| 11 | 1 | n = 2 |
| 12 | 1 | n = 2 |

Method 2

The assays were carried out in polystyrene 96-well U bottom plates (Costar). E. coli K12 (Public Health England, NCTC 10538) were grown in LB broth (Fisher BP1426-500) to late exponential phase. Subsequently, the bacteria were washed once with HBSS+/+ by centrifuged at 10 000 rpm for 5 minutes and resuspended in HBSS+/+. Bacteria were centrifugated at 10 000 rpm for 5 minutes and resuspended in HBSS+/+ at a bacterial density of $2*10^9$ CFU/mL. $1\times10^8$ CFU were then incubated with 20 µM of Examples 15-25 (see Table 2) or buffer alone, at room temperature, shaking at 450 rpm for 1 hour. The bacteria were washed with 3×200 µL HBSS+/+ (centrifuged at 4000 rpm, 5 minutes), prior to adding 50 µL of Anti-alpha galactosyl human IgM M86 antibody (Absolute Antibody Ab00532) at 25 µg/mL in HBSS+/+. Plate was incubated at room temperature for 1 hour shaking at 450 rpm. The bacteria were washed with 3×200 µL HBSS+/+(centrifuged for 4000 rpm, 5 minutes), prior to adding 100 µL of Anti-human IgM-FITC antibody (Biolegend 314506) at 1:10 dilution in HBSS+/+ and incubated at room temperature for 1 hour shaking at 450 rpm. After a final wash of 3×200 µL HBSS+/+ the bacteria were resuspended in 200 µL HBSS+/+ and evaluated on a Cytoflex (Beckman Coulter). 50 000 counts of bacteria were collected Median fluorescent shift was recorded in the FITC-A channel. Data from all samples were analysed in the Kaluza software package (Beckman Coulter). Experiment was repeated twice.

Table 2 demonstrates the capture of anti-alpha galactosyl IgM antibodies to the surface of the bacteria using the flow cytometry assay described above. The fold shift over background was calculated by dividing the Median Fluorescent Intensity obtained in the presence 20 µM Examples by the Median Fluorescence Intensity obtained in the absence of Examples. The shift in fluorescence intensity (FITC) occurs due to the binding event at each end of the molecule.

TABLE 2

| Example No. | Anti-alphagalactosyl IgM recruitment at 20 µM (Median Fold shift over vehicle) | Number of Tests (n) |
| --- | --- | --- |
| 15 | 248 | n = 4 |
| 16 | 70 | n = 2 |
| 17 | 213 | n = 2 |
| 18 | 65 | n = 2 |
| 19 | 109 | n = 2 |
| 20 | 145 | n = 2 |
| 21 | 158 | n = 2 |
| 22 | 149 | n = 2 |
| 23 | 28 | n = 2 |
| 24 | 269 | n = 4 |
| 25 | 104 | n = 4 |

Antibody Recruitment Assay by Flow Cytometry Using Anti Alpha-Galactosyl IgG Antibody Flow cytometry was used to demonstrate binding of L (as a cationic anti-microbial peptide) to E. coli and F (as the carbohydrate molecule capable of binding to a human anti-alpha-galactosyl antibody). A secondary FITC labelled anti-human IgG antibody was used to detect binding of alpha-galactosyl to the compound.

The assays were carried out in polystyrene 96-well U bottom plates (Costar). The 96-well plates were pre-blocked with casein blocking buffer (Thermo Fisher 37528) and then washed three times with (HBSS+/+) (Life Technologies 14025-050) prior to assay. E. coli K12 (Public Health England, NCTC 10538) were grown in LB broth (Fisher BP1426-500) to late exponential phase. Subsequently, the bacteria were centrifuged at 10 000 rpm for 5 minutes and resuspended HBSS+/+ at a bacterial density of $2*10^9$ CFU/mL. Baclight red bacterial stain (ThermoFisher B35001) was added to the bacteria to a final concentration of 1 µM and incubated at room temperature for 10 min. Bacteria were centrifuged (10 000 rpm, 5 minutes) and resuspended in HBSS+/+ at a concentration of $2*10^9$ CFU/mL. $1\times10^8$ CFU were then incubated with 20 µM of Examples 1-10 (see Table 3) or buffer alone, at room temperature, shaking at 450 rpm for 1 hour. The bacteria were washed with 3×200 µL HBSS+/+ (centrifuged at 4000 rpm, 5 minutes), prior to adding 50 µL of Anti-alpha galactosyl-IgG antibody. (Anti-alpha-galactosyl antibody was purified from human IVIG (Gammagard) by affinity purification using an alpha-galactosyl-HAS (Human Serum Albumin) sepharose column by Rockland Immunochemicals Inc.) at 42 µg/mL in HBSS+/+. Plate was incubated at room temperature for 1 hour shaking at 450 rpm. The bacteria were washed with 3×200 µL HBSS+/+ (centrifuged for 4000 rpm, 5 minutes), prior to adding 100 µL of anti-human IgG-FITC antibody (Biolegend 409310) at 1:20 dilution in HBSS+/+ and incubated at room temperature for 1 hour shaking at 450 rpm. After a final wash of 3×200 μL HBSS+/+ the bacteria were resuspended in 200 μL HBSS+/+ and evaluated on a FC500 (Beckman Coulter). Bacteria were live gated in the FL-4 channel and median fluorescent shift was recorded in the FL-1 channel. Data from all samples were analysed in the Kaluza software package (Beckman Coulter). Experiment was repeated twice.

Table 3 demonstrates the capture of anti-alpha galactosyl IgG antibodies to the surface of the bacteria using the flow cytometry assay described above. The fold shift over background was calculated by dividing the Median Fluorescent Intensity obtained in the presence 20 μM Examples by the Median Fluorescence Intensity obtained in the absence of Examples. The shift in fluorescence intensity (FITC) occurs due to the binding event at each end of the molecule.

TABLE 3

| Example No. | Anti-alphagalactosyl IgG recruitment at 20 μM (Median Fold shift over vehicle) | Number of Tests (n) |
| --- | --- | --- |
| 1 | 1 | n = 1 |
| 2 | 2 | n = 1 |
| 3 | 3 | n = 2 |
| 4 | 8 | n = 2 |
| 5 | 6 | n = 2 |
| 6 | 7 | n = 2 |
| 7 | 6 | n = 2 |
| 8 | 3 | n = 2 |
| 9 | 5 | n = 2 |
| 10 | 1 | n = 2 |

Complement Deposition Assay Flow Cytometry

The assays were carried out in polystyrene 96-well U bottom plates (Costar). *E. coli* K1:O18ac:H7 (ATCC 700973) were grown in LB broth (Fisher BP1426-500) to late exponential phase. Subsequently, the bacteria were centrifuged at 10 000 rpm for 5 minutes and resuspended in PBS (Sigma D8537-500 mL). Bacteria were centrifuged (10 000 rpm, 5 minutes) and resuspended in PBS with 1% BSA (Sigma A2153-50G) at a concentration of $2*10^9$ CFU/mL. $1×10^8$ CFU were then incubated with 20 μM and/or 10 μM of Examples 4-7, 9 and 15-25 (see Table 4 and FIG. 3) or buffer alone, at 4° C. for 45 min. The bacteria were washed with 1×200 μL HBSS+/+ (centrifuged at 4000 rpm, 5 minutes), prior to adding 100 μL of pooled human serum (Innovate Research IPLA-CSER) in PBS+1% BSA to a final serum concentration of 25%. Bacteria were incubated at 37° C. for 20 min. 100 μL ice-cold PBS was added to each well. The plate was centrifugated at 4000 rpm for 5 minutes at 4° C. and supernatant discarded. The bacteria were washed another 2 times with 200 μL HBSS+/+ (centrifuged for 4000 rpm, 5 minutes), prior to adding 100 μL of anti-human C3b/C3bi-PE antibody (Biolegend 846104) at 1:50 dilution in PBS+1% BSA and incubated at 4° C. for 45 min. After a final wash of 3×200 μL HBSS+/+ the bacteria were resuspended in 200 μL HBSS+/+ and evaluated on a Cytoflex (Beckman Coulter). The median fluorescent intensity was recorded in the PE channel. Data from all samples were analyzed in the Kaluza software package (Beckman Coulter).

Table 4 demonstrates the deposition of C3b from human serum to the surface of the bacteria using the flow cytometry assay described above. The fold shift over background was calculated by dividing the Median Fluorescent Intensity obtained in the presence 20 μM Examples by the Median Fluorescence Intensity obtained in the absence of Examples. The shift in fluorescence intensity (PE) occurs due to the recruitment of C3b to the surface of the bacteria.

TABLE 4

| Example | C3b recruitment at 10 μM (Median Fold shift over vehicle) | Number of Tests (n) |
| --- | --- | --- |
| 4 | 95 | n = 4 |
| 5 | 17 | n = 2 |
| 6 | 170 | n = 4 |
| 7 | 4 | n = 2 |
| 9 | 44 | n = 4 |
| 15 | 6 | n = 2 |
| 16 | 47 | n = 4 |
| 17 | 93 | n = 4 |
| 18 | 49 | n = 4 |
| 19 | 59 | n = 4 |
| 20 | 14 | n = 4 |
| 21 | 17 | n = 4 |
| 22 | 16 | n = 4 |
| 23 | 5 | n = 2 |
| 24 | 105 | n = 2 |
| 25 | 113 | n = 2 |

FIG. 3 demonstrates the recruitment of C3b from human serum to the surface of *E. coli* in the presence of Example 4 (FIG. 3A), Example 5 (FIG. 3B), Example 6 (FIG. 3C) Example 7 (FIG. 3D) and Example 9 (FIG. 3E) at 20 μM. The shift in fluorescence intensity (PE) occurs due to the recruitment of C3b from serum to the bacteria surface.

The invention claimed is:

1. A compound of formula (I) or a pharmaceutically acceptable salt thereof:

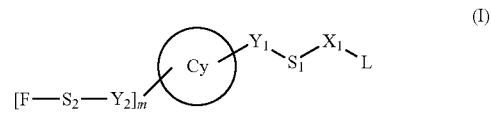

wherein:
L represents a binding moiety selected from a cationic anti-microbial peptide linked to $X_1$ by an amine;
$S_1$ represents a bond or a spacer selected from a —$(CH_2)_a$— or —$(CH_2)_b$—$(CH_2$—$CH_2O)_c$—$(CH_2)_d$— group, wherein one to five of said —$CH_2$— groups may optionally be substituted by a —C(O)NH— or —NHC(O)— group;
a represents an integer selected from 1 to 40;
b represents an integer selected from 0 to 25;
c represents an integer selected from 1 to 20;
d represents an integer selected from 1 to 15;
$S_2$ represents a spacer selected from a —$(CH_2)_e$— or —$(CH_2)_f$—$(CH_2$—$CH_2O)_g$—$(CH_2)_h$— group, wherein one to three of said —$CH_2$— groups may optionally be substituted by a —C(O)NH— or —NHC(O)— group;
e represents an integer selected from 1 to 20;
f represents an integer selected from 1 to 10;
g represents an integer selected from 1 to 15;
h represents an integer selected from 1 to 5;
$X_1$ represents a bond or —C(O)—;
$Y_1$ and $Y_2$ independently represent a bond, —O—, —S—, —NH—, —C(O)—, —NHC(O)— or —C(O)NH— group;
F represents a carbohydrate molecule capable of binding to a human anti-alpha-galactosyl antibody;
m represents an integer selected from 1 to 5; and Cy represents phenyl, biphenyl or triphenyl, such that when Cy represents biphenyl or triphenyl, said —Y$_1$—S$_1$—X$_1$-L group may be present on any of said phenyl rings and said [F—S$_2$—Y$_2$]$_m$— group or groups may be present on any of said phenyl rings.

2. The compound as defined in claim 1 or a pharmaceutically acceptable salt thereof, wherein S$_1$ represents a bond or a spacer selected from:
—(CH$_2$)$_a$—, wherein one or five of said —CH$_2$— groups are optionally substituted by a —C(O)NH— group (such as —(CH$_2$)$_5$—CONH—(CH$_2$)$_5$ or —(CH$_2$)$_5$—CONH—(CH$_2$)$_5$—CONH—(CH$_2$)$_5$—CONH—(CH$_2$)$_5$—CONH—(CH$_2$)$_5$—CONH—(CH$_2$)$_5$—); or
—(CH$_2$)$_b$—(CH$_2$—CH$_2$O)$_c$—(CH$_2$)$_d$—, wherein two of said —CH$_2$— groups are optionally substituted by a —C(O)NH— group (such as —(CH$_2$CH$_2$O)$_8$—(CH$_2$)$_2$—, —(CH$_2$CH$_2$O)$_8$—(CH$_2$)$_2$—CONH—(CH$_2$)$_5$—CONH—(CH$_2$)$_5$— or —(CH$_2$)$_5$—CONH—(CH$_2$)$_5$—CONH—(CH$_2$)$_5$—CONH—(CH$_2$)$_5$—CONH—(CH$_2$CH$_2$O)$_8$—(CH$_2$)$_2$—);

or S$_1$ represents a spacer selected from:
—(CH$_2$)$_a$—, wherein one of said —CH$_2$— groups is substituted by a —C(O)NH— group (such as —(CH$_2$)$_5$—CONH—(CH$_2$)$_5$); or
(CH$_2$)$_b$—(CH$_2$—CH$_2$O)$_c$—(CH$_2$)$_d$— (such as —(CH$_2$CH$_2$O)$_8$—(CH$_2$)$_2$—);

or S$_1$ represents a spacer selected from: —(CH$_2$)$_a$—, wherein one of said —CH$_2$— groups is substituted by a —C(O)NH— group (such as —(CH$_2$)$_5$—CONH—(CH$_2$)$_5$).

3. The compound as defined in claim 1 or a pharmaceutically acceptable salt thereof, wherein a represents an integer selected from: 1 to 35; or 10 to 35; or 11 or 35; or 11.

4. The compound as defined in claim 1 or a pharmaceutically acceptable salt thereof, wherein b represents an integer selected from 0 to 24; or 0 or 24; or 0.

5. The compound as defined in claim 1 or a pharmaceutically acceptable salt thereof, wherein c represents an integer selected from 1 to 15; or 1 to 10; or 8.

6. The compound as defined in claim 1 or a pharmaceutically acceptable salt thereof, wherein d represents an integer selected from 1 to 3; or 1 or 2; or 2.

7. The compound as defined in claim 1 or a pharmaceutically acceptable salt thereof, wherein Y$_1$ represents —C(O)NH— or —C(O)—; or —C(O)NH—.

8. The compound as defined in claim 1 or a pharmaceutically acceptable salt thereof, wherein S$_2$ represents a spacer selected from:
—(CH$_2$)$_e$—, wherein one or three of said —CH$_2$— groups are optionally substituted by a —NHC(O)— group (such as —(CH$_2$)$_3$—NHCO—CH$_2$— or —(CH$_2$)$_3$—NHCO—(CH$_2$)$_5$—NHCO—(CH$_2$)$_5$—NHCO—CH$_2$—); or
—(CH$_2$)$_f$—(CH$_2$—CH$_2$—O)$_g$—(CH$_2$)$_h$—, wherein two of said —CH$_2$— groups are optionally substituted by a —NHC(O)— group (such as —(CH$_2$)$_3$—NHCO—(CH$_2$CH$_2$O)$_4$—(CH$_2$)$_2$—NHCO—CH$_2$—);

or S$_2$ represents a spacer selected from —(CH$_2$)$_e$—, wherein three of said —CH$_2$— groups are optionally substituted by a —NHC(O)— group (such as —(CH$_2$)$_3$—NHCO—(CH$_2$)$_5$—NHCO—(CH$_2$)$_5$—NHCO—CH$_2$—).

9. The compound as defined in claim 1 or a pharmaceutically acceptable salt thereof, wherein e represents an integer selected from 1 to 17; or 5 to 17; or 5 or 17; or 17.

10. The compound as defined in claim 1 or a pharmaceutically acceptable salt thereof, wherein f represents an integer selected from 1 to 8; or 2 to 6; or 4.

11. The compound as defined claim 1 or a pharmaceutically acceptable salt thereof, wherein g represents an integer selected from 1 to 5; or 1 to 4; or 4.

12. The compound as defined in claim 1 or a pharmaceutically acceptable salt thereof, wherein h represents an integer selected from 1 to 4; or 4.

13. The compound as defined in claim 1 or a pharmaceutically acceptable salt thereof, wherein X$_1$ represents —C(O)—.

14. The compound as defined in claim 1 or a pharmaceutically acceptable salt thereof, wherein Y$_2$ represents —O—.

15. The compound as defined in claim 1 or a pharmaceutically acceptable salt thereof, wherein m represents an integer selected from 1 to 4; or 1, 2 or 3; or 1 or 2; or 1.

16. The compound as defined in claim 1 or a pharmaceutically acceptable salt thereof, wherein Cy represents phenyl or biphenyl; or biphenyl.

17. The compound as defined in claim 1 or a pharmaceutically acceptable salt thereof, wherein F is selected from galactosyl-alpha-1,3-galactosyl-beta-1,4-N-acetylglucosamine, alpha1-3 galactobiose, alpha1-3-beta1-4-galactotriose or galilipentasaccharide.

18. The compound as defined in claim 1 or a pharmaceutically acceptable salt thereof, wherein F has a structure as shown in the following formula:

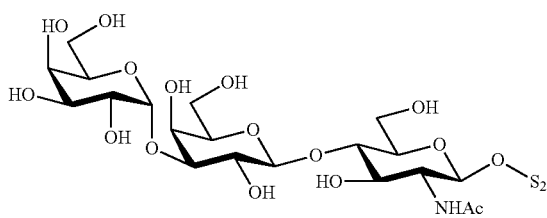

wherein S$_2$ refers to the point of attachment to the S$_2$ group.

19. The compound as defined in claim 1 or a pharmaceutically acceptable salt thereof, wherein L represents a lipopeptide.

20. The compound as defined in claim 1 or a pharmaceutically acceptable salt thereof, wherein L represents a lipopeptide; or a Polymyxin B derivative; or a Polymyxin B derivative selected from one of the following structures:

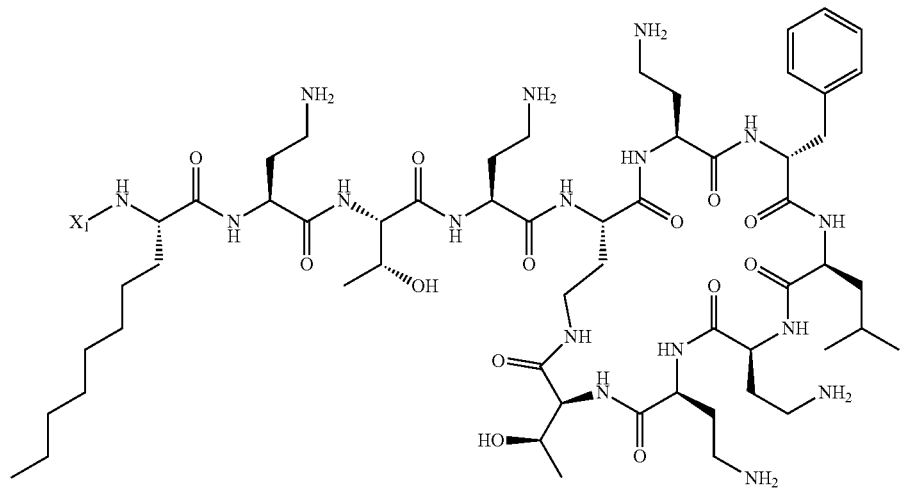
H₂N-[L-OctylGly]-Dab-Thr-Dab-Dab*-Dab-[D-Phe]-Leu-Dab-Dab-Thr*
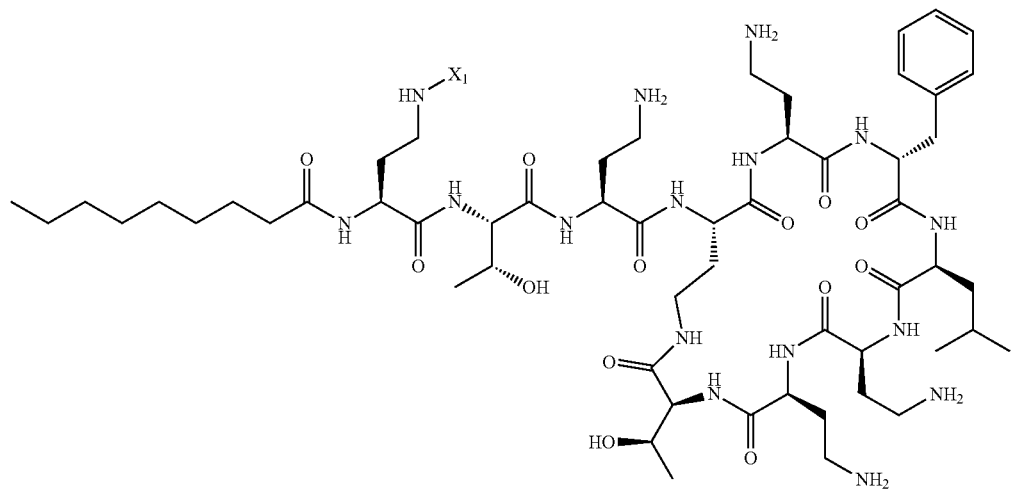
Nonanamide-Dab(NH₂)-Thr-Dab-Dab*-Dab-[D-Phe]-Leu-Dab-Dab-Thr*
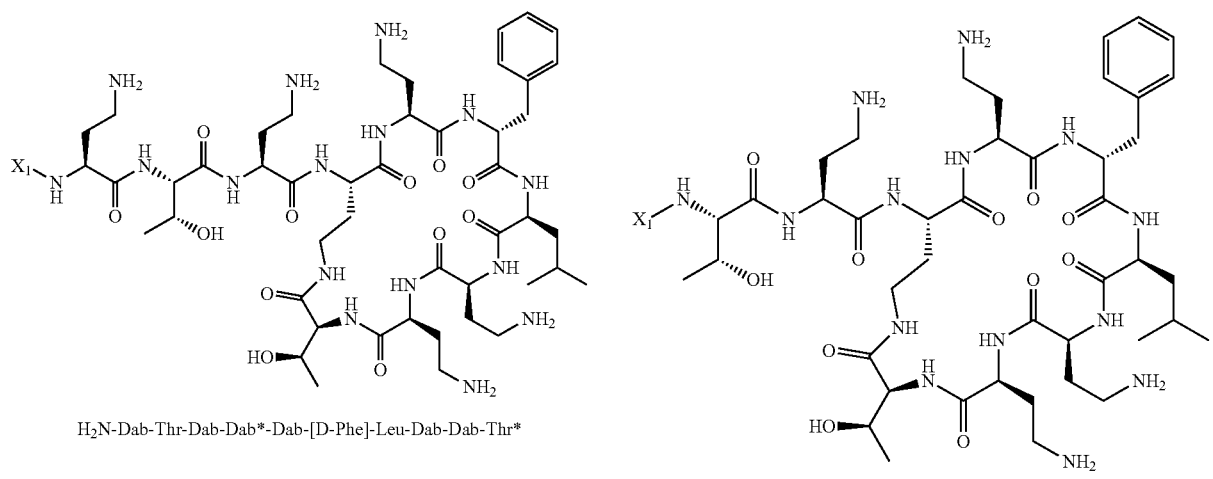
H₂N-Dab-Thr-Dab-Dab*-Dab-[D-Phe]-Leu-Dab-Dab-Thr*
H₂N-Thr-Dab-Dab*-Dab-[D-Phe]-Leu-Dab-Dab-Thr*

-continued
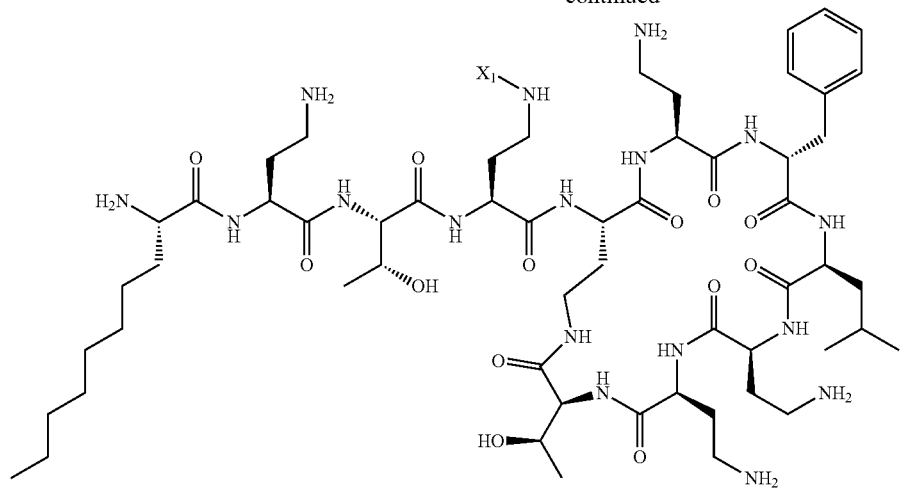
H₂N-[L-OctylGly]-Dab-Thr-Dab(NH₂)-Dab*-Dab-[D-Phe]-Leu-Dab-Dab-Thr*
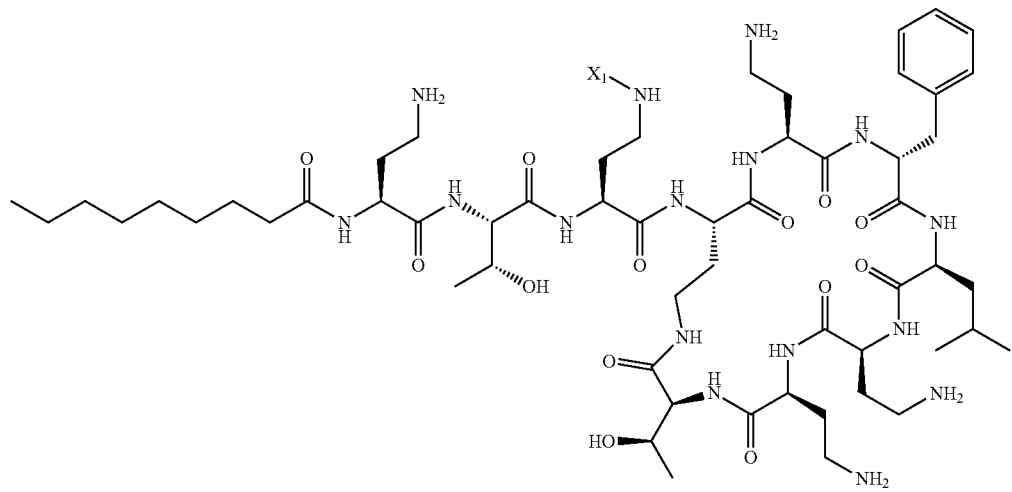
Nonanamide-Dab-Thr-Dab-Dab(NH₂)-Dab*-Dab-[D-Phe]-Leu-Dab-Dab-Thr*
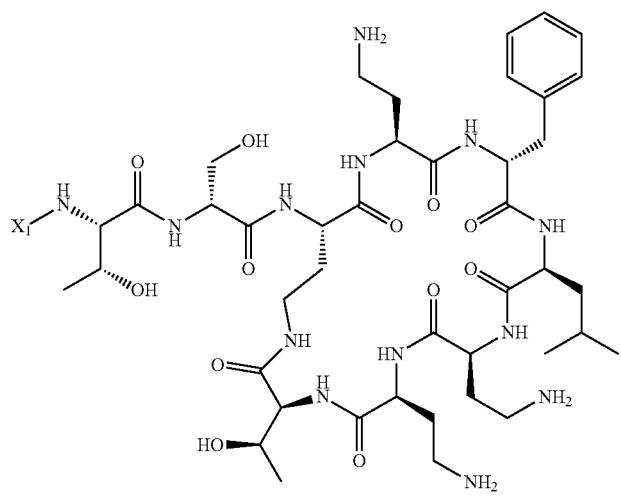
H₂N-Thr-[D-Ser]-Dab*-Dab-[D-Phe]-Leu-Dab-Dab-Thr* wherein $X_1$ refers to the point of attachment to the $X_1$ group.

21. The compound as defined in claim 1 or a pharmaceutically acceptable salt thereof, which is selected from any one of Examples 1-25.

22. A pharmaceutical composition comprising a compound as defined in claim 1 or a pharmaceutically acceptable salt thereof.

23. A method of treating a bacterial infection which comprises administering to an individual in need thereof a compound of formula (I) as defined in claim 1 or a pharmaceutically acceptable salt thereof.

24. A process for preparing a compound of formula (I) as defined in claim 1 which comprises:
   (a) preparing a compound of formula (I) wherein $Y_1$ represents —CONH— (i.e. a compound of formula (IA)) by reacting a compound of formula (II) with a compound of formula (III) followed by a suitable deprotection step:

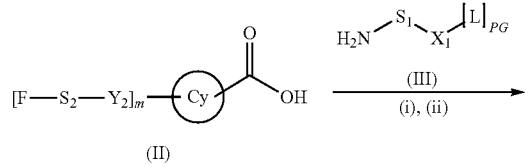

wherein $S_2$, $Y_2$, m, Cy, $S_1$, $X_1$, L and F are as defined in claim 1 and PG is a suitable peptide protecting group such as Dde; or (b) preparing a compound of formula (I) wherein $Y_1$ represents —CONH— and $X_1$ represents —C(O)— (i.e. a compound of formula (IB)) by reacting a compound of formula (IV) with a compound of formula (V) followed by a suitable deprotection step:

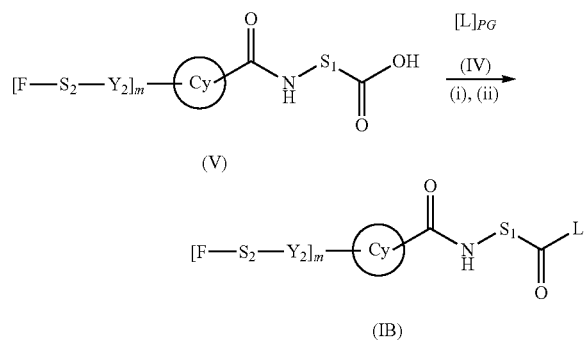

wherein $S_2$, $Y_2$, m, Cy, $S_1$, L and F are as defined in claim 1 and PG is a suitable peptide protecting group such as Dde; or (c) preparing a compound of formula (I) by reacting a compound of formula (VI) with a compound of formula (VII) followed by a suitable deprotection step:

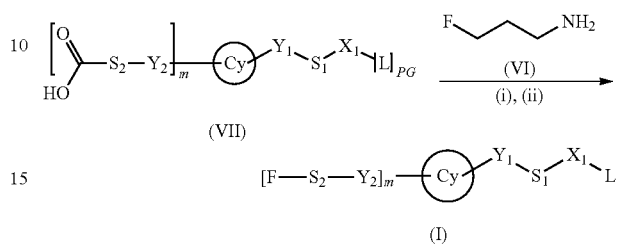

wherein $S_2$, $Y_2$, m, Cy, $S_1$, $X_1$, L and F are as defined in claim 1, PG is a suitable peptide protecting group such as Dde; or (d) preparing a compound of formula (I) by reacting a compound of formula (XII) with a compound of formula (XIII) followed by a suitable deprotection step, wherein $Y_1$ represents a CONH group:

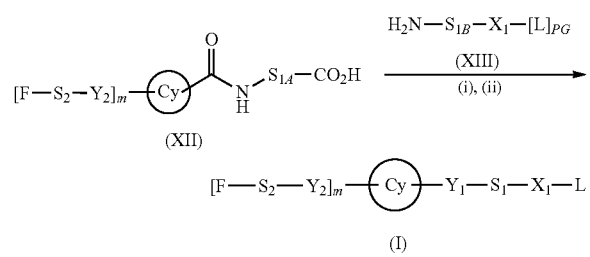

wherein $S_2$, $Y_2$, m, Cy, $X_1$, L and F are as defined hereinbefore, $S_{1A}$ and $S_{1B}$ together form an $S_1$ group and PG is a suitable peptide protecting group such as Dde; or (e) interconversion of a compound of formula (I) or protected derivative thereof to a further compound of formula (I) or protected derivative thereof.

25. The compound as defined in claim 19, wherein the lipopeptide is a polymyxin selected from the group consisting of Polymyxin B, Polymyxin $B_2$, Polymyxin Nonapeptide, Colistin A, Colistin B, CB-182,204 (Cubist Pharmaceuticals), 5a (Pfizer), 5x (Pfizer), CA 14 (Cantab Anti-Infectives) CA824 (Cantab Anti-Infectives), NAB739 (Northern Antibiotics), NAB741 (Northern Antibiotics), NAB7061 (Northern Antibiotics), 38 (University of Queensland), FADDI-002 (Monash University), and FADDI-100 (Monash University), or derivatives thereof.

* * * * *